US012263243B2

(12) United States Patent
Johnston et al.

(10) Patent No.: US 12,263,243 B2
(45) Date of Patent: *Apr. 1, 2025

(54) TEMPLATED OPEN FLOCS OF ANISOTROPIC PARTICLES FOR ENHANCED PULMONARY DELIVERY

(75) Inventors: Keith P. Johnston, Austin, TX (US); Joshua Engstrom, Spotswood, NJ (US); Jasmine Tam, Austin, TX (US); Robert O. Williams, III, Austin, TX (US); Alan B. Watts, Austin, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 1556 days.

This patent is subject to a terminal disclaimer.

(21) Appl. No.: 12/371,573

(22) Filed: Feb. 13, 2009

(65) Prior Publication Data

US 2009/0208582 A1 Aug. 20, 2009

Related U.S. Application Data

(60) Provisional application No. 61/028,218, filed on Feb. 13, 2008.

(51) Int. Cl.
*A61K 9/00* (2006.01)

(52) U.S. Cl.
CPC ............ *A61K 9/008* (2013.01); *A61K 9/0075* (2013.01)

(58) Field of Classification Search
None
See application file for complete search history.

(56) References Cited

U.S. PATENT DOCUMENTS

| | | | |
|---|---|---|---|
| 6,284,282 | B1 | 9/2001 | Maa et al. |
| 6,451,339 | B2* | 9/2002 | Patel ................. A61P 15/06 424/463 |
| 6,585,957 | B1 | 7/2003 | Adjei et al. |
| 6,655,381 | B2 | 12/2003 | Keane et al. |
| 7,011,818 | B2 | 3/2006 | Staniforth |
| 7,306,787 | B2 | 12/2007 | Tarara et al. |
| 2003/0064029 | A1* | 4/2003 | Tarara et al. ............... 424/45 |
| 2003/0232020 | A1* | 12/2003 | York ............... A61K 9/1688 424/46 |
| 2004/0105821 | A1 | 6/2004 | Bernstein et al. |
| 2004/0137070 | A1 | 7/2004 | Scherzer et al. |
| 2004/0176391 | A1* | 9/2004 | Weers .............. A61K 9/0075 514/254.07 |
| 2007/0287675 | A1 | 12/2007 | Hitt et al. |
| 2008/0118442 | A1 | 5/2008 | Mohsen et al. |
| 2010/0221343 | A1 | 9/2010 | Johnston et al. |
| 2010/0273728 | A1* | 10/2010 | Wasan ................ A61P 37/06 514/786 |

FOREIGN PATENT DOCUMENTS

| | | |
|---|---|---|
| WO | 2003090715 A2 | 11/2003 |
| WO | 2005025506 | 3/2005 |
| WO | WO 2006/026502 | 3/2006 |
| WO | 2009103035 A2 | 8/2009 |

OTHER PUBLICATIONS

Sigma Aldrich catalog entry: itraconazole. Accessed on Oct. 11, 2011 at http://www.sigmaaldrich.com/catalog/Lookup.do?N5=All &N3=mode+matchpartialmax&N4=itraconazole&D7=0&D10= itraconazole&N1=S_ID&ST=RS&N25=0&F=PR.*
Merriam-Webster online medical dictionary definitions: atomize, compact, floc, flocculate, flocculent, porous, template. Accessed at http://www.merriam-webster.com/ on May 19, 2012.*
Hilker R [Editor]. "Polymorphism in the Pharmaceutical Industry". Wiley-VCH Verlag GmbH & Co., 2006. pp. 1-19. (Year: 2006).*
Gattefosse [Online]. "Gelucire 50/13". [Retrieved Nov. 22, 2023]. Retrieved from the Internet: <URL: https://www.gattefosse.com/pharmaceuticals/product-finder/gelucire-5013>. (Year: 2023).*
Dellamary, L. A., et al., "Hollow porous particles in metered dose inhalers," Pharm. Res. (2000) 17:168-174.
Engstrom, J. D., et al., "Morphology of protein particles produced by spray freezing of concentrated solutions," Eur. J. Pharm. Biopharm. (2007) 65:149-162.
Engstrom, J. D., et al., "Stable high surface area lactate dehydrogenase particles produced by spray freezing into liquid nitrogen," Eur. J. Pharm. Biopharm. (2007) 65:163-174.
Garcia-Contreras, L., et al., "Liquid-spray or dry-powder systems for inhaled delivery of peptide and proteins?," Am. J. Drug Delivery (2005) 3:29-45.
Kwon, M. J., et al., "Long acting porous microparticle for pulmonary protein delivery," Int. J. Pharm. (2007) 333:5-9.
Liao, Y.-H., et al., "The effects of polyvinyl alcohol on the in vitro stability and delivery of spray-dried protein particles from surfactant-free HFA 134a-based pressurised metered dose inhalers," Int. J. Pharm. (2005) 304:29-39.
Nguyen, X. C., et al., "Protein powders for encapsulation: a comparison of spray-freeze drying and spray drying of darbepoetin alfa," Pharm. Res. (2004) 21507-514.
Patton, J. S., et al., "Inhaling medicines: delivering drugs to the body through the lungs," Nature Rev. Drug Discovery (2007) 6:67-74.
Rogers, T. L., et al., "A novel particle engineering technology to enhance dissolution of poorly water soluble drugs: spray-freezing into liquid," Eur. J. Pharm. Biopharm. (2002) 54:271-280.

(Continued)

*Primary Examiner* — Leslie A. Royds Draper
(74) *Attorney, Agent, or Firm* — Parker Highlander PLLC

(57) ABSTRACT

The present invention includes compositions and methods for treating and delivering medicinal formulations using an inhaler. The composition includes a space filled flocculated suspension having one or more flocculated particles of one or more active agents and a hydrofluoroalkane propellant. A portion of the one or more flocculated particles is templated by the formation of hydrofluoroalkane droplets upon atomization and the templated floc compacts upon the evaporation of the hydrofluoroalkane propellant to form a porous particle for deep lung delivery.

7 Claims, 29 Drawing Sheets

(56) References Cited

OTHER PUBLICATIONS

Rogers, T. L., et al., "Micronized powders of a poorly water soluble drug produced by a spray-freezing into liquid-emulsion process," Eur. J. Pharm. Biopharm. (2003) 55:161-72.

Rogueda, P., Novel hydrofluoroalkane suspension formulations for respiratory drug delivery, Expert Opinion Drug Del. (2005) 2:625-638.

Shekunov, B. Y., et al., "Particle Size Analysis in Pharmaceutics: Principles, Methods and Applications," Pharm. Res. (2007) 24:203-227.

Shoyele, S. A., et al., "Prospects of formulating proteins/peptides as aerosols for pulmonary drug delivery," Int. J. Pharm. (2006) 314:1-8.

Traini, D., et al., "Surface Energy and Interparticle Forces Correlations in Model pMDI Formulations," Pharm. Res. 22 (2005) 816-825.

Traini, D., et al., "In vitro investigation of drug particulates interactions and aerosol performance of pressurised metered dose inhalers," Pharm. Res. (2007) 24:125-135.

White, S., et al., "Exubera: Pharmaceutical Development of a Novel Product for Pulmonary Delivery of Insulin," Diabetes Tech. Therapeutics (2005) 7:896-906.

Yu, Z., et al., "Preparation and characterization of microparticles containing peptide produced by a novel process: spray freezing into liquid," Eur. J. Pharm. Biopharm. (2002) 54:221-228.

Yu, Z., et al., "Spray freezing into liquid nitrogen for highly stable protein nanostructured microparticles," Eur. J. Pharm. Biopharm. (2004) 58:529-537.

Yu, Z., et al., "Spray freezing into liquid versus spray-freeze drying: Influence of atomization on protein aggregation and biological activity," Eur. J. Pharm. Sci. (2006) 27:9-18.

Zhanpeng, J., et al., "Flocculation morphology: effect of particulate shape and coagulant species on flocculation," Water Sci. Technol. (2006) 53:9-16.

Engstrom, J. D., et al., "Templated Open Flocs of Nanorods for Enhanced Pulmonary Delivery with Pressurized Metered Dose Inhalers," Pharmaceutical Research (2009), 26:101-117.

Stein, S. W., et al., "The Relative Influence of Atomization and Evaporation on Metered Dose Inhaler Drug Delivery Efficiency," Aerosol Science and Technology (2006), 40:335-347.

Abramowitz, H, et al., "Welding Colloidal Crystals with Carbon Dioxide," Macromolecules, 2004; 37(19): 7316-7324.

Adler, M, et al., "Stability and Surface Activity of Lactate Dehydrogenase in Spray-Dried Trehalose," J. Pharm. Sci., 1999; 88(2):199-208.

Agu, Ru, et al., "The Lung as a Route for Systemic Delivery of Therapeutic Proteins and Peptides," Respiratory Research, 2001; 2(4):198-209.

Ashayer, R, et al., "Investigation of the Molecular Interactions in a pMDI Formulation by Atomic Force Microscopy," Eur. J. Pharm. Sci., 2004; 21:533-543.

Benfait, C, "Kos Reports Achievement of New Research and Development Milestones," Kos Press Release (2004).

Ben-Jebria, A, et al., "Large Porous Particles for Sustained Protection from Carbachol-Induced Bronchoconstriction in Guinea Pigs," Pharm. Res., 1999; 16(4):555-561.

Berlin, E, et al., "Densities of Several Proteins and L-Amino Acids in the Dry State," J. Phys. Chem., 1968; 72(6):1887-9.

Blondino, FE, et al., "Surfactant Dissolution and Water Solubilization in Chlorine-Free Liquified Gas Propellants," Drug Dev. Ind. Pharm., 1998; 24:935-945.

Bower, C, et al., "Fractal Morphology of Drug Aggregates in Aerosol Propellant Suspensions," International Journal of Pharmaceutics, 1995; 118:229-235.

Carpenter, JF, et al., "Rational Design of Stable Lyophilized Protein Formulations: Theory and Practice," in: J.F. Carpenter, M.C. Manning (Eds), Pharmaceutical Biotechnology. 13. Rational Design of Stable Protein Formulations, Kluwer Academic/Plenum Press, New York, 2002, pp. 109-133.

Codrons, V, et al., "Systemic Delivery of Parathyroid Hormone (1-34) Using Inhalation Dry Powders in Rats," J. Pharm. Sci., 2003; 92(5):938-950.

Costantino, HR, et al., "Protein Spray-Freeze Drying. Effect of Atomization Conditions on Particle Size and Stability," Pharm. Res., 2000; 17(11):1374-1383.

Courrier, HM, et al., "Pulmonary Drug Delivery Systems: Recent Developments and Prospects," Crit. Rev. Therapeutic Drug Carrier Systems, 2002; 19(4&5):425-498.

Edwards, DA, et al., "Large Porous Particles for Pulmonary Drug Delivery," Science, 1997; 276:1868-1871.

Engstrom, JD, et al., "Formation of Stable Submicron Protein Particles by Thin Film Freezing," Pharm. Res., 2008; 25(6):1334-1346.

Farahnaky, A, et al., "Enthalpy Relaxation of Bovine Serum Albumin and Implications for its Storage in the Glassy State," Biopolymers, 2005; 78:69-77.

Fargues, C, et al., "Structural Characterization of Flocs in Relation to their Settling Performances," TranslChemE, 2003; 81(A):1171-1178.

Fargues, C, et al., "Structural Characterization of Flocs in Relation to their Settling Performances," (Erratum), Chem. Eng. Res. Design, 2004; 82:1517.

Gonda, I, "Development of a Systematic Theory of Suspension Inhalation Aerosols. I. A Framework to Study the Effects of Aggregation on the Aerodynamic Behaviour of Drug Particles," Int. J. Pharm., 1985; 27:99-116.

Goodarz-Nia, I, et al., "Floc Simulation. Effects of Particle Size and Shape," Chem. Eng. Sci., 1975; 30:407-12.

Heyder, J, et al., "Deposition of Particles in the Human Respiratory Tract in the Size Range 0.005-15 mm," J. Aerosol Sci., 1986; 17(5):811-825.

Johnson, KA, "Interfacial Phenomena and Phase Behavior in Metered Dose Inhaler Formulations," in: A.J. Hickey (Ed), Inhalation Aerosols: Physical and Biological Basis for Therapy, 2007.

Keller, M, "Innovations and Perspectives of Metered Dose Inhalers in Pulmonary Drug Delivery," Int. J. Pharm. 186(1999) 81-90.

Kim, Y, et al., "Determination of Water in Pressurized Pharmaceutical Metered Dose Aerosol Products," Drug Dev. and Ind. Pharm., 1992; 18(20):2185-95.

Maa, Y-F, et al., "Biopharmaceutical Powders: Particle Formation and Formulation Considerations," Curr. Pharm. Biotechnol., 2000; 1(3):283-302.

Maa, Y-F, et al., Spray Freeze-Drying of Biopharmaceuticals: Applications and Stability Considerations, in: H.R. Costantino, M.J. Pikal (Eds), Biotechnology: Pharmaceutical Aspects. 2. Lyophilization of Biopharmaceuticals, American Association of Pharmaceutical Scientists, Arlington, 2004, pp. 519-561.

Maa, Y-F, et al., "Protein Inhalation Powders: Spray Drying vs Spray Freeze Drying," Pharm. Res. 16 (1999) 249-254.

Nail, SL, et al., "Fundamentals of Freeze-Drying," in: S.L. Nail, M.J. Akers (Eds), Pharmaceutical Biotechnology. 14. Development and Manufacture of Protein Pharmaceuticals, Kluwer Academic/Plenum Publishers, New York, 2002, pp. 281-360.

Oliver, MJ, et al., "Initial Assessment of a Protein Formulated in Pressurized Metered Dose Inhalers for Pulmonary Delivery," Respiratory Drug Delivery VII, 2000.

Peguin, RPS, et al., "Microscopic and Thermodynamic Properties of the HFA134a-Water Interface: Atomistic Computer Simulations and Tensiometry under Pressure," Langmuir, 2006; 22(21):8826-8830.

Philipse, AP, et al., "On the Density and Structure Formation in Gels and Clusters of Colloidal Rods and Fibers," Langmuir, 1998(1); 14:49-54.

Philipse, AP, "The Random Contact Equation and Its Implications for (Colloidal) Rods in Packings, Suspensions, and Anisotropic Powders," Langmuir, 1996; 12(5):1127-1133.

Philipse, AP, "The Random Contact Equation and Its Implications for (Colloidal) Rods in Packings, Suspensions, and Anisotropic Powders," (Additions and Corrections), Langmuir, 1996; 12:5971.

Quinn, EA, et al., "Protein Conformational Stability in the Hydrofluoroalkane Propellants Tetrafluoroethane and Heptafluoropropane Analysed by Fourier Transform Raman Spectroscopy," Int. J. Pharm., 1999; 186:31-41.

(56) References Cited

OTHER PUBLICATIONS

Rogueda, PGA, HPFP, "A Model Propellant for pMDIs," Drug Dev. Ind. Pharm., 2003; 29(1):39-49.
Smith, JR, PG, et al., "Electrostatically Stabilized Metal Oxide Particle Dispersions in Carbon Dioxide," J. Phys. Chem. B, 2005; 109(43):20155-20165.
Smyth, HDC, et al., "Aerosol Generation from Propellant-Driven Metered Dose Inhalers," in: J. Hickey Anthony (Ed), Inhalation Aerosols: Physical and Biological Basis for Therapy, 2007, pp. 399-416.
Stein, Stephen W, et al. "The Relative Influence of Atomization and Evaporation on Metered Dose Inhaler Drug Delivery Efficiency," Aerosol Science and Technology, 2006, 40:335-347.
Tadmor, R, "The London-van der Waals Interaction Energy Between Objects of Various Geometries," J. Phys.: Condens. Matter 13 (2001) L195-L202.
Takashima, S, "A Study of Proton Fluctuation in Protein. Experimental Study of the Kirkwood-Shumaker Theory," J. Phys. Chem., 1965; 69:2281-6.
Tam, JT, et al., "Amorphous Cyclosporin A Nanodispersions for Enhanced Pulmonary Deposition and Dissolution," J. Pharm. Sci., 2007:1-19.
Tang, P, et al., "A Model to Describe the Settling Behavior of Fractal Aggregates," J. Colloid Interface Sci., 2002; 247:210-219.
Traini, D, et al., "The Use of AFM and Surface Energy Measurements to Investigate Drug-Canister Material Interactions in a Model Pressurized Metered Dose Inhaler Formulation," Aerosol Sci. Tech., 2006; 40:227-236.
Tsapis, N, et al., "Trojan Particles: Large Porous Carriers of Nanoparticles for Drug Delivery," Proc. Natl. Acad. Sci. U. S. A., 2002; 99(19):12001-12005.
Ulrich, DR, "Chemical Processing of Ceramics," Chem. Eng. News, 1990; 68:28-40.
Vanbever, R, et al., "Formulation and Physical Characterization of Large Porous Particles for Inhalation," Pharm. Res., 1999; 16(11):1735-1742.
Vervaet, C, et al, "Drug-Surfactant-Propellant Interactions in HFA-Formulations," Int. J. Pharm., 1999; 186:13-30.
Webb, SD, et al., "A New Mechanism for Decreasing Aggregation of Recombinant Human Interferon-g by a Surfactant: Slowed Dissolution of Lyophilized Formulations in a Solution Containing 0.03% Polysorbate 20," J. Pharm. Sci., 2002; 91(2):543-558.
Webb, SD, et al., "Surface Adsorption of Recombinant Human Interferon-g in Lyophilized and Spray-Lyophilized Formulations," J. Pharm. Sci., 2002; 91(6):1474-1487.
Williams, III, RO, et al., "Formulation of a Protein with Propellant HFA 134a for Aerosol Delivery," Eur. J. Pharm. Sci., 1998; 7:137-144.
Williams, III, RO, et al., "Influence of Metering Chamber Volume and Water Level on the Emitted Dose of a Suspension-Based pMDI Containing Propellant 134a," Pharm. Res., 1997; 14(4):438-443.
Williams, III, RO, et al., "Influence of Propellant Composition on Drug Delivery from a Pressurized Metered-Dose Inhaler," Drug Dev. Ind. Pharm., 1998; 24(8):763-770.
Wu, L, et al., "Molecular Scale Behavior in Alternative Propellant-Based Inhaler Formulations," in: A.J. Hickey (Ed), Inhalation Aerosols: Physical and Biological Basis for Therapy, 2007.
International Search Report and Written Opinion for PCT/US2009/034162 dated Sep. 22, 2009.
Williams, III, RO, et al., "Formulation of a protein with propellant HFA 134a for Aerosol Delivery," European Journal of Pharmaceutical Sciences, 1998; 137-144.
Bodhmage et al., "Correleation between physical properties and flowability indicators for fine powders", M.S. Thesis, Dept. Chem. Eng., Univ. Saskatchewan (2006).
Office Communication issued in U.S. Appl. No. 12/778,795, dated Apr. 11, 2017.
US Pharmacopeia Ch. 1174: Powder Flow (2004).
De Boer, A. H., et al. "Characterization of inhalation aerosols: a critical evaluation of cascade impactor analysis and laser diffraction technique." *International journal of pharmaceutics* 249.1-2 (2002): 219-231.
Labiris, N. R., and M. B. Dolovich. "Pulmonary drug delivery. Part I: physiological factors affecting therapeutic effectiveness of aerosolized medications." *British journal of clinical pharmacology* 56.6 (2003): 588-599.
Watts, "Pulmonary Delivery of Tacrolimus for Lung Transplant and Asthma Therapy," Ph.D. Dissertation, The University of Texas at Austin, 2009.
Sakagami, Masahiro. "In vivo, in vitro and ex vivo models to assess pulmonary absorption and disposition of inhaled therapeutics for systemic delivery." *Advanced drug delivery reviews* 58.9-10 (2006): 1030-1060.
"Breathing Problems: Using a Dry Powder Inhaler", downloaded from https://www.uiofmhealth.org/health-library/uz2083 on May 17, 2021.
"Floc", Definition of FLOC by Oxford Dictionary on Lexico.com, downloaded from https://www.lexico.com/en/definition/floc on May 17, 2021.
"Acros Organics Brij® 98 (Polyoxyethylene(20) oleyl ether)", downloaded from coleparmer.com on Jan. 9, 2024.
"Brij® 35", downloaded from sigmaaldrich.com/US/en/product/mm/801962 on Jan. 9, 2024.
"Brij™ 98, Thermo Scientific Chemicals", downloaded from thermofisher.com/order/catalog/product/347181000 on Jan. 9, 2024.
"Gelucire® 50/13", downloaded from gattefosse.com/pharmaceuticals/product-finder/gelucire-5013 on Jan. 9, 2024.
"Labrasol®", downloaded from gattefosse.com/pharmaceuticals/product-finder/labrasol on Jan. 9, 2024.
"Laureth-8", downloaded from atamanchemicals.com on Jan. 9, 2024.
"Laureth-9 (polidocanol)", downloaded from Drugs.com, dated Oct. 17, 2023.
"Poloxamer", downloaded from Wikipedia on Jan. 9, 2024.
"Sorbitan monooleate (span 80)", downloaded from contactdermatitisinstitute.com/sorbitan-monooleate-span-80.php on Jan. 9, 2024.
"Tocofersolan", downloaded from Wikipedia on Jan. 9, 2024.
"Tween® 80", downloaded from sigmaaldrich.com/US/en/product/sial/p1754 on Jan. 9, 2024.
Kim, Min-Soo, et al. "Enhanced bioavailability of sirolimus via preparation of solid dispersion nanoparticles using a supercritical antisolvent process." *International journal of nanomedicine* (2011): 2997-3009.
Obikili, Augusta, et al. "Improvement of aqueous solubility and dissolution kinetics of canrenone by solid dispersion in sucroester." *Drug Development and Industrial Pharmacy* 14.6 (1988): 791-803. Abstract Only.
Szüts, Angéla, and Piroska Szabó-Révész. "Sucrose esters as natural surfactants in drug delivery systems—A mini-review." *International Journal of Pharmaceutics* 433.1-2 (2012): 1-9.

\* cited by examiner

100% Itz URF in HFA 227

PSD not significantly affected by drug loading in HFA 227
Average D50 between 8.0 – 9.5 µm for both formulations 071706-1 - Surfactant free URF formulation sprayed into water pMDI formulation sprayed onto SEM slide Average D50 ~ 8.4 µm for particles without sonication and 3.0 µm for particles with sonication

*Figure 3*

TEM Images of URF Itz Aerosol from pMDI

*Figure 4*

100% Itz URF
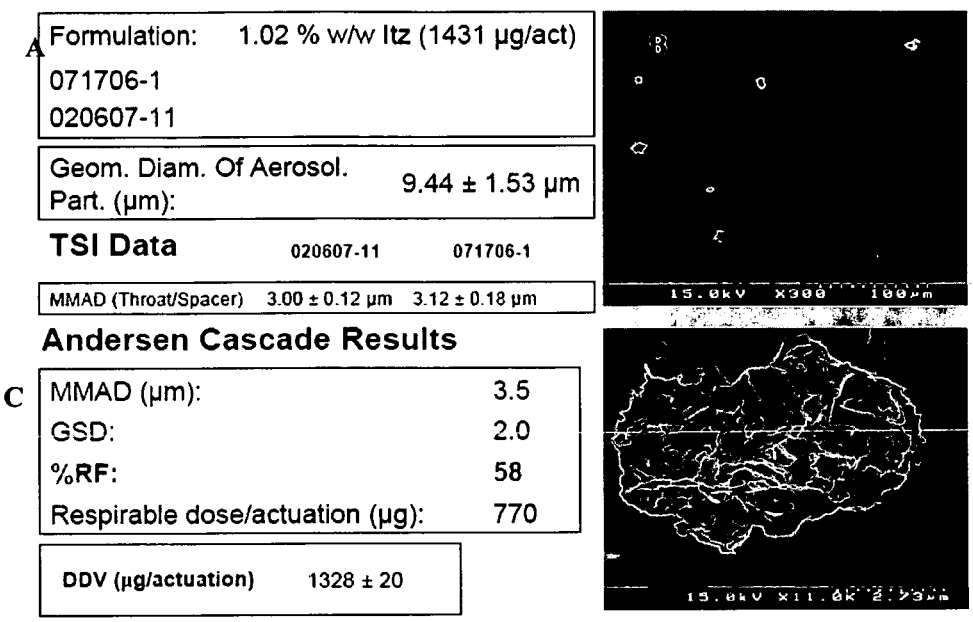
XRD of 100% Itz URF powder
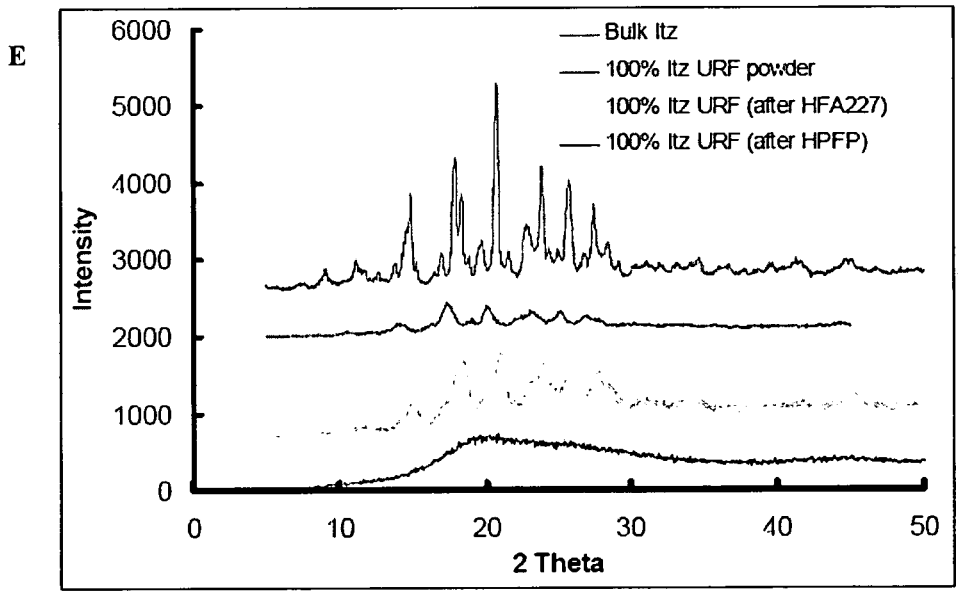
*Figure 5*

Dissolution of Particles Emitted by pMDI

Characterization of Charleston Sample (DOW Amorphous Itz)

BET Results : 8.69 +/- 0.574 m²/g correlates to diameter of 690 +/- ~45 nm

Extremely polydisperse

DOW Amorphous Itz (Charleston Sample)
SEM's from pMDI:
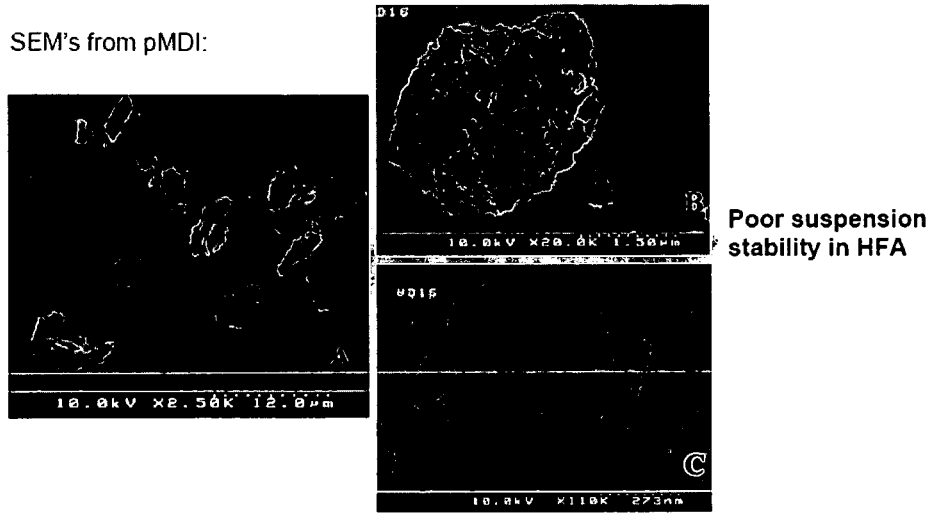
Poor suspension stability in HFA
*Figure 8*
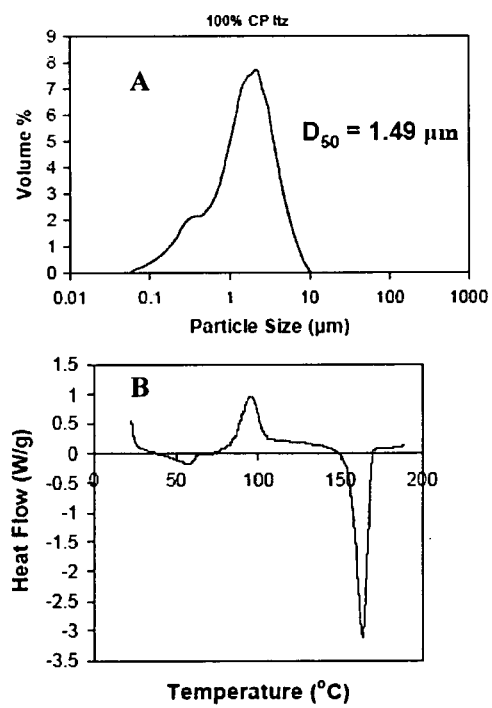
Characterization of 100% Itz made by CP
*Figure 9*

100% Itz - CP

SEM's from pMDI:

Moderately good suspension stability in HFA

Comparison of 100% Itz Formulations
| | Geometric Diameter (Malvern)(µm) | MMAD (µm) | $\rho_g$ (of aerosolized particle) (g/cc) | Susp. Stab. |
|---|---|---|---|---|
| 100% Itz TFF | 9.44 ± 1.53 | 3.5 | 0.16 | Excellent |
| 100% Itz CP | 9.88 ± 1.07 | --- | 0.16 | Moderate |
| 100% Itz DOW | 7.5 ± 0.1 | --- | 0.42 | Poor |
*Figure 11*

Aerosolized Particle Dimensions from Stage 3 of ACI

|  | Geometric Diameter (SEM)(μm) | MMAD (μm) | $\rho_g$ (of aerosolized particle) (g/cc) |
|---|---|---|---|
| 100% Itz TFF | 9.89 | 4 | 0.16 |
| 100% Itz CP | 10.10 | 4 | 0.16 |
| 100% Itz DOW | 6.19 | 4 | 0.42 |

*Figure 12*

Milled Itz Particles

Milled 300 nm Particles

*Figure 13*

Milled Particles Used as Controls

Milled 300 nm particles

Milled 3 μm particles after exposure to HFA 227 (dashed)

Milled 3 μm particles (solid)

*Figure 14*

Aerosolized Milled Particles

Milled 300 nm

Milled 3 μm

*Figure 15*

XRD of Milled Itz Particles

TFF Particles in HPFP

Small floc diameters from camera show are ~100-200 μm; Larger flocs have diameter ~400-700 μm

CP Itz in HPFP

Small floc diameters from camera show are 200-300 μm. Large floc diameters 600-800 μm

DOW Amorphous in HPFP

Floc diameters from camera show are ~100-150 μm

Comparison of All 100% Itz Formulations

| | Geometric Diameter (Malvern)(μm) | MMAD (μm) | $\rho_g$ (of aerosolized particle) (g/cc) | Susp. Stab. |
|---|---|---|---|---|
| 100% Itz TFF | 9.44 ± 1.53 | 3.5 | 0.16 | Excellent |
| 100% Itz CP | 9.88 ± 1.07 | --- | 0.16 | Moderate |
| 100% Itz DOW | 7.5 ± 0.1 | --- | 0.42 | Poor |
| 300 nm Milled | --- | --- | 1.02 | Poor |
| 3 μm Milled | 5.44 ± 0.4 | 4.01 | 0.46 | Poor |

*Figure 22*

Aerosolized Particle Dimensions from Stage 3 of ACI

| | Geometric Diameter (SEM)(μm) | MMAD (μm) | $\rho_g$ (of aerosolized particle) (g/cc) |
|---|---|---|---|
| 100% Itz TFF | 9.89 | 4 | 0.16 |
| 100% Itz CP | 10.10 | 4 | 0.16 |
| 100% Itz DOW | 6.19 | 4 | 0.42 |
| 300 nm Milled | 3.95 | 4 | 1.02 |
| 3 μm Milled | 5.91 | 4 | 0.46 |

*Figure 23*

Experimental $\varphi_g$ Gives Reasonable Value for HFA Droplet Diameter $$\varphi_k = \frac{\varphi}{\varphi_f}$$

$$\varphi_k \sim \left(\frac{d_f}{d}\right)^{D_f - 3}$$

$$\varphi_f = 0.74$$

$\Phi = (mass_{Itz}/\rho_{Itz})/vol_{HFA}$
$= 0.0077$
$d_f = 100\ \mu m$
$d = 0.44\ \mu m$

→

$\Phi_k \sim 0.0101$
$D_f \sim 2.15$

*Figure 25*

$$\varphi_k = \left(\frac{d_f}{d}\right)^{D_f-3}$$

$$U = \left(\frac{V_A}{A_A C_D} \frac{2g(\rho_p - \rho_l)k_c}{\rho_l}\right)^{0.5} \log\left(\frac{d_f}{d}\right)^{(D_f-3)/2}$$

|  | $D_f$ | $U_{floc}$ (mm/s) | $U_{Stokes}$ (mm/s) |
|---|---|---|---|
| Milled 300 nm Itz Particles | 2.9 | 1.38 | $3.5*10^{-5}$ |
| Milled 3 μm Itz Particles | 2.5 | 0.33 | $2.0*10^{-3}$ |
| TFF Itz Particles | 2.15 | 0.024 | $4.1*10^{-5}$ |

TFF Particles in HPFP

CP Itz in HPFP

DOW Amorphous in HPFP 300 nm Milled Itz in HPFP

*Figure 30*

3 μm Milled Itz in HPFP

*Figure 31* suspensions in HFA 227

| Formulation | DDV (μg) | %Theoretical DDV | FPF (%) | Fine Particle Dose/Actuation (μg) | ED (μg) |
|---|---|---|---|---|---|
| TFF BSA | 915 ± 21 | 92 | 47 ± 4.0 | 318 ± 31 | 695 ± 133 |
| TFF BSA Tween 20 | 826 ± 58 | 83 | 43 ± 4.2 | 292 ± 16 | 690 ± 71 |
| TFF BSA:Tre 1:1 Tween 20 | 452 ± 54 | 90 | 38 ± 2.1 | 132 ± 19 | 350 ± 56 |
| TFF BSA unsonicated | 625 ± 95 | 63 | – | – | – |
| Milled BSA | 295 ± 17 | 30 | – | – | – |
| Spray Dried BSA | 308 ± 38 | 31 | – | – | – |

*Figure 43*

| Formulation | ACI MMAD (μm) | ACI GSD | APS MMAD (μm) | APS GSD | d(v,50) Particle Diameter (μm) | SEM Particle Diameter (μm) | $\rho_H$ (g/cm³) |
|---|---|---|---|---|---|---|---|
| BSA | 3.1 ± 0.1 | 1.9 ± 0.1 | 3.2 ± 0.03 | 1.6 ± 0.01 | 9.1 ± 0.9 | 9.4 | 0.19 |
| BSA Tween 20 | 3.6 ± 0.1 | 1.9 ± 0.2 | – | – | 9.9 ± 0.8 | 9.3 | – |
| BSA:Tre 1:1 Tween 20 | 3.2 ± 0.2 | 1.8 ± 0.1 | 4.0 ± 0.15 | 1.7 ± 0.01 | 7.3 ± 0.5 | 7.4 | – |

*Figure 44*

| Particle Type | Particle Diameter (μm) | Hamaker Constant $10^{21} \times A_{131}$ (J) | Separation Distance (nm) at $\Phi_{vdw} = 3/2 k_B T$ |
|---|---|---|---|
| Spray Dried-Non-Porous | 5.0 | 14 | 270 |
| Spray Dried-Porous $\phi = 0.5$ | 5.0 | 3.8 | 100 |
| Spray Dried-Hollow Sphere* $\phi = 0.12$ | 5.0 | 14 | 120 |
| TFF Nanorods[a] | 0.33 | 14 | 23 |
| TFF Nanorods[b] | 0.33 | 2.6 | 6.9 |

*Figure 45*

| Particle Type | $d_p$ (μm) | $d^{aer}$ (μm) | $(\rho_L-\rho_i)$ (g/cm³) | $U_f$ (mm/s) | $U_p$ (mm/s) | $\dot{\phi}_r$ | $\phi^{£act}$ | $\phi_r$ | $D_f$ |
|---|---|---|---|---|---|---|---|---|---|
| TFF | 0.33ª | 250 | 0.00022 | 0.023 | 2.4 x 10⁻⁵ | 0.00077 | 0.38 | 0.0020 | 2.4 |
| Milled | 0.41 | 100 | 0.0080ᵇ | 0.13 | 3.7 x 10⁻⁵ | 0.0067 | 0.11 | 0.073 | 2.5 |
| Spray Dried | 6.3 | 100 | 0.040 | 0.80 | 8.8 x 10⁻³ | 0.0077 | 0.021 | 0.36 | 2.6 |
| Spray Dried-Hollow Sphere | 5.0ᶜ | -- | 0.013ᵈ | -- | 6.4 x 10⁻⁴ | -- | -- | -- | -- |
*Figure 46*
*Figure 47*
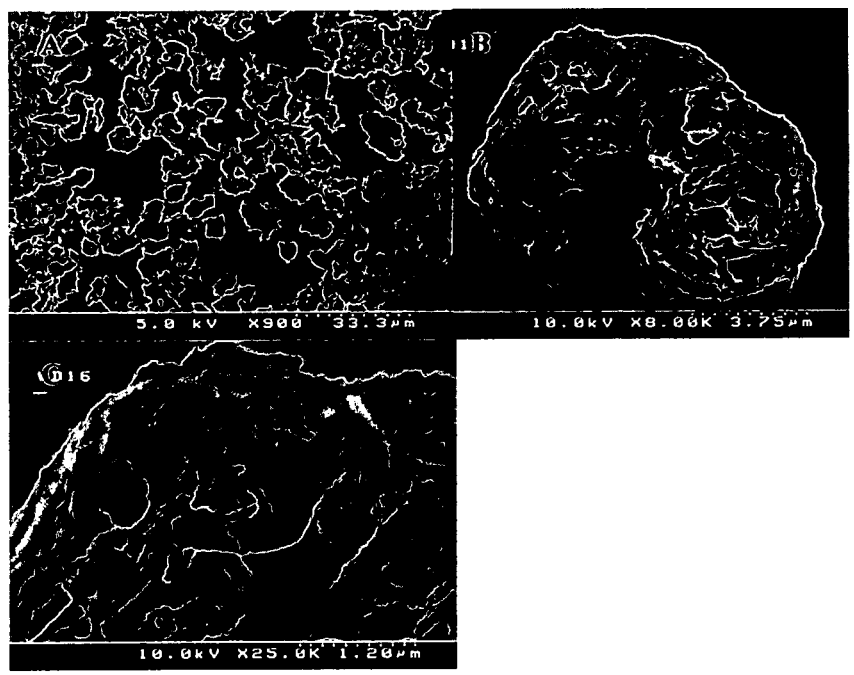
*Figure 48*

| TFF ITZ powder before HFA exposure | TFF ITZ powder after HFA exposure | TFF ITZ pMDI after actuation into water (no exposure to air) |

Aerosol TFF Itz

Aerosol TFF Itz sprayed into dissolution media
t = 1 min

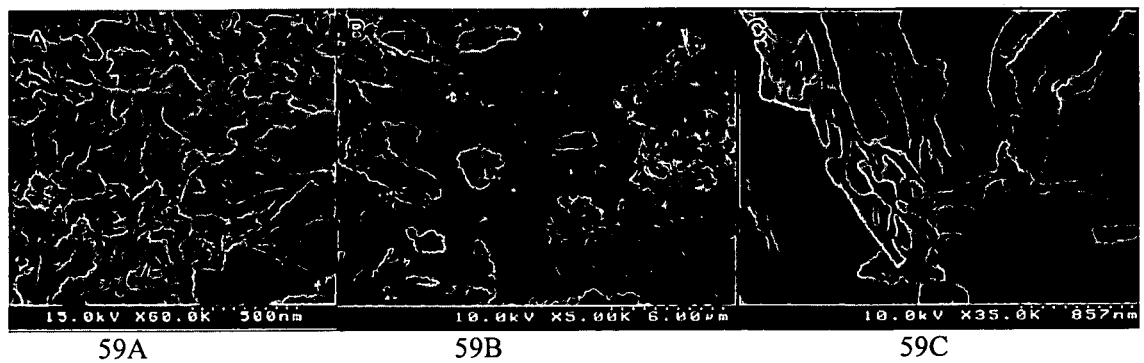
FIGURE 59 A-C

TEMPLATED OPEN FLOCS OF ANISOTROPIC PARTICLES FOR ENHANCED PULMONARY DELIVERY

CROSS-REFERENCE TO RELATED APPLICATIONS

This application claims benefit of U.S. Provisional application Ser. No. 61/028,218, filed Feb. 13, 2008, which is incorporated herein by reference in its entirety.

STATEMENT OF FEDERALLY FUNDED RESEARCH

This invention was made with U.S. Government support under Contract No. CHE9876674 awarded by the National Science Foundation. The government has certain rights in this invention.

TECHNICAL FIELD OF THE INVENTION

The present invention relates in general to the field of poorly water soluble compositions and more particular to composition for deep lung delivery.

BACKGROUND OF THE INVENTION

Without limiting the scope of the invention, its background is described in connection with medicinal formulations and compositions for use in pressurized metered dose inhalers. Current methods of delivery have produced few examples of suspensions with 1-5% (w/w) mass loadings in HFAs that are stable against settling on time scales of over 60 seconds. As the mass loading increases up to and above 5% (w/w), particles often aggregate within aerosolized droplets leading to substantial increases in $d_a$ and thus reduction in fine particle fraction (FPF).

For example, U.S. Pat. No. 6,585,957 relates to medicinal aerosol formulations. The formulation includes a protein or peptide medicament, a fluid carrier for containing said medicament; and a stabilizer selected from an amino acid, a derivative thereof or a mixture of the foregoing. Similarly, U.S. Pat. No. 6,655,381 relates to pre-metered dose magazine for breath-actuated dry powder inhaler. More specifically, a pre-metered dose assembly for consistently supplying precise doses of medicament is taught for a breath-actuated dry powder inhaler. The breath-actuated dry powder inhaler including the pre-metered dose assembly in combination with a de-agglomerator for breaking up aggregates and micronizing particles of dry powder prior to inhalation of the powder by a patient.

U.S. Pat. No. 7,011,818 relates to carrier particles for use in dry powder inhalers. The powder includes additive material on the surfaces of the carrier particles to promote the release of the active particles from the carrier particles on actuation of the inhaler. The powder is such that the active particles are not liable to be release from the carrier particles before actuation of the inhaler. The inclusion of additive material (4) in the powder has been found to give an increased respirable fraction of the active material The general method of delivery of drugs to the lungs for the treatment of numerous pulmonary disorders is through inhalation of the drug particles. The drug particles are generally in the form of an aerosol of respirable sized particles incorporated into a colloidal dispersion containing either a propellant, as a pressurized metered dose inhaler (pMDI) or air such as is the case with a dry powder inhaler (DPI).

It is of the upmost importance in the aerosol formulation that the composition is stable and the dose discharged from the metered dose valve is reproducible; however, there are numerous factors that influence these features, e.g., creaming, or settling, after agitation are common sources of dose irreproducibility in suspension formulations. Another concern is the flocculation of the composition after agitation. This flocculation often results in dose irreproducibility and as such, it is an undesirable process and composition and is often seen in aerosol formulations containing only medicament and propellant or formulation contains small amounts of surfactants. Surfactants are often included in the formulations to serve as suspending aids to stabilize the suspension or lubricants to reduce valve sticking which also causes dose irreproducibility.

In addition, the drug absorption into the subject from the airway dependents on numerous factors, e.g., the composition of the formulation, type of solute, the method of drug delivery, and the site of deposition. Therefore, formulation and device characteristics have a dramatic impact upon the rate and extent of peptide absorption from the lung. Dry powder presentations of peptide and protein drugs possess unique opportunities in formulations, which do not occur in liquid presentations such as pMDIs and nebulized solutions.

One method commonly used to prepare medicament particles for drug formulations into fine powder is spray drying. Spray drying forms spherical particles that are often hollow thus resulting in a powder with low bulk density compared to the initial material, other characteristics include particle size distribution, bulk density, porosity, moisture content, dispersibility, etc. In addition, the spray dried particles demonstrate poor flow characteristics. The spray drying process requires heating of the formulation making it drying less desirable for heat sensitive compounds such as peptide and protein drugs. For these reasons spray dried particles often suffer from adhesion and poor flowability to the extent that dose accuracy becomes a problem.

SUMMARY OF THE INVENTION

The present invention provides for the dispensing of poorly water soluble compositions and/or protein via pMDI. As stated previously, sub-micron particles are desirable for drug delivery because smaller particles provide a larger surface area/mass ratio for dissolution. Milling is a common particle size reduction method; however, the milling process has been shown to produce partially amorphous drug domains. Although amorphous particles may be desirable for certain applications (e.g., to raise solubility for enhanced bioavailability), they are equally undesirable in many applications (e.g., the drug nanoparticles may crystallize upon storage). Thus the inventors recognized that it is important to find ways to make crystalline nanocrystals without the need to use milling.

The present inventors found that hydrofluroalkane solvents may be used to crystallize amorphous nanoparticles. Amorphous nanoparticles crystallize in the presence of the hydrofluoroalkane for the drug itraconazole. Furthermore, the size of the particles remains very small during the crystallization process, with the particle dimensions below about 1 μm. The crystalline particles are of interest for pMDI delivery as well as other applications.

The present inventors recognized that the production of protein particles with the optimal $d_a$ for deep lung delivery (i.e., over about 90% yield) and high stability against aggregation at the particle and the molecular level remains a significant challenge.

The present invention includes a medicinal formulation for use in a pressurized metered dose inhaler. The formulation includes a space filled flocculated suspension having one or more flocculated particles of one or more active agents and a hydrofluoroalkane propellant. A portion of the one or more flocculated particles is templated by the formation of hydrofluoroalkane droplets upon atomization. The templated floc compacts upon the evaporation of the hydrofluoroalkane propellant to form a porous particle for deep lung delivery.

The present invention also provides a method of making a medicinal aerosol composition for a pressurized metered dose inhaler forming a space filled flocculated suspension comprising one or more flocculated particles of one or more active agents and a hydrofluoroalkane propellant and templating at least a portion of the one or more flocculated particles by the formation of hydrofluoroalkane droplets upon atomization. The templated floc is compacted by the evaporation of the hydrofluoroalkane propellant to form a porous particle for deep lung delivery.

The present invention also provides a medicinal porous formulation for deep lung delivery by a pressurized metered dose inhaler. The therapeutically effective porous particle includes one or more at least partially compacted templated flocculated active agents for deep lung delivery. The therapeutically effective porous particle is formed by atomization of a space filled flocculated suspension. The space filled flocculated suspension includes one or more flocculated particles of one or more active agents and a hydrofluoroalkane propellant into a templated flocculated particle. Upon the evaporation of the hydrofluoroalkane propellant the porous particle shrinks for deep lung delivery.

The present invention provides compositions and method for forming stable suspensions of open flocs of rod shaped particles and templating and shrinking the flocs to produce particles for efficient pMDI deep lung delivery. This can be used in conjunction with a wide variety of drugs without the need for surfactants or co-solvents to stabilize the primary particles.

The present invention provides for the formation of stable suspensions of very low density flocs of rod-shaped drugs in hydrofluoroalkane propellants for pressurized meter dose inhalers (pMDI) and for templating the flocs to achieve high fine particle fractions in pulmonary delivery.

BRIEF DESCRIPTION OF THE DRAWINGS

For a more complete understanding of the features and advantages of the present invention, reference is now made to the detailed description of the invention along with the accompanying figures and in which:

FIGS. 3A and 3B are SEM images of pMDI formulation, while 3C and 3D are the corresponding graphs of particle size;

FIGS. 4A-4B are TEM images of URF Itz aerosol from pMDI;

FIGS. 5A and 5C are data for the 100% Itz URF samples shown in the SEM images FIGS. 5B and 5D;

FIG. 5E is a XRD of URF Itz powder;

FIGS. 8A-8C are SEM images of Charleston sample Dow amorphous Itz from pMDI;

FIGS. 9A-9B are graphs and 9C is a SEM characterizing the Itz sample made by CP;

FIG. 11 is a table comparing Itz formulations;

FIG. 12 is a table comparing particle dimensions of ACI;

FIGS. 13A-13C are SEM images of milled Itz particles;

FIG. 14 is a graph of the milled control particles;

FIGS. 15A-15D are SEM images of milled aerosolized milled particles;

FIG. 22 is a table comparing Itz formulations;

FIG. 23 is a table comparing aerosolized particle dimensions of ACI;

FIG. 25 is an illustration of the calculation of Df;

FIG. 30 is a SEM image of milled Itz in HPFP;

FIG. 31 is a SEM image of milled Itz in HPFP;

FIG. 43 is a table of the dosage and aerodynamic properties of TFF, milled, and spray dried particle suspensions in HFA 227;

FIG. 44 is a table of the aerodynamic particle sizes determined by ACI and APS and geometric particle sizes determined by laser diffraction and SEM;

FIG. 45 is a table of the calculation of the van der Waals (VdW) interaction potential Φvdw of BSA particles in HFA 227;

FIG. 46 is a table of the settling behavior of BSA particles prepared by TFF, milling, and spray drying and calculations for porous shell particles prepared by spray drying, with the aValue determined from the equivalent volume of a sphere measured from laser light scattering; bThe density difference was determined by $\rho f-\rho L$ with $\rho p=1.5$ g/cm3; cDetermined from dimensions given by Dellamary et al.; dCalculated for primary particle with 100 nm thick shell;

FIG. 47 is an optical image of protein pMDI formulations (Lys in HFA 227 with a drug loading of 20 mg/mL, Lys in HFA 134a with a drug loading of 40 mg/mL, 50 mg/mL, 90 mg/mL, and BSA (BSA) in HFA 227 with a drug loading of 50 mg/mL, left to right) 4 hours after shaking;

FIG. 48 is a SEM micrographs of aerosolized Lys particles (Lys in HFA 134a pMDI loaded at 50 mg/mL). Aerosolized particles have geometric diameters between 8-10 μm (A) and exhibit porous morphology (B) and (C);

FIGS. 55A and 55B are scanning electron microscopy images of aerosolized TFF ITZ (FIG. 55A) and aerosolized TFF ITZ in dissolution media at 37° C. after t=1 minute (FIG. 55B) dissolution media comprised phosphate buffer (pH=7.4) containing 0.2 w/v SDS;

FIG. 56 is the dissolution study graph comparing the dissolution profiles of aerosolized TFF ITZ and aerosolized milled ITZ particles (300 nm) studied in phosphate buffer (pH=7.4) containing 0.2 w/v SDS at 37° C.;

FIG. 57 is a graph of the aerodynamic diameters of milled, TFF, and CP drug compositions measured by the APS 3321/3343 and the Aerosizer/Aerodisperser systems;

FIG. 58 is a graph of the aerodynamic particle size distribution for the TFF lys composition; and FIGS. 59A-59C are SEM micrographs of (FIG. 59A) TFF lys nanorods prior to aerosolization and (FIG. 59B) after aerosolization and FIG. 59C is an image at higher magnification of aerosolized TFF lys particles.

DETAILED DESCRIPTION OF THE INVENTION

Figure 1:
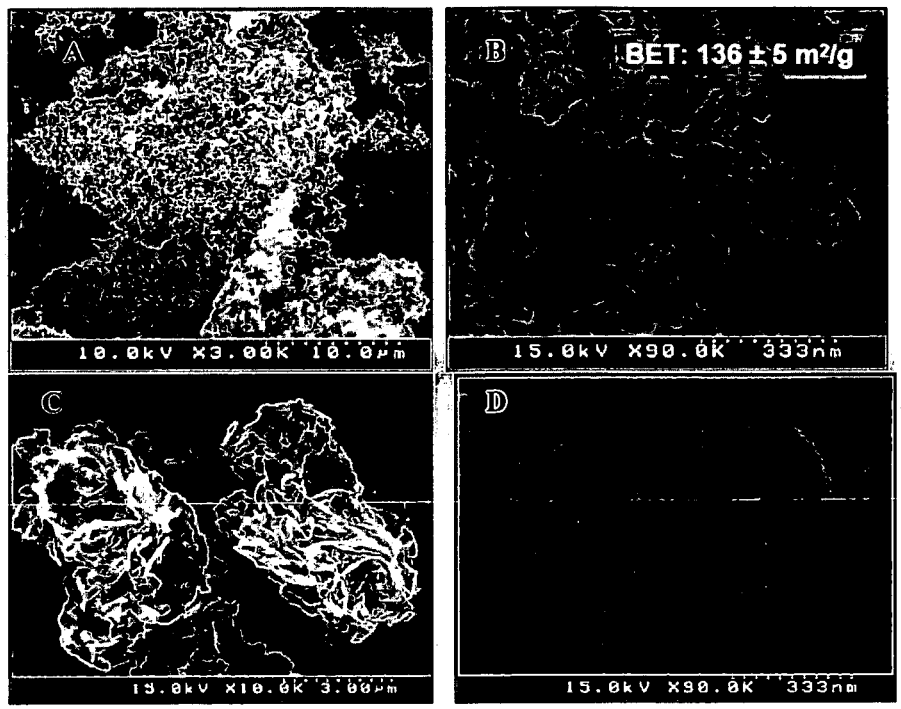
FIGS. 1A-1D are SEM images of URF particles from surfactant free formulations.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

The present inventors recognized that the delivery of protein therapeutics has been largely limited to parenteral delivery due to the chemical and physical instabilities of proteins and challenges in permeating biological membranes. The present inventors also recognized that pulmonary delivery is non-invasive routes offers advantages of large alveolar surface area (about 100 m$^2$), rapid absorption across the thin alveolar epithelium (between about 0.1 and about 0.5 μm), avoidance of first pass metabolism, and sufficient bioavailabilities.

For pulmonary delivery, pressurized meter dose inhalers (pMDI) remain the most popular delivery device, relative to dry powder inhalers (DPI) and nebulizers, because of low cost, portability, and disposability. Because most drugs, including proteins, are insoluble in hydrofluoroalkane (HFA) propellants, most effort has focused on the design of stable suspensions. The lack of understanding of how to form these stable suspensions has limited the development of viable formulations. Although certain proteins in suspensions may potentially be natured by HFAs, the low degree of contact in the solid state with the solvent, relative to solutions, is highly beneficial in some instances, e.g., insulin, lysozyme, catalase and rhDNase I.

To achieve high deposition of aerosolized particles in the deep lung, the aerodynamic diameter (da) should range between about 1-5 μm. Such protein particles may be produced by milling, spray drying, and spray freeze-drying (SFD). Milling processes can generate significant amounts of heat on localized areas of the protein particle which can lead to denaturation. In spray drying and SFD processes, proteins may adsorb and subsequently denature and aggregate at the large gas-liquid interface created upon atomization of droplets on the order of about 10-100 μm, although this effect may be mitigated with interfacially active excipients. Limited process yields, in terms of weight of protein, for spray drying (about 50-70%) and SFD (about 80%) are a major concern for highly valuable proteins.

The present inventors recognized that methods and devices currently used in the art have a significant challenge in producing protein particles with over about 90% yield, the optimal $d_a$ for deep lung delivery, and high stability against aggregation. In fact, there have been few suspensions in the art that provide a 1-5% (w/w) mass loadings in HFAs and are stable against settling on time scales of over 60 seconds. As the mass loading increases up to and above 5% (w/w), particles often aggregate within aerosolized droplets leading to substantial increases in $d_a$ and thus reduction in fine particle fraction (FPF).

Flocculation and settling can lead to irreversible particle aggregation as well as variable dosing between actuations. For example, suspensions of spherical particles formed by milling or spray drying often flocculate and settle in less than 60 seconds. Consequently, the efficiency of pMDIs is often limited for suspensions of proteins, as well as low molecular weight drugs, with typical FPFs between about 5-30%. Although surfactants and co-solvents, such as ethanol, could potentially stabilize the suspension, the surfactants currently approved by the FDA for inhalation are insoluble in HFAs. Even for soluble surfactants, the surfactant tails are often not solvated well enough by HFAs, which have low polarizabilities and van der Waals forces, to provide steric stabilization. Thus, the present inventors have developed a new surfactant structures by achieving a fundamental understanding of the molecular interactions with atomic force microscopy and theory. The present inventors have also developed a method to minimize the use of co-solvents that can chemically destabilize drugs and modify protein conformation.

An alternative approach is to modify the particle morphology to enhance the colloidal stability of the primary particles. Large porous particles or hollow particles with porous or nonporous shells formed by spray drying were stable against settling for at least about 4 hours when suspended in HFAs. Respirable fractions were as high as 68%. Here, the presence of pores filled with HFA decreases the density difference of the particle with the surrounding HFA media and reduces van der Waals attractive forces between particles. Additional reports of settling rates, primary particle aggregation, and changes in fine particle fraction, especially after storage, will be beneficial for further understanding this approach. Recently, large porous nanoparticle (LPNP) aggregates, with $d_a$ optimized for dry powder inhaler (DPI) pulmonary delivery, have been formed by spray drying of aqueous suspensions of submicron particles.

Upon contact with lung tissue, these particles break up into nanoparticles to facilitate dissolution and absorption. To extend this approach to delivery with a pMDI, each LPNP can be stabilized as an individual entity in a colloidal dispersion as shown in FIG. 1, if the LPNPs do not aggregate and settle. An alternative approach for efficient nanoparticle delivery to the deep lung is to nebuilize nanoparticle dispersions in aqueous media.

Spray freezing into liquids (SFL), and thin film freezing (TFF), have been shown to produce high surface area, stable rod-like particles with about 50-100 nm diameters and high aspect ratios, despite slower cooling rates than in SFD. The stability of lactase dehydrogenase, based on enzymatic activity, was increased in these processes relative to SFD. This increase was achieved by lowering the area of the gas-liquid interface, which has been shown to denature proteins.

The present invention provides a method of forming suspensions against settling stable of BSA particles in HFA 227 without stabilizing surfactants or co-solvents in order to achieve high fine particle fractions in pMDI delivery. In stark contrast to the methods currently used in the prior art, the present invention provides a method of purposely flocculate the particles in the HFA to prevent settling (i.e., the opposite of the prior art). Spheres, produced by milling or spray drying, were added to HFA 227, but they produced dense flocs that settled rapidly. Asymmetric particles, such as rods, may be expected to pack less efficiently to form much lower density flocs with greater free volume than spheres. Rods were produced by TFF.

FIGS. 1A-1D are SEM images of URF particles from surfactant free formulations. The present invention provides very light open flocs in an HFA that occupy the entire vial and stack upon each other to prevent settling for months, as illustrated in FIG. 1. The morphology was determined by SEM of the original particles and after solvent removal of particles suspended and sonicated in acetonitrile or HFA 227. The flocculation is reversible, in that the flocs break up into submicron primary rod particles upon transfer to a more polar solvent acetonitrile. The particles were also studied in 2H,3H perfluoropentane (HPFP), a non-volatile surrogate for HFA 227, to analyze floc size by optical microscopy and static light scattering. The $d_a$ values were determined with an Andersen cascade impactor (ACI) and aerodynamic particle sizer (APS) and $d_g$ values with static light scattering and SEM micrographs. The emitted HFA droplets, on the order of about 25 µm, were utilized to break apart and template the highly open flocs as seen in FIG. 1. Upon evaporation of the HFA, the shrinkage of the flocs from capillary forces produces smaller and denser porous particles with desirable $d_a$.

The particle volume fractions and fractal dimensions for flocs composed of either cylindrical (rods) or spherical primary particles have been characterized. Calculations of van der Waals energies between suspended particles are presented to explain floc formation and break up of the floc into subdomains upon templating the flocs with the HFA droplets. The particle shrinkage during HFA evaporation leads to the final aerosolized particle size and porosity as explained with a material balance. The present invention provides a novel approach of flocculating, templating, and shrinking the particles results in proper $d_a$ with low polydispersities without surfactants or co-solvents. Thus, the present invention circumvents the classical paradigm of attempting to stabilize colloidal dispersions of preformed primary particles with surfactants. The flocculation for achieving stable suspensions and high fine particles fractions without the need for surfactants of the present invention is of practical interest for wide classes of low and high molecular weight pharmaceuticals and biopharmaceuticals that can be formed into nanorods.

Dry powder inhalers may use the flocs of asymmetric particles for dose delivery. Currently dry powder inhalers do not use flocs of asymmetric particles with high aspect ratios. The flocs can break up more easily under the influence of the shear forces in the dry powder inhaler than more dense particles with lower aspect ratios. The break up of the flocs will produce smaller flocs composed of particles with appropriate aerodynamic diameters for deep lung delivery. Currently, the efficiency of delivery by dry powder inhalers can be limited by the inability of the air to break up the particles. Furthermore, small high aspect ratio primary particles that reach the deep lung will have higher dissolution rates, as a consequence of higher surface areas. Most of the benefits described for therapy with flocs composed of anisotropic particles described in this application will also be present for delivery with dry powder inhalers. The particle may be loaded into the dry powder inhaler by a variety of methods. They may be compacted into blister packs in the solid state. They may also be loaded as colloidal suspensions in a solvent, where the solvent is a liquid, compressed gas, for example a hydrofluoralkane. The evaporation of the solvent may be used to compact the flocs to raise the final particle density in the dry powder inhaler. In addition, the flocs may be formed directly in a component of the dry powder inhale device by thin film freezing. As described above for PMDIs, this approach does not use particles that are pre-formed to design the aerodynamic diameter of the aerosol particle. Instead, the aerodynamic diameter is generated in the air ways by the shear forces upon rupture of the flocs. This aerodynamic diameter is not present in the starting flocs. Thus, the present invention circumvents the classical paradigm of attempting to design the aerodynamic diameters of pre-formed individual particles prior to loading into the dpi.

Bovine serum albumin (BSA), trehalose, and polyoxyethylene sorbitan monolaurate (Tween 20) were purchased from Sigma (St. Louis, MO). The propellant 1,1,1,2,3,3,3-heptafluoroprane (HFA 227) was purchased from Hoechst (Frankfurt, Germany) and 2H,3H-Perfluoropentane (HPFP) was purchased from SynQuest Labs Inc. (Alachua, FL). The Micro BCA Protein Assay Reagent Kit was obtained from Pierce (Rockford, IL). The water was deionized by flowing distilled water through a series of 2×7 L mixed bed vessels (Water and Power Technologies, Salt Lake City, UT) containing 60:40 anionic:cationic resin blends.

BSA powders were prepared by the thin film freezing (TFF) process described previously. Briefly, 5 mg/mL feed solution of BSA in 10 mM pH=7.4 potassium phosphate buffer was passed at a flow rate of 4 mL/min through a 17 gauge (e.g., 1.1 mm ID, 1.5 mm OD) stainless steel syringe needle. The droplets fell from a height of 10 cm above a rotating stainless steel drum (12 rpm) 17 cm long and 12 cm in diameter. The hollow stainless steel drum was filled with dry ice to maintain a drum surface temperature of 223 K. On impact, the droplets deformed into thin films and froze. The frozen thin films were removed from the drum by a stainless steel blade and transferred to a 400 mL PYREX® beaker filled with liquid nitrogen. The excess liquid nitrogen was evaporated in a −80° C. freezer.

A Virtis Advantage Lyophilizer (The Virtis Company, Inc., Gardiner, NY) was used to dry the frozen slurries. Primary drying was carried out at −40° C. for 36 hrs at 300 mTorr and secondary drying at 25° C. for 24 hrs at 100 mTorr. A 12 hour linear ramp of the shelf temperature from −40° C. to +25° C. was used at 100 mTorr.

Spray drying was performed with a Buchi Model 190 mini spray dryer (Brinkmann, Westbury, NY). A 10 mg/mL BSA feed solution in 10 mM potassium phosphate buffer (pH=7.4) was atomized using a 0.5 mm ID two fluid nozzle with an atomizing air flow rate of 200 mL/s. The liquid protein formulation was pumped through the nozzle by a peristaltic pump (VWR, Bridgeport, NJ) at a flow rate of 5 mL/min using 5 mm ID silicone tubing. The inlet temperature for the heated aspirator air was set to 150° C. at a flow rate of 1000 L/hr. The resulting outlet temperature from the above conditions was 80° C.

Bulk BSA powder as received was suspended at 5 mg/mL in acetonitrile. The BSA suspension was placed in a mill filled with 50 ceramic balls approximately 1 cm in diameter and milled on a mechanical roller for 24 hours. The milled BSA suspension was dried in the Virtis Advantage Lyophilizer at a shelf temperature of 30° C. for 12 hours at 1000 mTorr.

Dry powders were placed in 60 mL glass bottles (Qorpak, Bridgeville, PA) and pre-cooled in a −80° C. freezer. HFA 227 was also pre-cooled in a −80° C. freezer and poured into the bottles containing the protein powders to form 0.7% (w/w) suspensions. The bottles were packed in dry ice and the suspensions were then sonicated for 2 minutes using a Branson Sonifier 450 (Branson Ultrasonics Corporation, Danbury, CT) with a 102 converter and tip operated in pulse mode at 35 watts. Approximately 5 mL aliquots of the suspension were then dispensed into a 500 mL acetonitrile bath for particle size analysis by static light scattering with a Malvern Mastersizer-S (Malvern Instruments, Ltd., Worcestershire, UK). Typical obscuration values ranged from about 11 to about 13%. Next, 10 mL of the cooled protein formulations were dispensed into 17 mL glass pMDI aerosol vials (SGD, Paris, France) and fitted with metering valves containing 100 μL metering chambers (DF10 RC 150, Valois of America, Inc., Congers, NY). The vials were then allowed to warm up to room temperature.

The dried powders were also suspended in acetonitrile at a concentration of 5 mg/mL and sonicated for about 2-3 minutes in the same manner described above. Approximately 2 mL of the sonicated suspension was dispersed into a 500 mL acetonitrile bath and the particle sizes were analyzed by static light scattering.

The amount of BSA was measured using the Micro BCA Protein Assay following protocols provided by Pierce (Rockford, IL). Each sample was measured in triplicate with relative standard deviations (% RSD)<2%. The absorbance of the solutions was measured at 562 nm in a 96 well plate spectrophotometer (μQuant Model MQX200; Biotek Instruments Inc., Winooski, VT). Untreated BSA was used to prepare the protein standards at concentrations between about 2 and 30 μg/mL.

The protein suspensions in HFA were actuated once through the firing adaptor of a dosage unit sample tube (26.6 mm ID×37.7 mm OD×103.2 mm length; 50 mL volume; Jade Corporation, Huntingdon, PA). The firing adaptor was removed, and 40 mL of DI water was added to dissolve the protein. The sampling tube was shaken and allowed to sit for at least 30 min. to assure that the protein was dissolved in water. The protein concentration was determined using the Micro BCA protein assay in conjunction with the μQuant spectrophotometer. The glass vial containing the HFA protein suspension was weighed before and after each actuation to assure that the proper dose had been released. The measurement was repeated 3 times to get an average dose delivered through the valve (DDV) for each formulation.

To characterize the aerodynamic properties of the particles, an eight-stage Andersen cascade impactor (ACI) (Thermo-Andersen, Smyrna, GA) with an attached 15 cm spacer and an air flow-rate of about 28.3 L/min was used to quantify mass median aerodynamic diameter (MMAD), geometric standard deviation (GSD), fine particle fraction (FPF), and emitted dose (ED). Initially 3 shots were sent to waste, and the next 5 shots were made into the ACI. The interval between shots was between about 15-30 seconds to prevent cooling of the metering chamber and subsequent moisture condensation. After the last dose was discharged, the glass vial was removed from the impactor and the valve stem and actuator were rinsed separately with a known volume of DI water. Each plate of the impactor was placed in a separate container with a known volume of DI water and soaked for 30 minutes to assure complete dissolution. The protein concentrations were then measured with the Micro BCA Protein Assay.

The $d_a$ of the protein particles were also determined in triplicate with an Aerodynamic Particle Sizer (APS) 3321 (TSI, Shoreview, MN). The throat and spacer from the ACI were placed over the inlet of the APS and the airflow rate through the inlet was 5 L/min. Each formulation was shot once through the spacer and throat. The particle size range by mass was determined with the Aerosol Instrument Manager (AIM) software provided by TSI.

To obtain aerosolized particles for scanning electron microscopy (SEM) (Hitachi Model S-4500, Hitachi Ltd, Tokyo, Japan) analysis, double carbon adhesive tape was applied to stage 3 of the ACI. Each formulation was actuated once through the ACI with an air flow rate of 28.3 L/min. The carbon tape was removed from stage 3 and applied to an aluminum SEM stage, which was transferred rapidly to a Pelco Model 3 sputter-coater to minimize exposure to moisture. Total exposure to the atmosphere was less than 1 minute. The SEM micrographs were then characterized with imaging software (Scion, Frederick, MD) to determine the particle size distribution of at least 100 particles.

The aerosolized particles were also characterized by static light scattering. Each formulation was actuated once through the ACI spacer and throat. The aerosol exited the outlet of the throat downwards 5 cm directly above the laser beam of the Malvern Mastersizer S. For each formulation 100 measurements of the aerosolized spray were made every 5 ms. The recorded measurements were then averaged to give the final profile of the aerosolized particles on a volume basis.

Moisture contents in the vials of each formulation were tested with an Aquatest 8 Karl-Fischer Titrator (Photovolt Instruments, Indianapolis, IN) according to the method described by Kim et al. A 19 gauge needle was inserted through the septum of the titration cell with the needle tip placed below the reagent, and each formulation was measured in triplicate. For all formulations tested the moisture content was approximately 500 ppm. The pure HFA was found to have a moisture content of 250 ppm. The total amount of moisture to the amount of protein particles was 7% (w/w).

The particles were initially dispersed by pipette mixing in HPFP and were observed for about 2 minutes with a Nikon OPTIPHOT 2-POL optical microscope with an attached MTI CCD-72× camera (Nikon, Tokyo, Japan). Pictures were taken 30 and 60 seconds after initial dispersion in HPFP.

Figure 2:
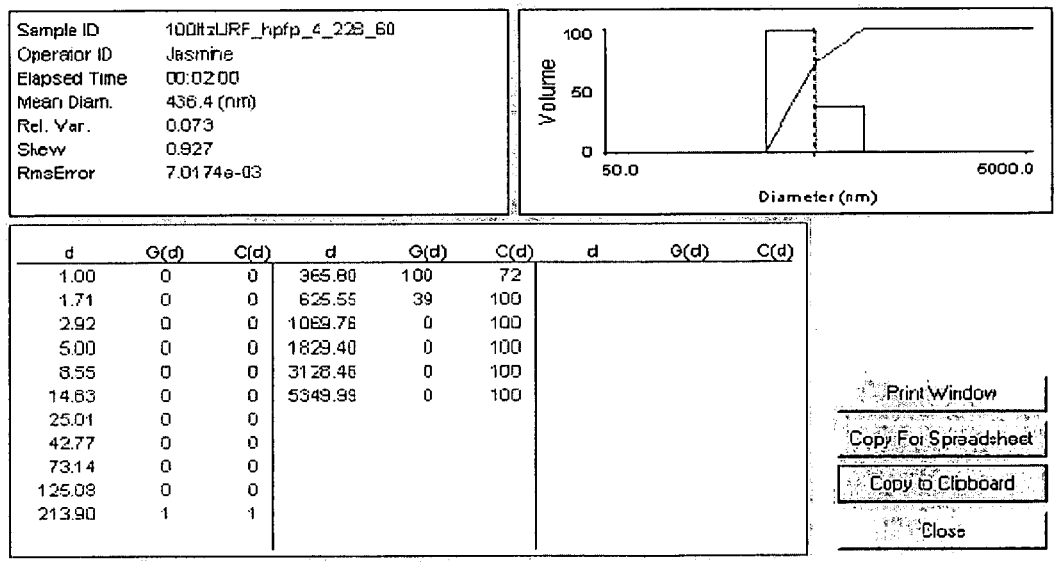
FIG. 2 is a table of URF Itz powder dispersed in HPFP.

FIG. 2 is a table of URF ITZ powder dispersed in HPFP. The µQuant spectrophotometer was used to measure turbidity at 350 nm to characterize BSA aggregation. Dry powders of BSA were reconstituted to 1 mg/mL and 3×300 uL aliquots of each formulation were placed in a 96 well Falcon plate which was set in the spectrophotometer.

Particles of BSA suspended in acetonitrile were analyzed by a custom-built dynamic light scattering (DLS) apparatus. The scattering angle was set to 90° and the data were analyzed a digital autocorrelator (Brookhaven BI-9000AT) and a non-negative least-squares (NNLS) routine (Brookhaven 9 KDLSW32). The suspension concentration was 0.5 mg/mL which gave a measured count rate of approximately 150 kcps. Measurements were made over a period of about 2 minutes.

Approximately 100-300 mg of protein powder was loaded into a 100 mL graduated cylinder. The tap density of the protein particles was measured with a Vankel tap density meter (Varian, Palo Alto, CA).

FIGS. 3A and 3B are SEM images of pMDI formulation, while 3C and 3D are the corresponding graphs of particle size. The fluffy BSA particles made by TFF shown in FIG. 2A had a low tap density of 0.0064 g/cm³. The morphology of the BSA powder prepared by TFF was interconnected rods 50 nm in diameter as seen in FIG. 3A. With the addition of 5 mg/mL trehalose to the BSA feed solution, similar rods were produced, as well as fine 50-100 nm relatively spherical particles FIG. 3B. Similar morphologies were observed previously for lysozyme produced by TFF at 223 K. The BSA particles prepared by wet milling as seen in FIG. 3C did not have high external porosity like the TFF particles, but were in the form of cubes with smooth sides with 400-800 nm dimensions. Lastly, spray drying BSA at a feed concentration of 10 mg/mL formed protein particle spheres 3-6 µm in diameter with smooth surfaces as seen in FIG. 3D.

For characterization by static light scattering, the various BSA particles suspended in acetonitrile were sonicated for about 2 minutes. FIGS. 4A-4B are TEM images of URF ITZ aerosol from pMDI. As shown in FIG. 4 the d(v,50) values were 330 nm, 410 nm and 6.3 µm for the TFF, milled and spray dried BSA particles, respectively, consistent with the sizes in the SEMs. Thus, the primary particles remain dispersed in acetonitrile and do not aggregate. As demonstrated previously with lysozyme, the cooling rate in the TFF process for BSA was sufficiently fast to form high surface area powders that redisperse to 330 nm particles in acetonitrile, with little sonication (less than about 2 minutes). As a further indication of high tendency of the nanorods to deaggregate and disperse in acetonitrile, even with no sonication 2 peaks were observed with maxima at 330 nm and 20 µm, with approximately 50% of the particles by volume below 1 µm as shown in FIG. 4. Thus the aggregation of the nanorods in the powder state is highly reversible.

To compliment the light scattering results by SEM, the sonicated suspensions in ACN were frozen by drip freezing into liquid nitrogen. The acetonitrile was then removed by lyophilization leaving fluffy particles with an approximate tap density of 0.012 g/cm³ (FIG. 2B). When the particles were redispersed in acetonitrile the measured particle size profile was d(v,50)=330 nm which was similar to the profile in FIG. 4 of the original TFF dispersion, indicating that the lyophilization process did not cause irreversible particle aggregation. As observed by SEM, the morphology in FIG. 3E were 50-100 nm diameter rods, similar to the interconnected rods of the original TFF powder in FIG. 3A, and consistent with the sizes from light scattering results in FIG. 4. Thus exposure to acetonitrile followed by sonication does not alter the morphology significantly.

FIGS. 5A and 5C are data for the 100% Itz URF samples shown in the SEM images FIGS. 5B and 5D. FIG. 5E is a XRD of URF ITZ powder. The dried TFF BSA particles were suspended in HFA 227 and acetonitrile (ACN) at 0.70% (w/w) corresponding to a volume fraction in the vial $\phi_v$ of 0.0077, as determined from the true density of BSA $\rho_p$=1.3 g/cm³ as shown in FIG. 5. As shown in FIG. 5A, the particles did not settle even after 1 year in storage in HFA 227. Immediately upon adding HFA, the particles formed flocs that filled the entire volume of the vial. For a control with an extremely low $\phi_v$ of only 0.070% (w/w) as shown in FIG. 5B the loose buoyant flocs still filled approximately half the HFA volume. For the milled BSA nanoparticles, the suspension initially appeared to be uniform (as in FIG. 5A), but the particles settled to the bottom after only 5 minutes as shown in FIG. 5C. Since these particles settled in HFA 227 (1.41 g/cm³), the milling may have compacted the particles to ρ above 1.3 g/cm³. These particles creamed in HPFP (1.59 g/cm³). Thus, it was estimated that $\rho_p$~1.50 g/cm³, the average of the two solvent densities. The spray dried particles dispersed well with shaking, but creamed after only 2 minutes as shown in FIG. 5D. The TFF nanorods suspended in acetonitrile and sonicated for 2 minutes formed a milky uniform dispersion as shown in FIG. 5E. After 3 days the particles had settled as shown in FIG. 5F. The dispersion/settling behavior shown in FIGS. 5E and 5F was also observed for milled and spray dried particles in acetonitrile (data not shown) with settling in about 3 days and about 30 minutes, respectively.

Figure 6:
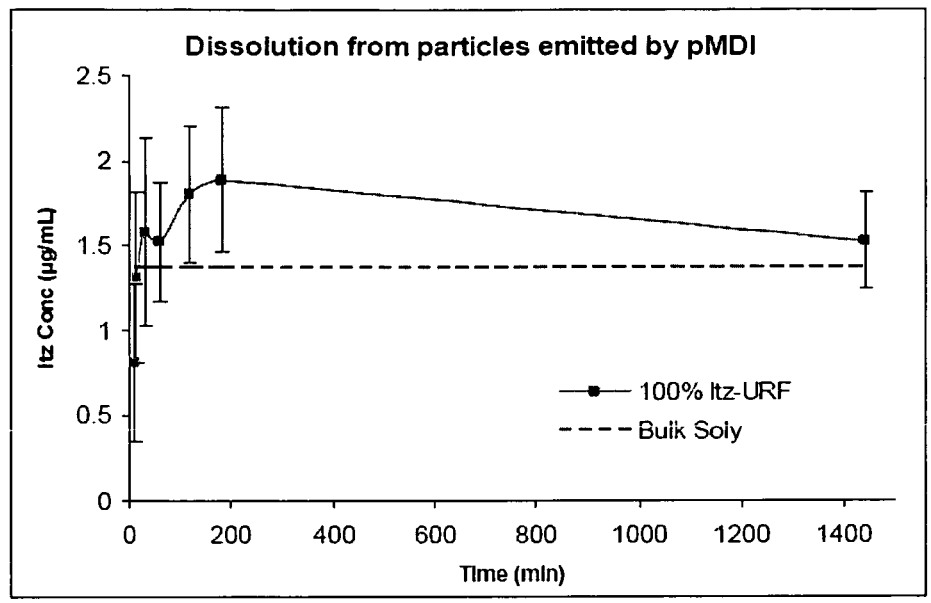
FIG. 6 is a dissolution graph of particles emitted by pMDI.

Because the vapor pressure of HFA 227 is above ambient at 250° C. (about 500 kPa), the particles were not studied in situ by microscopy or light scattering. Instead, the particles were studied at ambient pressure in HPFP, a surrogate nonvolatile solvent. Because HPFP has a similar polarity and polarizability as HFA 227, attractive forces between solutes such as budesonide are similar in both solvents on the basis of atomic force microscopy (AFM). FIG. 6 is a dissolution graph of particles emitted by pMDI. According to light microscopy (FIG. 6A), the TFF particles in HPFP were in the form of loosely packed aggregates of rods as shown in FIG. 6B and FIG. 6C. The particles were in 200-300 µm flocs with subdomains on the order of 25 µm within 5 seconds after dispersing the particles by pipette mixing (see FIGS. 6A and 6B). For the spray dried (as shown in FIGS. 6D and 6E) and milled (as shown in FIG. 6F) particles, 100 µm flocs formed in 30 seconds and grew to over 200 µm in 60 seconds.

FIGS. 7A-7B are SEM images of Charleston sample Dow amorphous ITZ. These flocs were more densely packed and composed of larger primary particles than those formed from TFF particles. These sizes were consistent with static light scattering measurements of the sonicated and unsonicated suspensions in HPFP with d(v,50) values between about 215-259 µm.

To better anticipate the fate of particles throughout the pMDI delivery process, it would be beneficial to determine how reversibly the nanorods are bound together in the flocs. The elevated pressure of the HFA complicates in situ light scattering. Furthermore, the HFA suspension could not be lyophilized to prepare a sample for SEM since the freezing point (−131° C.) of HFA 227 is too low to for conventional shelf lyophilizers. To investigate the effect of HFA evaporation on the particles, HFA was cooled to −80° C., well below the boiling point of −16° C., and completely evaporated. The TFF particle residue only occupied approx. 1 mL (tap density of 0.10 g/cm$^3$, FIG. 8A), an order of magnitude less than that of the starting TFF bulk powder as shown in FIG. 2A.

FIGS. 8A-8C are SEM images of Charleston sample Dow amorphous ITZ from pMDI. The morphology shown in FIG. 8A was rods with 100 nm diameters (see FIG. 8B), similar to the original TFF particles in FIG. 3A. Therefore, exposure to HFA 227 followed by sonication did not significantly alter the microscopic nanorod morphology. However, the densified aggregates of the nanorods formed by capillary forces upon evaporation as shown in FIG. 5B of HFA were not redispersible in HFA or in ACN. For a sonicated TFF paticle dispersion in ACN, the lyophilized powder was redispersible in ACN and in HFA, forming suspensions identical to FIG. 5A. Thus it appeared that the capillary forces during HFA evaporation and perhaps moisture produced irreversibly aggration of the nanorods.

Figure 7:
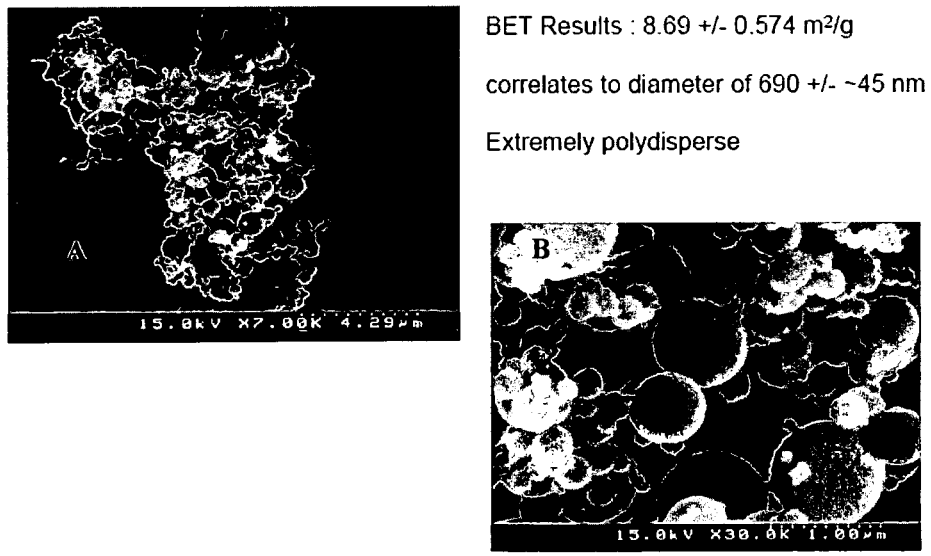
FIGS. 7A-7B are SEM images of Charleston sample Dow amorphous Itz.

Given the challenges of in situ high pressure light scattering, lyophilization of HFA 227, and compaction of the TFF rods by capillary forces upon HFA evaporation, a more practical approach was to transfer the suspension from HFA 227 to a less volatile solvent. If the nanorods redisperse to primary particles in a good solvent such as acetonitrile, then they were not aggregated irreversibly in HFA 227. A 2 mL aliquot of the cold TFF suspension was mixed directly with 500 mL of acetonitrile at 25° C. The flocs deaggregated nearly completely to individual primary particles with over 80% of the volume distribution between 100 nm and 1 µm, and a maximum at 11 µm as shown in FIG. 7. A relatively small peak was centered at 5 µm. The distributions nearly matched those of the original TFF particles in ACN. In a complimentary experiment, the valve of the pMDI containing was submerged into acetonitrile and actuated. A slightly turbid dispersion was formed with an approximate particle concentration of 0.5 mg/mL, too low for detection by static light scattering, but not for DLS.

FIGS. 9A-9B are graphs and 9C is a SEM characterizing the ITZ sample made by CP. From DLS, the particle size was 1-2 µm much smaller than the 250 µm floc size in HFA. Therefore, both experiments indicate the loosely connected flocculated nanorods in HFA were reversible and broke up into primary nanorods, which will be shown to be beneficial for lung delivery.

Aggregates of protein molecules did not appear to form according to optical density (OD) measurements at 350 nm of 1 mg/mL BSA [43,61]. The OD was the same at 0.042 for aqueous solutions in 10 mM phosphate pH=7.4 buffer prepared from bulk and TFF powder, both before and after storage in HFA 227 for 1 week. In the glassy state, BSA is less susceptible to aggregation. The total moisture to BSA content was 7% (w/w) for the suspended BSA particles in HFA 227 as determined by Karl-Fischer titration. Even at particle moisture contents of 8% (w/w), BSA glass transition temperatures $T_g$ range between 80-100° C. Thus the temperature was well below $T_g$, assuming the HFA 227 did not contribute to plasticization.

The suspension must be stable for consistent dosing with a pMDI, which is commonly characterized by the dose (mass) delivered through the valve (DDV) as seen in Table 1.

TABLE 1

| Formulation | DDV (µg) | % Theoretical DDV | FPF (%) | Fine Particle Dose/Actuation (µg) | ED (µg) |
|---|---|---|---|---|---|
| TFF BSA | 915 ± 21 | 92 | 47 ± 4.0 | 318 ± 31 | 695 ± 133 |
| TFF BSA Tween 20 | 826 ± 58 | 83 | 43 ± 4.2 | 292 ± 16 | 590 ± 71 |
| TFF BSA:Tre 1:1 Tween 20 | 452 ± 54 | 90 | 38 ± 2.1 | 132 ± 19 | 350 ± 56 |
| TFF BSA unsonicated | 625 ± 95 | 63 | — | — | — |
| Milled BSA | 295 ± 17 | 30 | — | — | — |
| Spray Dried BSA | 308 ± 38 | 31 | — | — | — |

TABLE 1: ACI results for different protein pMDI formulations at different protein concentrations. Bovine serum albumin (BSA) and lysozyme (Lys) formulations shown.

The concentration was 10 mg/mL or 0.7% (w/w) in each HFA suspension. Therefore, the theoretically delivered dose per actuation would be 1 mg with the 100 μL valve. For the BSA TFF particles, the DDV values were 92% and 63% of the theoretical delivery dose for the sonicated and unsonicated TFF particles, respectively as seen in TABLE 1. For the BSA:Trehalose 1:1 formulation, it was 90%, and the delivered dose was 450 μg/actuation as a consequence of the lower amount of BSA loaded into the vial. For the milled and spray dried suspensions with rapid settling, the DDV was only 30-31% of the theoretical loading. Here, the formulation was actuated less than 5 seconds after vigorous shaking. Therefore, these suspensions were not tested further for aerosol properties.

Figure 10:
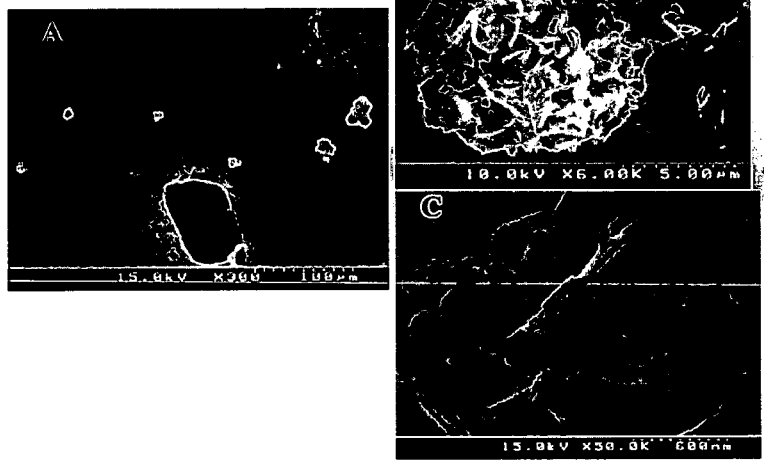
FIGS. 10A-10C are SEM images of Itz made by CP from pMDI.

FIGS. 10A-10C are SEM images of ITZ made by CP from pMDI. As shown in Table 2 and FIG. 10, the $d_a$ determined from the Andersen cascade impactor (ACI) and the Aerodynamic Particle Sizer (APS) were in good agreement and ranged from 3 to 4 μm, within the optimal 1-5 μm range for pulmonary delivery.

$$D_{Vol} = \frac{\sum d^4}{\sum d^3} \quad (1)$$

where d is the measured diameter of the particle. The $D_{vol}$ for BSA was approximately 9 μm, while for BSA:Trehalose 1:1 it was slightly smaller, 7 μm (TABLE 2). The $d_g$ of the aerosolized particles were also measured by static light scattering. An effective refractive index $n_e$ was calculated according to the Bruggeman mixing rule [66] based on the volume fraction of BSA in the aerosolized particle $\phi_g$. From the $d_g$ and the $d_a$ (see Table 2), the particle density $\rho_g$ can be defined by $$d_a = d_g \sqrt{\rho_g} \quad (2)$$

where $\rho_g = 0.19$ g/cm$^3$. The resulting $\phi_g = \rho_g/\rho_p = 0.14$. With n=1.45 and 1.00 for pure BSA and air, respectively, $n_e = 1.1$. As shown in TABLE 2 the volume average d(v,50) particle sizes varied by less than 1 μm from the values determined from the SEM micrographs. The consistent $d_g$ and $d_a$, each measured by two techniques, indicate that TFF particles form large porous particles, and with the optimal size range

TABLE 2

| Formulation | ACI MMAD (μm) | ACI GSD | APS MMAD (μm) | APS GSD | d(v, 50) Particle Diameter (μm) | SEM Particle Diameter (μm) | $\rho_g$ (g/cm$^3$) |
|---|---|---|---|---|---|---|---|
| BSA | 3.1 ± 0.1 | 1.9 ± 0.1 | 3.2 ± 0.03 | 1.6 ± 0.01 | 9.1 ± 0.9 | 9.4 | 0.19 |
| BSA Tween 20 | 3.6 ± 0.1 | 1.9 ± 0.2 | — | — | 9.9 ± 0.8 | 9.3 | — |
| BSA:Tre 1:1 Tween 20 | 3.2 ± 0.2 | 1.8 ± 0.1 | 4.0 ± 0.15 | 1.7 ± 0.01 | 7.3 ± 0.5 | 7.4 | — |

As determined by the ACI, the fine particle fraction (FPF) (particles less than 4.7 μm) was unusually high [32] for an HFA suspension, ranging from 38 to 48% compared to 5 to 30% for typical suspensions [32], producing a fine particle dose/actuation of approximately 300 μg for the first two formulations in TABLE 1. The emitted dose (ED) (amount of drug that exited the actuator) was approximately 70% of the DDV upon actuation (see TABLE 1 and FIG. 10A). The addition of Tween 20 did not affect any of the properties of the aerosolized TFF powders in TABLE 1 significantly or the suspension stability, indicating that it was not needed as a stabilizer.

The particles were recovered from the ACI for SEM analysis. The peak drug mass in the ACI was deposited on stages 3 and 4, with $d_a$ between 2.0-4.7 μm as shown in FIG. 10A. Therefore, particles were collected on stage 3 ($d_a$=3-4 μm).

FIG. 11 is a table comparing ITZ formulations. The particles were porous and composed of rods with diameters less than 500 nm (see FIGS. 11A and 11B), similar in morphology to the original nanorods in FIG. 3A. For BSA: Trehalose 1:1 the fine 50-100 nm primary particles, shown in FIG. 3B, changed morphology to include curved plates with features on the order of more than one micron as shown in FIGS. 11C and 11D.

The SEMs were analyzed by Scion software o determine the volume average diameter for pulmonary delivery upon aerosolization. When the TFF particles were actuated above 10 mM phosphate buffer (pH=7.4) the porous particles were observed to dissolve in less than 5 seconds. The high surface area favors rapid dissolution, which could be advantageous for rapid dissolution rates of proteins that have low solubilities in water.

The van der Waals forces between particles play a key role in the differences in colloidal stabilities of various types of primary particles and the behavior of the flocs in this study, as depicted in the summary in FIG. 1. According to the Derjaguin-Landau-Verwey-Overbeek (DLVO) theory, particle stability depends on counteracting the attractive van der Waals forces by electrostatic and/or steric repulsion. If attractive van der Waals (VdW) forces are dominant at all separation distances, particles flocculate and may then settle. Currently, electrostatic stabilization in HFAs is not well understood, but atomic force microscopy (AFM) measurements indicate that electrostatic forces may be negligible compared to attractive VdW forces. The understanding of steric stabilization in HFAs is in its infancy. While novel surfactants are being discovered, developed and approved, alternative mechanisms form the formation of stable suspensions in HFAs without surfactants would be useful.

The destabilizing van der Waals attractive forces between suspended are weaker for porous particles or hollow particles with thin solid shells. These particles can be stable for hours in HFAs, compared to non-porous 1-5 micron particles, which often flocculate and settle rapidly in less than 1 minute (see TABLE 2). Dellamary et al. suggested that the increased suspension stability resulted from a weaker attractive VdW energy potential $\Phi_{vdw}$ between the particles (FIG. 1A), but quantitative calculations were not presented.

As shown in the Appendix the van der Waals energy $\Phi_{vdw}$ is directly proportional to the Hamaker constant $A_{121}$. In order to compare values of $\Phi_{vdw}$ it is necessary to choose a separation distance, D, between particles. TABLE 3 gives the D where $\Phi_{vdw}$ becomes equivalent to the thermal energy $3/2\, k_B T$ at 298K.

TABLE 3

| Particle Type | Particle diameter | Hamaker constant $10^{21}$ $A_{121}$ (J) | Separation Distance (nm) at $\Phi_{vdw} = 3/2\, KgT$ |
|---|---|---|---|
| Spray dried Non-porous | 5.0 | 14 | 270 |
| Spray dried Porous $\Phi = 0.5$ | 5.0 | 3.8 | 100 |
| Spray dried Hollow sphere $\Phi = 0.12$ | 5.0 | 14 | 120 |
| TFF Nanorods | 0.33 | 14 | 23 |
| TFF Nanorods | 0.33 | 2.6 | 6.9 |

An increase in D required to overcome thermal energy indicates stronger attraction between particles. In TABLE 3, the porous particles with $\phi=0.5$ had a calculated $A_{121}$ (Eq. A.3) that was nearly a factor of 4 lower than for the non-porous particles. Consequently, D was a factor of 3 smaller. The hollow spheres from TEM images were estimated to have 2-5 μm diameters and about 100 nm thick shells. Although the $A_{121}$ for the hollow sphere particles with solid shells was the same as for the non-porous particles, the calculated D was still lower by a factor of 2 as a consequence of the differences in the geometries (Eq. A.5). Therefore, the $\Phi_{vdw}$ calculations quantify the benefits of weaker attraction for porous particles or for particles with hollow cores. A reduction in $\Phi_{vdw}$ or in D to overcome thermal energy can reduce the rate of flocculation over orders of magnitude as described by the stability ratio.

Although, the porous or hollow sphere particles can effectively prevent flocculation, the particles are still subject to settling by gravity. If porous or hollow sphere BSA particles were suspended at $\phi_v=0.0077$, the particles would occupy about 10% of the suspension (as shown in FIG. 1A) and could potentially settle into a dense sediment. As shown in TABLE 4, the calculated settling rate for a single hollow sphere particle with a solid shell is $6.4\times10^{-4}$ mm/s indicating that the particles would settle a distance of 2 cm in about 9 hours. The settled particles would then potentially aggregate irreversibly leading to decreased FPFs upon aerosolization.

density flocs and thus fill much greater space compared to spheres as illustrated in FIGS. 1B and 1C. For spheres, the volume fraction of primary particles within a floc $\phi_f$ is related to the floc diameter $d^{floc}$, primary particle diameter $d_p$, and fractal dimension $D_f$, which characterizes the floc structure, by $$\phi_f \approx \left(\frac{d^{floc}}{d_p}\right)^{D_f - 3} \quad (3)$$

Philipse et al. modified Eq. 3 to account for the packing physics of cylindrical rods of length L and diameter D with the result $$\phi_f \approx \frac{1}{r} \cdot \left(\frac{d^{floc}}{V_p^{1/3}}\right)^{D_f - 3} \quad (4)$$

where r=L/D is the aspect ratio. The volume of a TFF cylindrical rod, $V_p=0.019$ dm$^3$, was calculated from the equivalent volume of a sphere with particle diameter d(v, 50)=0.33 μm, which was measured by static light scattering (as shown in FIG. 4A) in acetonitrile. For a rod with volume $V_p=\pi \cdot D^2 L/4$ and D=0.050 μm (as shown in FIG. 3A), L is determined as 0.48 μm and thus r=9.6. For r~10, the predicted $\phi_f$ in Eq. 4 is ~1 order of magnitude lower than for spherical particles with equivalent $d^{floc}$, $D_f$, and where $d_p$ for spheres scales as $V_p^{1/3}$ for rods.

The density of a floc $\rho_f$ and $\phi_f$ can be determined experimentally from the visually observed floc settling rate, $U_f$, according to Stoke's law $$U_f = \frac{d^{floc\,2} \cdot (\rho_f - \rho_L) \cdot g}{18 \cdot \mu} \quad (5)$$

where $\rho_L$ and μ are the liquid density and viscosity, respectively, and $d^{floc}=250$ μm for TFF flocs and 100 μm for spray dried and milled flocs. After solving for $\rho_f$ in Eq. 5, $\phi_f$ may be determined by the straightforward material balance $\rho_f = \rho_L + \phi_f (\rho_p - \rho_L)$. As seen in Table 4, $\phi_f$ for the TFF particles is 1-2 orders of magnitude lower than for the spherical milled and spray dried particles. From Eq. 3 and 4 the calculated $D_f$ values are in a narrow range from 2.4 to 2.6 in each case. Although the milled and TFF particles have

TABLE 4

| Particle Type | $d_p$ (μm) | $d^{floc}$ (μm) | $(\rho_L - \rho_f)$ (g/cm$^3$) | $U_f$ (mm/s) | $U_p$ (mm/s) | $\varphi_f$ | $\varphi^{flocs}$ | $\varphi_f$ | $D_f$ |
|---|---|---|---|---|---|---|---|---|---|
| TFF | 0.33$^a$ | 250 | 0.00022 | 0.023 | $2.4 \times 10^{-5}$ | 0.00077 | 0.38 | 0.0020 | 2.4 |
| Milled | 0.41 | 100 | 0.0080$^b$ | 0.13 | $3.7 \times 10^{-5}$ | 0.0067 | 0.11 | 0.073 | 2.5 |
| Spray Dried | 6.3 | 100 | 0.040 | 0.80 | $8.8 \times 10^{-3}$ | 0.0077 | 0.021 | 0.36 | 2.6 |
| Spray Dried-Hollow Sphere | 5.0$^c$ | — | 0.013$^d$ | — | $6.4 \times 10^{-4}$ | — | — | — | — |

$^a$Value determined from the equivalent volume of a sphere measured from laser light scattering
$^b$The density difference was determined by $\rho_f - \rho_L$ with $\rho_p = 1.5$ g/cm$^3$
$^c$Determined from dimensions given by Dellamary et al. (1)
$^d$Calculated for primary particle with 100 nm thick shell The concept in this study of stabilizing suspensions with purposely flocculated rods is based on the space filling properties of the rods and the flocs. Experimental and theoretical studies indicate that rods create extremely low nearly equivalent $d^{floc}$ and $D_f$ values relative to the rods (as seen in Table 4), the 1/r scaling in Eq. 5 for rods accounts for the 1 order of magnitude decrease in $\phi_f$ for a given $V_p$, which is consistent with theoretical prediction above.

The one or more anisotropic particles may have an aspect ratio range of between 0.1 and 2.0 or greater, e.g., the aspect ratio may be 0.2, 0.3, 0.4, 0.5, 0.6, 0.7, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9 and so on.

The extremely low $\phi_f$ means the flocs will fill a huge volume of space for a given $\phi_v$ (as shown in FIG. 1C). The open nanorod flocs with low $\phi_f$ filled large amounts of space in HFA and stacked upon each other like tumbleweeds to prevent settling. The volume fraction of flocs in the HFA suspension, $\phi^{flocs}$ is given by $\phi^{flocs}=\phi_v/\phi_f$ (derivation given in Appendix) where $\phi^{flocs}$ determines the space filling capability of the flocs. As $\phi^{flocs}$ approaches 1 the flocs occupy the entire volume of HFA (as shown in FIG. 1C). For the dilute $\phi_v=0.00077$ suspension (as shown in FIG. 5B), the calculated $\phi^{flocs}$ was about 0.38 (see Table 4) in good agreement with FIG. 5B. At a loading 10 fold higher, $\phi_v=0.0077$, the entire vial was white without the appearance of spaces between flocs (as shown in FIG. 5A), as expected from the low $\phi_f$. Here it was not possible to observe a settling rate as the visual appearance did not change for 1 year, the maximum time tested, as the $\phi^{flocs}$ of essentially unity prevented settling. In order for the spherical particles to produce $\phi^{flocs}=1$ the required mass loadings for the milled and spray dried particles would be 6.7% (w/w) and 33% (w/w), respectively, compared to <0.7% (w/w) for the TFF rods.

In contrast to the TFF rods, the hollow sphere particles would settle the length of the vial (about 2 cm) by gravity in about 9 hours according to Stoke's law for a particle diameter of 5 μm and shell thickness of 100 μm. In the settled state with a high particle volume fraction and contact between protein chains they are more likely to form irreversible particle aggregates by interparticle diffusion and sintering.

The open flocs in HFA 227, that gave the stable suspensions, may be shown to be favored by the relatively strong attractive forces between the primary particles. At first, this may seem counterintuitive to the normal goal of lowering attractive forces to stabilize colloidal dispersions. Upon addition of the HFA, the relatively strong attractive forces between the primary rods, $\Phi_{vdw}$, cause sticky collisions to "lock in" the open structure rapidly to inhibit collapse of the flocs. For weaker attractive forces between primary particles, collapse has been shown to be more prevalent as particles sample a greater number of energetically favorable locations to reduce the interfacial surface area. Therefore, rapid flocculation from sticky collisions facilitates the formation of low density flocs that fill the entire vial and prevent settling.

In contrast to the flocs in HFA 227, colloidal dispersions of primary TFF rods in acetonitrile settled in 3 days (as shown in FIG. 5F). This settling rate agreed with the predicted settling rate of individual effective spheres with a diameter of 330 nm from light scattering given in Table 4. From Table 3, the calculated $A_{121}$ values for BSA in acetonitrile are 1 order of magnitude lower than in HFA 227. Therefore, the stronger attractive forces between particles in HFA relative to ACN, favors formation of open flocs, resulting in more stable suspensions against settling.

Although the 250 μm flocs form stable suspensions, they are too large to produce optimal $d_a$. The shear forces in the actuator are needed to break apart the flocs. The calculation of these shear forces is rarely reported because the turbulence from the immediate onset of HFA evaporation produces complex cavitation events. According to empirical models, aerosolized HFA droplets are typically about 10-30 μm in diameter. Thus we choose an HFA droplet diameter of 25 μm. The shear forces acting on the flocs are sufficiently strong to overcome the attractive van der Waals interactions between primary particles within a floc such that the HFA droplets may template the 250 μm flocs into 25 μm subdomains with the same $\phi_f=0.0020$ as illustrated schematically in FIG. 1. From the high $\phi^{flocs}$ (TABLE IC) it is expected that most of the HFA droplets are likely to be filled with a subdomain.

Since direct comparison of calculated shear forces to van der Waals forces of primary particles within a floc is unfeasible, the concept of templating of the 25 μm subdomains is instead supported by a material balance on the protein between the volume of the HFA droplet, $V_{HFA}$, and the volume of the dry aerosolized particle, $V_g$, (as shown in FIG. 1C) given by $$V_g \cdot \rho_g = V_{HFA} \cdot \rho_{HFA} \quad (6)$$

where BSA concentrations are given by $\rho_{HFA}=\phi_v \cdot \rho_p$, and $\rho_g=\phi_g \cdot \rho_p$. It is assumed that the volume fraction of particles in HFA droplet is approximately equal to $\phi_v$ as a result of the break up of the flocs. From the $d_g$ and $d_a$ in Table 2 and $\rho_g=0.19$ g/cm³ (Eq. 2), $\phi_g=0.14$. The $\phi_g$ is nearly 20 times greater than $\phi_v$ in the vial. Therefore, the capillary forces in the shrinking HFA droplets during evaporation collapse the flocs. Eq. 6 is refined to relate $\phi_g$ to $\phi_v$ as $$\phi_g \cdot d_g^3 = \frac{f_{BSA}}{f_{HFA}} \cdot \phi_v \cdot d_{HFA}^3 \quad (7)$$

where d is a diameter, $f_{BSA}=0.7$ accounts for the mass fraction of drug that is emitted from the actuator, and $f_{HFA}=0.5$ accounts for the mass fraction of HFA that exits the actuator orifice to form aerosolized liquid droplets (relative to vapor).

From Eq. 7 with $d_g=9.3$ μm (TABLE 2), $d_{HFA}=25$ μm, and $\phi_v=0.0077$, the calculated $\phi_g=0.21$, which compares reasonably well to the experimentally determined $\phi_g=0.14$. Also the polydispersity in the aerodynamic properties was small. It would be unlikely that any other factor besides templating of the flocs with relatively uniform HFA droplets could explain these low polydispersities.

The control in FIG. 8A supports this argument since the TFF particles remained below the meniscus of the evaporating HFA 227. The tap density of the particles was approximately 0.10 g/cm³ (FIG. 8A) which is within a factor of 2 of the calculated density (0.19 g/cm³) of the aerosolized particle. Therefore, the capillary forces acting on the TFF particles during HFA evaporation compacted the particles into denser aggregates with a highly desirable value of the $d_a$. If needed, the $d_a$ may be manipulated further by varying the valve volume and geometry and the HFA droplet generation. If the particles had not collapsed partially, they would have been too large and light for pulmonary delivery. Even after this collapse, the porosity and surface area were still relatively high and favorable for high dissolution rates of small molecules and proteins with limited solubilities, relative to nonporous particles.

High (e.g., about 38-48%) fine particle fractions in HFA 227 pMDI delivery were achieved with flocculated BSA nanorods stable against settling for up to 1 year, without the use of surfactants and cosolvents. Analysis of experimental settling rates of dilute suspensions indicated that the volume fraction, $\phi_f$, of the nanorods in the flocs was an order of magnitude lower than for flocs of spherical particles produced by milling or spray drying. The rapid and sticky attractive collisions of nanorods, facilitates the formation of low density flocs (250 μm) which stack upon each other to fill the entire solvent volume to prevent settling. In contrast, denser flocs of spherical particles filled much less space and rapidly settled within 60 seconds. The novel concept of purposely flocculating nanorods to prevent settling is fundamentally opposite the conventional approach of stabilizing colloidal dispersions of primary particles. The reversibility of the nanorod flocs in HFA 227 was demonstrated by break up of the flocs into individual 330 nm primary rod particles upon transfer to the more polar solvent acetonitrile.

A material balance on a shrinking HFA droplet containing a 25 μm floc subdomain predicts a final volume fraction of BSA in the aerosolized particle in agreement with experiment. Therefore, the attractive van der Waals interactions between primary particles within the floc are sufficiently weak such that the atomized HFA droplets initially template the 250 μm flocs into 25 μm subdomains. The aerosolized particles with a $d_a$ of 3-4 μm and $d_g$ of about 10 μm are optimal for high fine particle fractions via a pMDI. The concept of forming open flocs composed of nanorods, that are stable against settling without surfactants, and templating the flocs to achieve optimal $d_a$s and high FPFs is of practical interest for wide classes of low and high molecular weight pharmaceuticals and biopharmaceuticals.

Figure 16:
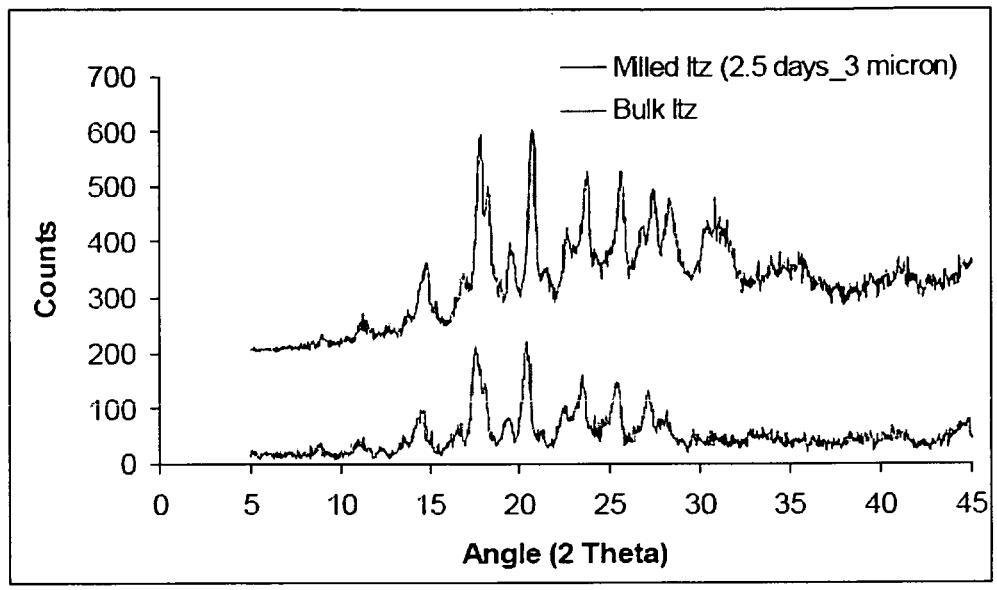
FIG. 16 is a XRD of milled Itz particles.
Figure 17:
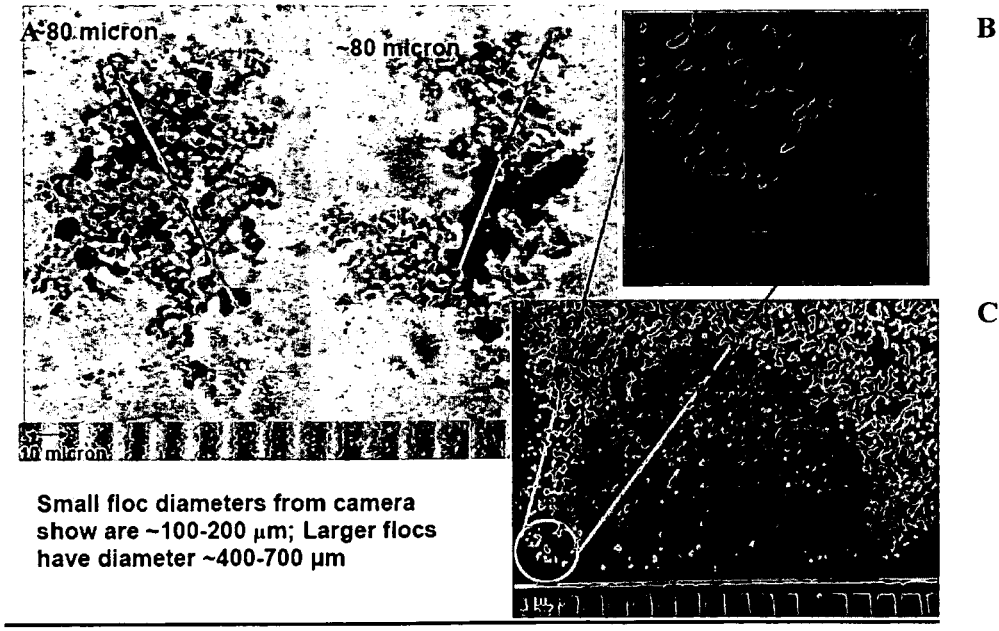
FIGS. 17A-17C are SEM images of TFF particles in HPFP.
Figure 18:
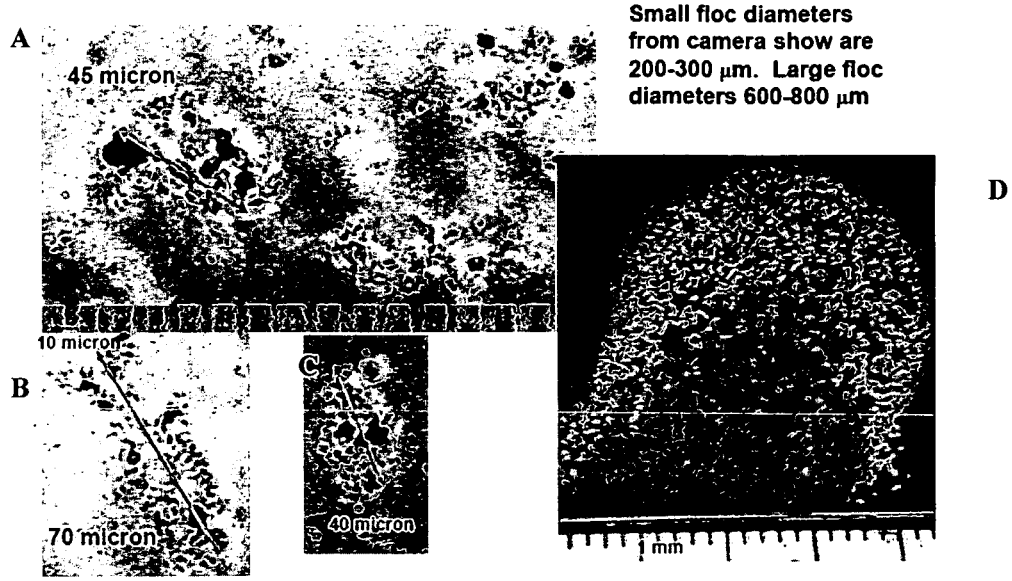
FIGS. 18A-18D are SEM images of CP Itz particles in HPFP.
Figure 19:
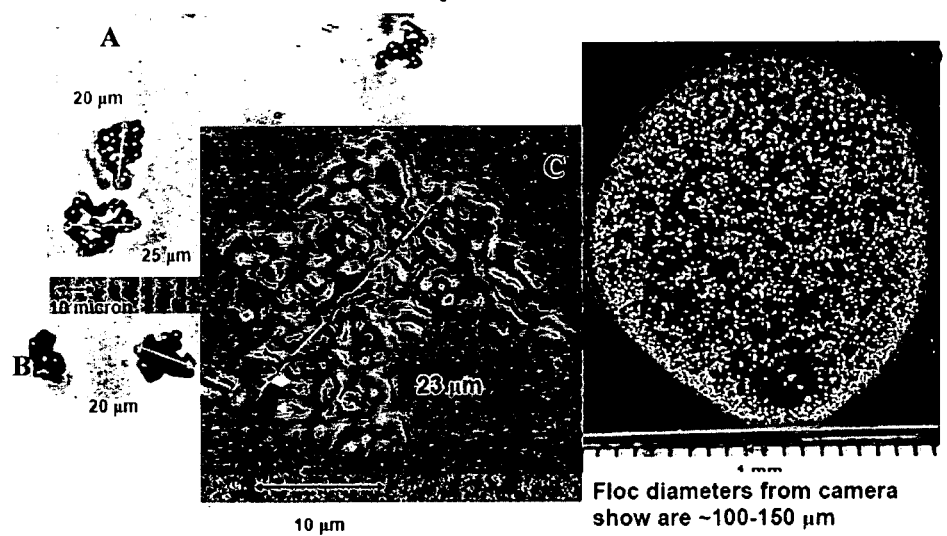
FIGS. 19A-19D are SEM images of Dow amorphous in HPFP.
Figure 20:
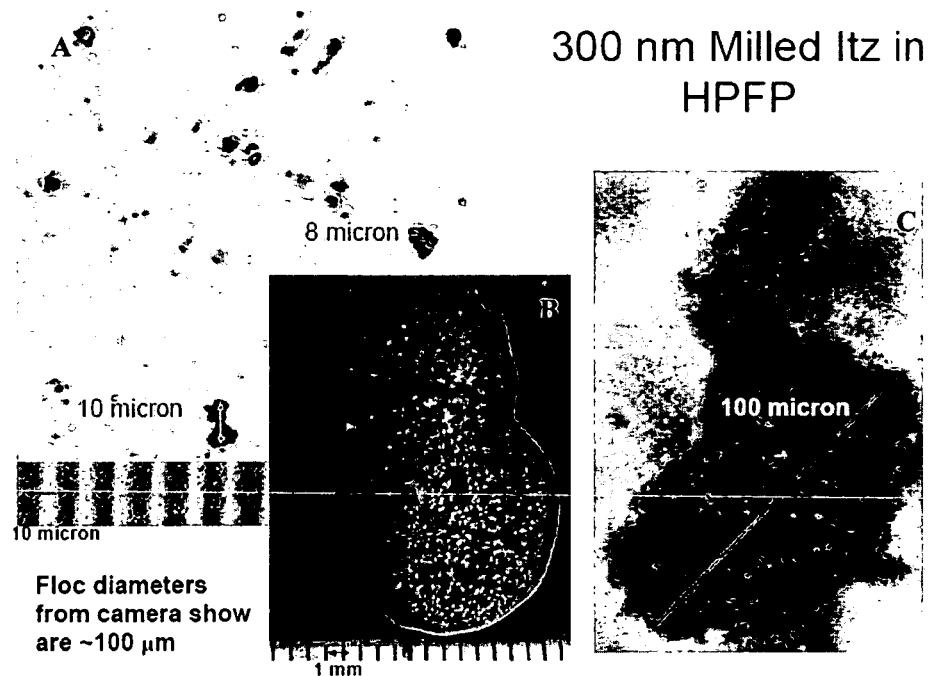
FIGS. 20A-20C are SEM images of milled Itz particles in HPFP.
Figure 21:
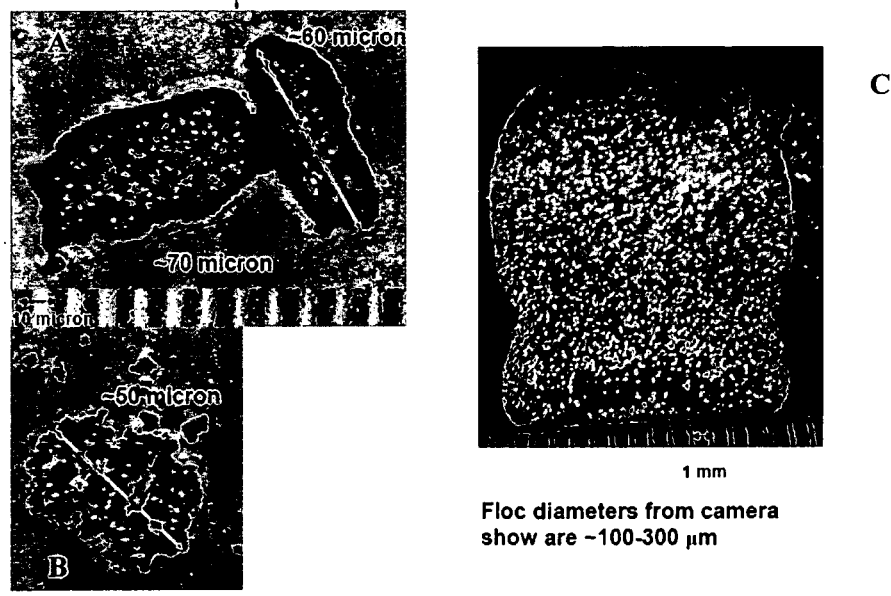
FIGS. 21A-21C are SEM images of milled Itz particles in HPFP.

FIG. 12 is a table comparing particle dimensions of ACI. FIGS. 13A-13C are SEM images of milled ITZ particles. FIG. 14 is a graph of the milled control particles. FIGS. 15A-15D are SEM images of milled aerosolized milled particles. FIG. 16 is a XRD of milled ITZ particles. FIGS. 17A-17C are SEM images of TFF particles in HPFP. FIGS. 18A-18D are SEM images of CP ITZ particles in HPFP. FIGS. 19A-19D are SEM images of Dow amorphous in HPFP. FIGS. 20A-20C are SEM images of milled ITZ particles in HPFP. FIGS. 21A-21C are SEM images of milled Itz particles in HPFP.

Figure 24:
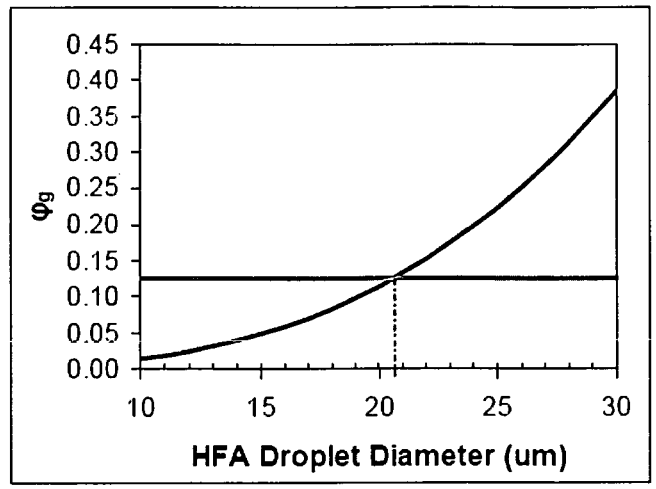
FIG. 24 is a graph of the HFA droplet diameter.
Figures 26, 27:
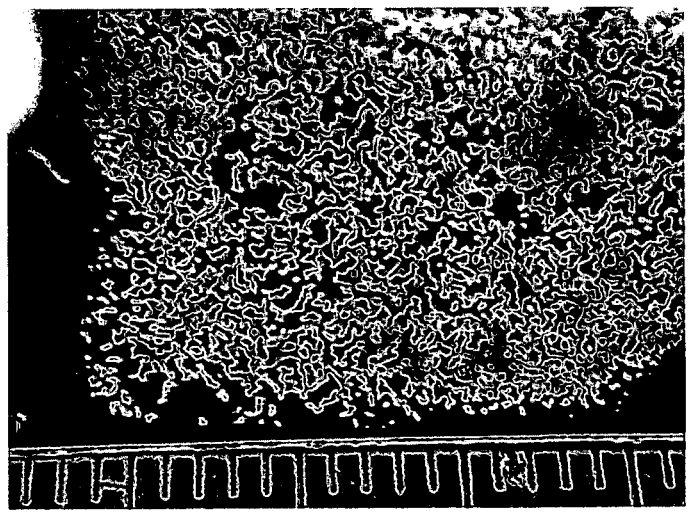
FIG. 26 is an illustration of the calculation of the settling velocities of flocs.
FIG. 27 is a SEM image of TFF particles in HPFP.
Figure 28:
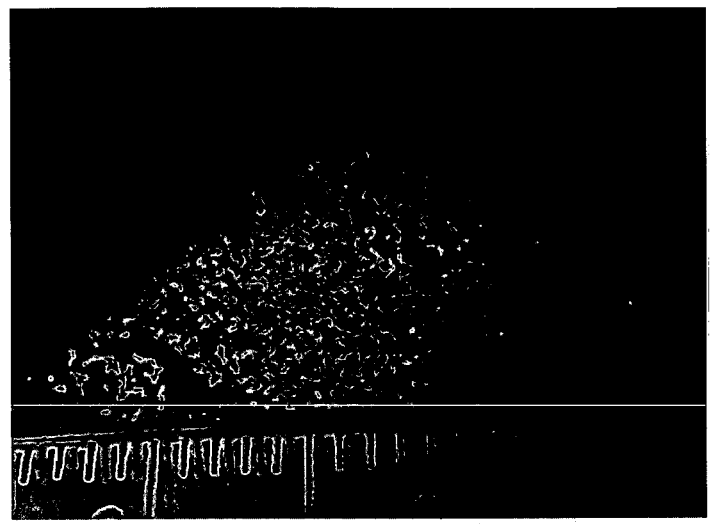
FIG. 28 is a SEM image of CP Itz particles in HPFP.
Figure 29:
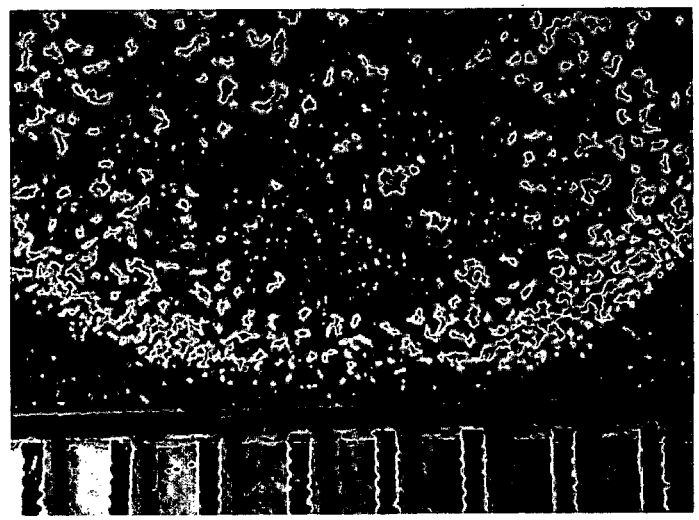
FIG. 29 is a SEM image of DOW amorphous in HPFP.
Figure 32:
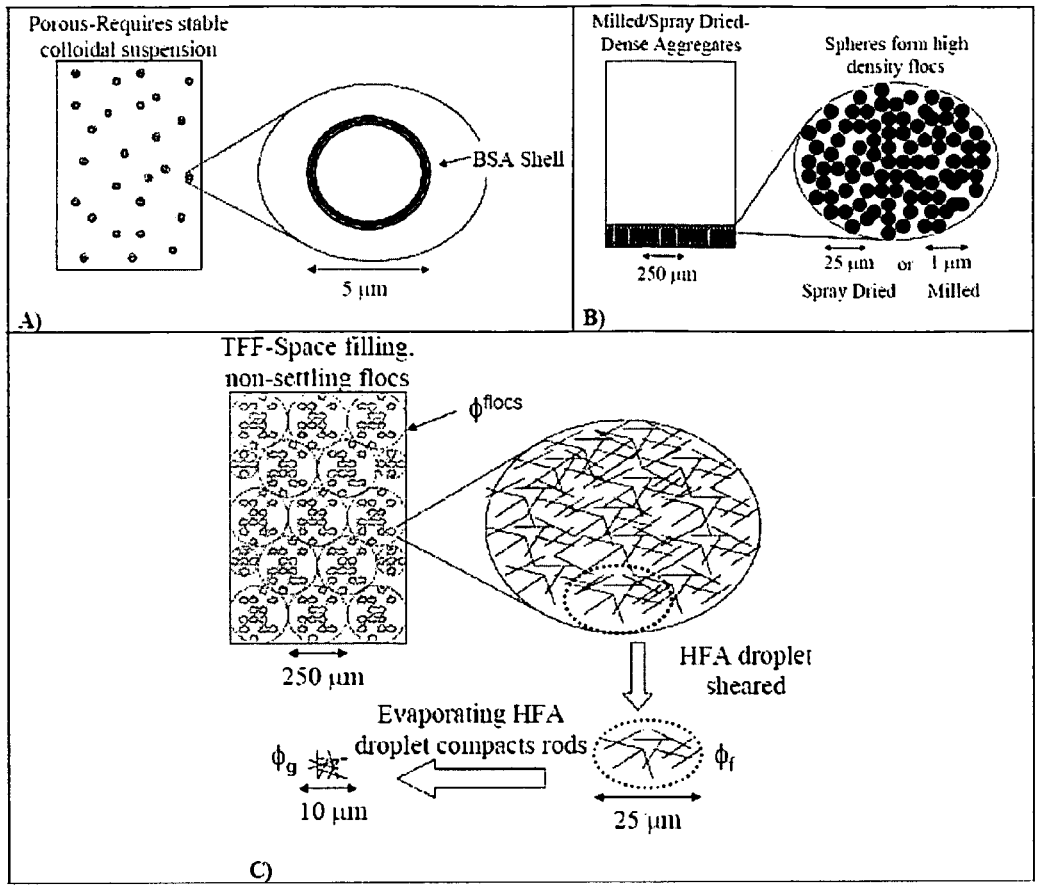
FIGS. 32A-32C are schematics of particle suspension of hollow sphere particles (32A), milled or sprayed particles (32B) and TFF rod particles (32C)

FIG. 22 is a table comparing ITZ formulations. FIG. 23 is a table comparing aerosolized particle dimensions of ACI. FIG. 24 is a graph of the HFA droplet diameter. FIG. 25 is an illustration of the calculation of $D_f$. FIG. 26 is an illustration of the calculation of the settling velocities of flocs. FIG. 27 is a SEM image of TFF particles in HPFP. FIG. 28 is a SEM image of CP ITZ particles in HPFP. FIG. 29 is a SEM image of DOW amorphous in HPFP. FIG. 30 is a SEM image of milled ITZ in HPFP. FIG. 31 is a SEM image of milled ITZ in HPFP. FIGS. 32A-32C are schematics of particle suspension of hollow sphere particles (FIG. 32A), milled or sprayed particles (FIG. 32B) and TFF rod particles (FIG. 32C).

Figure 33:
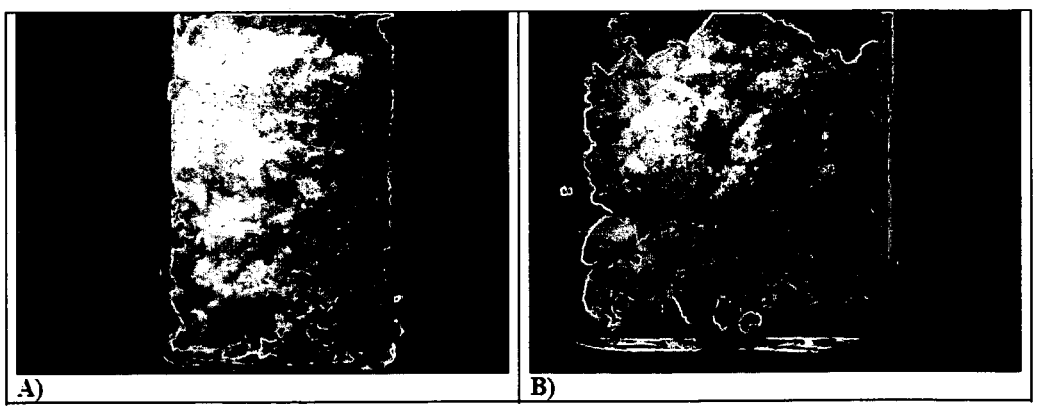
FIGS. 33A-33B are images of TFF particle after lyophilization (33A) and after drying with acetonitrile (33B)
Figure 34:
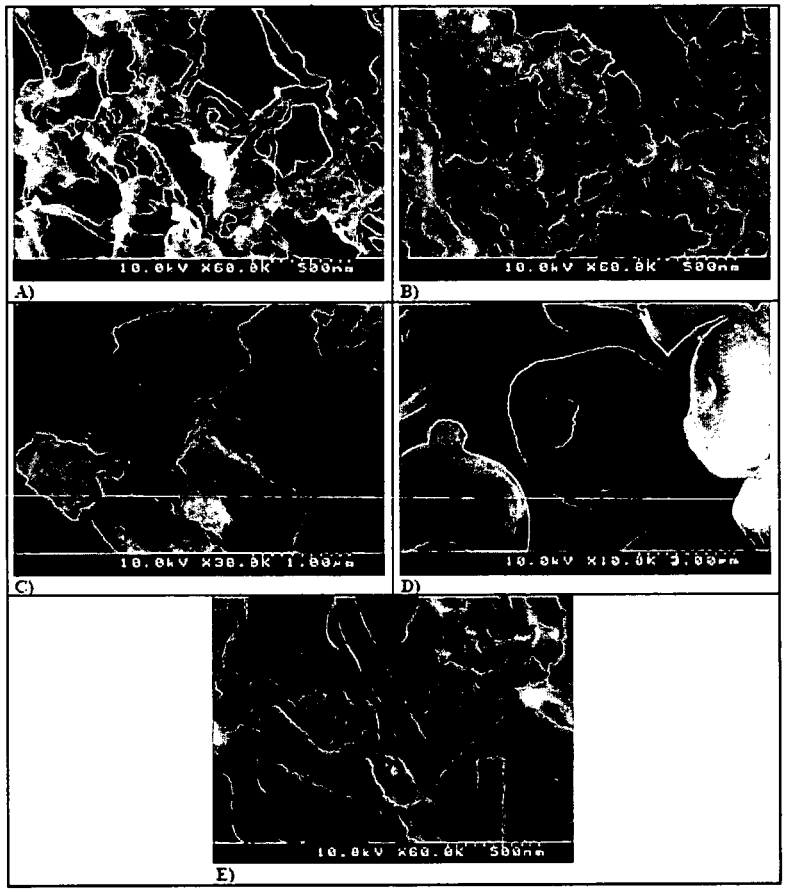
FIG. 34A is an SEM image of BSA particles.
FIG. 34B is an SEM image of BSA:Trehalose.
FIG. 34C is an SEM image of milled BSA particles.
FIG. 34D is an SEM image of spray dried BSA particles.
FIG. 34E is an SEM image of TFF particles drying with acetonitrile.
Figure 35:
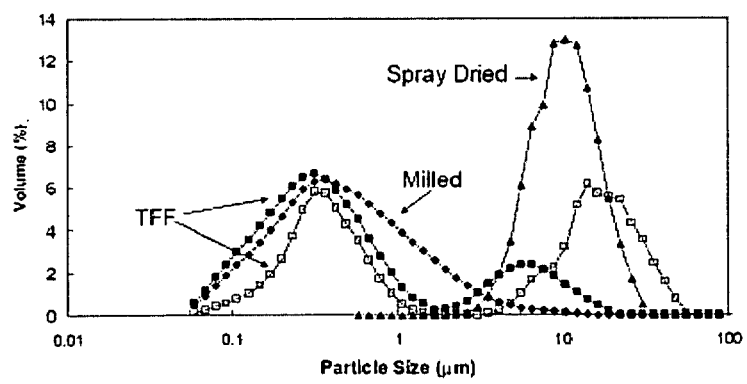
FIG. 35 is a graph of the particle sizes measured by static light scattering for BSA spheres formed by milling and spray drying and BSA nanorods formed by thin film freezing (TFF) suspended in acetonitrile where closed symbols indicate sonicated powder and open circles indicate unsonicated powder.
Figure 36:
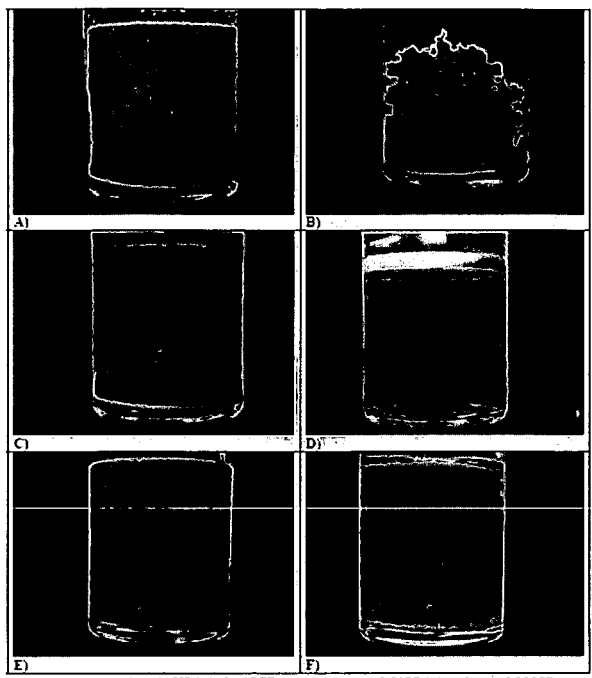
FIG. 36A-36F are images of suspensions in HFA 227 of TFF particles at ($\varphi v$=0.0077 (FIG. 36A), ($\varphi v$=0.00077 (FIG. 36B), milled particles 5 minutes after shaking (FIG. 36C) and spray dried particles at 2 minutes after shaking (FIG. 36D) at ($\varphi v$=0.0077, TFF particles in acetonitrile at ($\varphi v$=0.0077 immediately after shaking (FIG. 36E) and 3 days after shaking (FIG. 36F)

FIGS. 33A-33B are images of TFF particle after lyophilization (33A) and after drying with acetonitrile (FIG. 33B). FIG. 34A is an SEM image of BSA particles, FIG. 34B is an SEM image of BSA:Trehalose, FIG. 34C is an SEM image of milled BSA particles, FIG. 34D is an SEM image of spray dried BSA particles, and FIG. 34E is an SEM image of TFF particles drying with acetonitrile. FIG. 35 is a graph of the particle sizes measured by static light scattering for BSA spheres formed by milling and spray drying and BSA nanorods formed by thin film freezing (TFF) suspended in acetonitrile where closed symbols indicate sonicated powder and open circles indicate unsonicated powder. FIG. 36A-36F are images of suspensions in HFA 227 of TFF particles at $\varphi_v=0.0077$ (FIG. 36A), $\varphi_v=0.00077$ (FIG. 36B), milled particles 5 minutes after shaking (FIG. 36C) and spray dried particles at 2 minutes after shaking (FIG. 36D) at $\varphi_v=0.0077$, TFF particles in acetonitrile at $\varphi_v=0.0077$ immediately after shaking (FIG. 36E) and 3 days after shaking (FIG. 36F).

Figure 37:
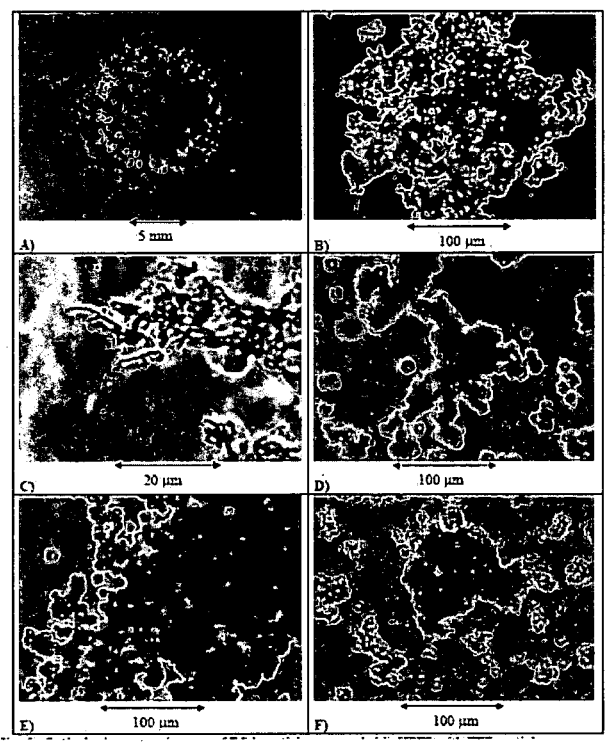
FIG. 37A-37F are optical microscopy images of BSA particles suspended in HPFP with TFF particles magnified 4× (FIG. 37A), 10× (FIG. 37B), and 60× (FIG. 37C), spray dried BSA particles after 30 seconds at 10× (FIG. 37D), after 60 seconds (FIG. 37E), and milled BSA particles after 30 seconds at 10× (FIG. 37F)
Figure 38:
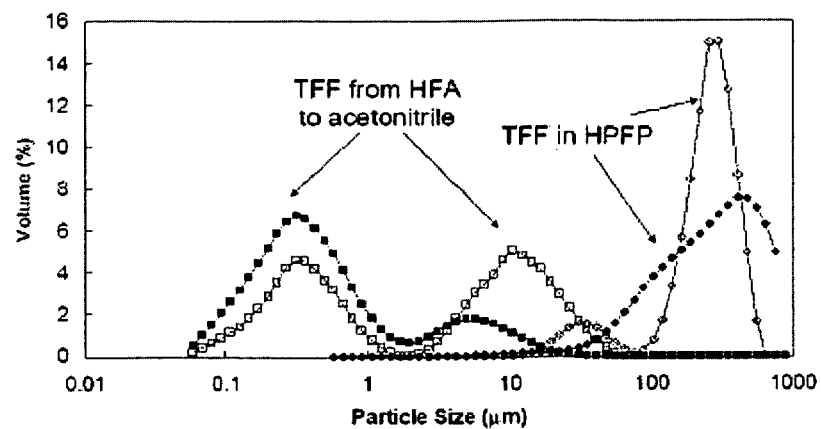
FIG. 38 is a graph of the particle sizes measured by static light scattering for BSA nanorods from thin film freezing (TFF) suspended in HFA 227 or HPFP where closed symbols indicate sonicated powder and open circles indicate unsonicated powder.
Figure 39:
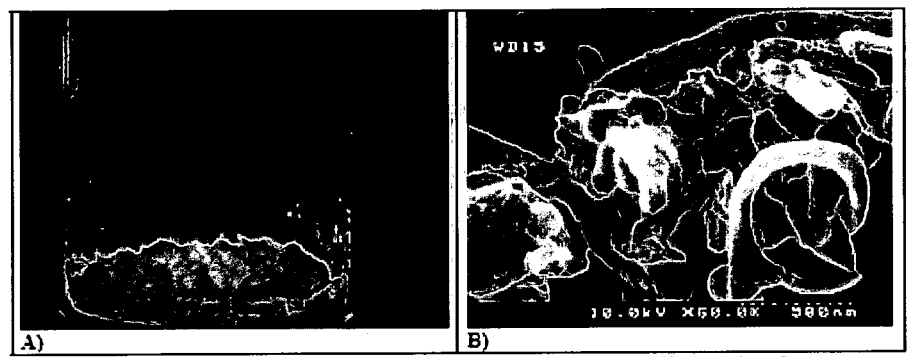
FIG. 39A is an optical image of TFF particles after HFA 227 evaporation and FIG. 39B is an SEM image of TFF particles after sonication and HFA 227 evaporation.
Figure 40:
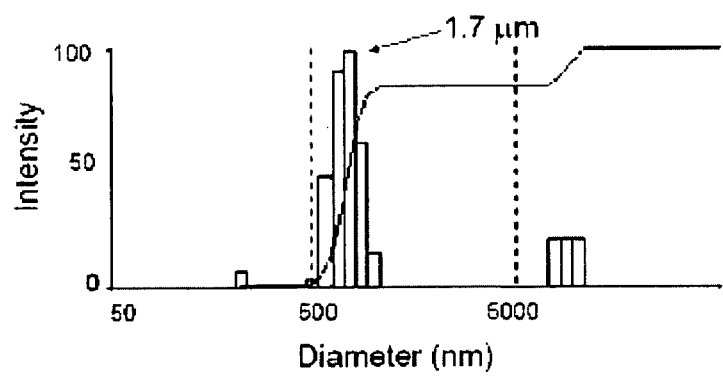
FIG. 40 is a DLS graph of TFF particles actuated through the pMDI valve submerged beneath acetonitrile.
Figure 41:
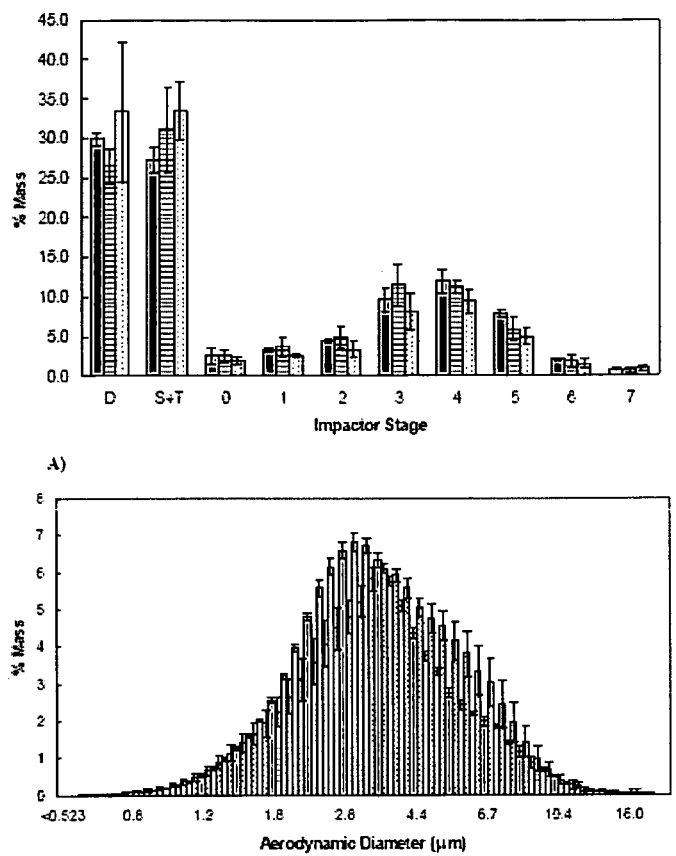
FIG. 41A is a graph of the ACI mass deposition profiles for device (D) and spacer and throat (S+T) and stages 0-7 and FIG. 41B is a graph of the APS mass distribution with a formulations on bar charts include BSA (diagonal lines), BSA+Tween 20 (horizontal lines), and BSA:Trehalose 1:1+ Tween 20 (dotted)

FIG. 37A-37F are optical microscopy images of BSA particles suspended in HPFP with TFF particles magnified 4× (FIG. 37A), 10× (FIG. 37B), and 60× (FIG. 37C), spray dried BSA particles after 30 seconds at 10× (FIG. 37D), after 60 seconds (FIG. 37E), and milled BSA particles after 30 seconds at 10× (FIG. 37F). FIG. 38 is a graph of the particle sizes measured by static light scattering for BSA nanorods from thin film freezing (TFF) suspended in HFA 227 or HPFP where closed symbols indicate sonicated powder and open circles indicate unsonicated powder. FIG. 39A is an optical image of TFF particles after HFA 227 evaporation and FIG. 39B is an SEM image of TFF particles after sonication and HFA 227 evaporation. FIG. 40 is a DLS graph of TFF particles actuated through the pMDI valve submerged beneath acetonitrile. FIG. 41A is a graph of the ACI mass deposition profiles for device (D) and spacer and throat (S+T) and stages 0-7 and FIG. 41B is a graph of the APS mass distribution with a formulations on bar charts include BSA (diagonal lines), BSA+Tween 20 (horizontal lines), and BSA:Trehalose 1:1+Tween 20 (dotted).

Figure 42:
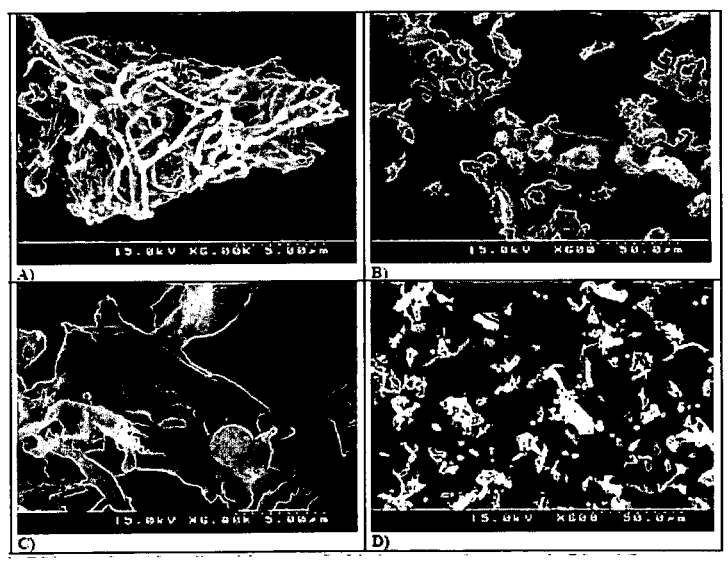
FIG. 42A-42D are SEM images of BSA aerosol collected from stage 3 of Andersen cascade impactor for BSA (FIGS. 42A and 42B) and BSA:Trehalose 1:1 (FIGS. 42C and 42D)

FIG. 42A-42D are SEM images of BSA aerosol collected from stage 3 of Andersen cascade impactor for BSA (FIGS. 42A and 42B) and BSA:Trehalose 1:1 (FIGS. 42C and 42D). FIG. 43 is a table of the dosage and aerodynamic properties of TFF, milled, and spray dried particle suspensions in HFA 227. FIG. 44 is a table of the aerodynamic particle sizes determined by ACI and APS and geometric particle sizes determined by laser diffraction and SEM. FIG. 45 is a table of the calculation of the van der Waals (VdW) interaction potential $\Phi_{vdw}$ of BSA particles in HFA 227.

FIG. 46 is a table of the settling behavior of BSA particles prepared by TFF, milling, and spray drying and calculations for porous shell particles prepared by spray drying, with the [a]Value determined from the equivalent volume of a sphere measured from laser light scattering; [b]The density difference was determined by ρf−ρL with ρp=1.5 g/cm³; [c]Determined from dimensions given by Dellamary et al.; [d]Calculated for primary particle with 100 nm thick shell. FIG. 47 is an optical image of protein pMDI formulations (Lys in HFA 227 with a drug loading of 20 mg/mL, Lys in HFA 134a with a drug loading of 40 mg/mL, 50 mg/mL, 90 mg/mL, and BSA (BSA) in HFA 227 with a drug loading of 50 mg/mL, left to right) 4 hours after shaking. FIG. 48 is a SEM micrograph of aerosolized Lys particles (Lys in HFA 134a pMDI loaded at 50 mg/mL). Aerosolized particles have geometric diameters between 8-10 μm (A) and exhibit porous morphology (B) and (C).

This invention is a new composition of matter by process for producing highly concentrated (about 10-90 mg/mL), suspensions of drugs in pressurized metered dose inhalers (pMDIs). This approach may be used for many types of low molecular weight drugs, and for high molecular weight drugs including peptides and proteins. Dry powders of submicron protein particles produced by thin film freezing, a powder formation process described in manuscripts by Overhoff et. al and Engstrom et. al. (incorporated herein), readily disperse when added to a hydrofluoroalkane propellant to form a stable suspension.

Upon actuation, the submicron protein particles contained within the propellant droplets aggregate to form a porous protein structure (e.g., 8-10 μm) ideal for pulmonary deposition. Pulmonary delivery of proteins is of great interest because the lungs are far more permeable to macromolecules compared to other routes into the body, such as the gastrointestinal (GI) tract, and less invasive than parenteral routes. Furthermore, lung concentrations of metabolizing enzymes are lower than that found in the GI tract and liver.

At concentrations in an HFA of 10 mg/mL achieved emitted and respirable doses of 700 μg and 300 μg per actuation, respectively, of bovine serum albumin (BSA). The new work extends this concept to concentrations of up to 90 mg/mL in HFA 134a. This leads to emitted doses as high as 4 mg/actuation as described below in TABLE 5. One of the primary criticisms levied against pMDI formulations is the upper limit dose that they can deliver, 500-600 μg/dose. Common pMDI doses are 100-300 μg/dose[5]. Thus, a major goal for pMDIs has been to raise the dosage in order to allow for pMDI delivery of less potent actives. TABLE 5: ACI results for different protein pMDI formulations at different protein concentrations. Bovine serum albumin (BSA) and lysozyme (Lys) formulations shown.

| | TED (mg) | FPF (%) | MMAD/GSD |
|---|---|---|---|
| BSA (50 mg/mL)* | 2.59 ± 0.44 | 64 ± 3 | 2.48 ± 0.22/3.89 ± 0.11 |
| Lys (20 mg/mL)* | 3.97 ± 0.825 | 64 ± 9 | 2.49 ± 0.18/4.33 ± 0.59 |
| Lys (50 mg/mL)** | 3.81 | 62 | 2.62/3.56 |
| Lys (70 mg/mL)** | 3.35 | 60 | 2.72/3.00 |

*HFA 227
**HFA 134a

To prepare the protein pMDI formulations, the protein powders are placed in 50 mL PYREX® beakers and pre-cooled in a −80° C. freezer. The propellant, preferably a hydrofluoroalkane propellant, is pre-cooled to −80° C. and then poured into the beaker containing the protein powders to form suspensions ranging in concentrations from 0.7-7.4% w/w. The resultant protein suspensions are placed in a dry ice/acetone bath and sonicated for two minute using a Branson Sonifier 450 (Branson Ultrasonics Corporation, Danbury, CT) with a 102 converter and tip operated in pulse mode at 35 W. 11 mL of the cooled protein formulations are dispensed into 17 mL glass aerosol vials (SGD, Paris, France) and fitted with metering valves containing 100 μL metering chambers (DF10 RC 150, Valois of America, Inc., Congers, NY) using a compressor pump (Pamasol Model P2005, Pfaffikon, Switzerland). The vials are allowed to warm up to room temperature. Small amounts of lubricants (2-8% w/w), such as polysorbate 20 and polysorbate 80, may be added to the formulation prior to sonication to minimize clogging of the valve during actuation due to the highly concentrated suspensions.

The highly concentrated protein pMDI's demonstrate desirable aerodynamic properties ideal for pulmonary drug delivery. Impaction studies were conducted with a non-viable eight-stage cascade impactor (Thermo-Andersen, Smyrna, GA) with an attached Aerochamber Plus® Valved Holding Chamber (Trudell Medical International, London, Ontario, Canada) at a flow rate of 28.3 L/min to quantify total emitted dose (TED), fine particle fraction (FPF), mass median aerodynamic diameter (MMAD), and geometric standard deviation (GSD). FPF was defined as the percentage of particles with an aerodynamic diameter less than 4.7 μm. Three actuations are expelled as waste prior to measurements. One actuation is made into the ACI for analysis. The valve stem, actuator, and impactor components are placed into separate containers with a known volume of deionized (DI) water. Each component soaks for at least 30 minutes to ensure complete protein dissolution. The protein concentrations are quantitated with a Micro BCA Protein Assay manufactured by Pierce (Rockford, IL). The absorbance of the solutions was measured at 562 nm using the μQuant Model MQX200 spectrophotometer (Biotek Instruments Inc., Winooski, VT). Untreated protein was used to prepare the protein standards at concentrations between 2 and 40 μg/mL. ACI results yielded average TED's between 2.5-4.0 mg protein/actuation, average FPF's between 56-64%, and average MMAD's between 2.5-2.8 (GSD's between 3.0-3.9).

The ability of a pMDI to deliver a consistent dose is mandatory for the delivery of sufficient and safe drug doses to patients. Thus, stable pMDI suspensions are desired to ensure dose uniformity. No visible creaming or settling was observed for the suspensions over 48 hours. FIG. 47 is an optical image of protein pMDI formulations (Lys in HFA 227 with a drug loading of 20 mg/mL, Lys in HFA 134a with a drug loading of 40 mg/mL, 50 mg/mL, 90 mg/mL, and BSA (BSA) in HFA 227 with a drug loading of 50 mg/mL, left to right) 4 hours after shaking.

Dose uniformity of the highly concentrated protein pMDI's is demonstrated by actuating the pMDI through the firing adaptor of a dosage unit sample tube (26.6×37.7×103.2 mm; 50 mL volume; Jade Corporation, Huntingdon, PA). A known volume of DI water is added to dissolve the protein and the sampling tube is shaken and allowed to sit for at least 30 minutes to ensure complete protein dissolution. The protein concentration is determined using the Micro BCA protein assay in conjunction with the μQuant spectrophotometer. The pMDI canister is weighed before and after each actuation to assure that the proper dose was released.

TABLE 6 is a table of the dose uniformity results for different protein pMDI formulations at different protein concentrations. % Theoretical is the percentage of the theoretically loaded dose that is emitted during actuation.

TABLE 6

| | DDV (mg/actuation)/% Theoretical |
|---|---|
| BSA (50 mg/mL)* | 3.65 ± 0.37/73 |
| Lys (20 mg/mL)* | 1.03 ± 0.058/~50 |
| Lys (40 mg/mL)** | 3.44 ± 0.286/~86 |
| Lys (50 mg/mL)** | 4.11 ± 0.110/~82 |
| Lys (70 mg/mL)** | 4.35 ± 0.274/~62 |
| Lys (90 mg/mL)** | 2.94 ± 0.286/~33 |

*HFA 227
**HFA 134a

Further characterization of protein particles after aerosolization from the pMDI device is performed. The aerosolized particles are measured by laser light scattering. Each formulation is actuated once through the ACI spacer and throat. The aerosol exits the outlet of the throat about 5 cm above the laser of the Malvern Mastersizer S (Malvern Instruments, Ltd., Worcestershire, UK). For each formulation 100 measurements of the aerosolized spray are made about every 5 ms. The recorded measurements are averaged to give a final profile of the aerosolized particles on a volume basis. Scanning electron microscopy (SEM) images of aerosolized particles are also used to determine the size of aerosolized particles. Particles are collected from stage 3 of the ACI. Double carbon adhesive tape is applied to stage 3. The impaction test is conducted according to the parameters mentioned earlier and the carbon tape is applied to an aluminum SEM stage. The sample is sputter coated with gold-palladium for 30 seconds using a K575 sputter coater (Emitech Products, Inc., Houston, TX). Micrographs are taken using a Hitachi S-4500 field emission scanning electron microscope (Hitachi Ltd., Tokyo, Japan) at an accelerating voltage of 5-10 kV. Particle images are sized on the SEM micrographs using imaging software (Scion, Frederick, MD). At least 50 particles were measured for each formulation. Particle sizes from the SEM micrographs correlate well with sizes reported by laser light scattering.

FIG. 48 is a SEM micrographs of aerosolized Lys particles (Lys in HFA 134a pMDI loaded at 50 mg/mL). Aerosolized particles have geometric diameters between 8-10 μm (A) and exhibit porous morphology (B) and (C). Other formulations show similar morphologies. Aerosolized particle densities are also determined from the SEM micrographs. The calibrated aerodynamic diameter of particles deposited on stage 3 of the ACI is 3.3-4.7 μm. Thus an average MMAD of 4.0 μm was assumed for particles deposited on stage 3 of the ACI. Using the relationship, $d_a = d_g(\rho_g/\rho_a)^{0.5}$ (where $d_a$ is the aerodynamic diameter, $d_g$ is the geometric diameter, $\rho_g$ is the density of the particle, and $\rho_a$ is 1 g/cm$^3$) and using the estimated MMAD and geometric diameter (from the SEM micrographs), the density of the aerosolized particle is calculated. The low calculated densities (0.14-0.23 g/cm$^3$) indicate that the aerosolized particles are highly porous, which is expected because of the porous morphology observed in the SEM micrographs. The low densities explain why the particles are able to reach deep lung levels despite a geometric diameter of 8-10 μm.

TABLE 7 is a table that illustrates the measured particle diameters for aerosolized protein particles. $D_{v,50}$ (diameter at which the cumulative sample volume was under 50%) values were reported by Malvern.

|  | $D_{v,50}$ (μm) | SEM Volume Average Diameter (μm) | ρ (g/cm$^3$) |
| --- | --- | --- | --- |
| BSA (50 mg/mL)* | 10.05 ± 0.01 | 10.75 ± 2.07 | 0.14 |
| Lys (20 mg/mL)* | 8.07 ± 0.06 | 8.67 ± 2.00 | 0.21 |
| Lys (50 mg/mL)** |  | 8.78 ± 1.68 | 0.21 |
| Lys (70 mg/mL)** |  | 8.41 ± 1.70 | 0.23 |

*HFA 227
**HFA 134a

Preparation of TFF ITZ particles. ITZ (about 500 mg, Hawkins, Inc., Minneapolis, MN) was dissolved in about 40 mL of 1,4-dioxane (Fisher Chemicals, Fairlawn, NJ). To the drug solution, 100 mL of t-butanol (Fisher Chemicals, Fairlawn, NJ) was added. The ITZ in 1,4 dioxane-t-butanol drug solution was passed at a flow rate of 4 mL/min through a 17 gauge (1.1 mm ID, 1.5 mm OD) stainless steel syringe needle. The droplets fell from a height of 10 cm above a rotating stainless steel drum (12 rpm) 17 cm long and 12 cm in diameter. The hollow stainless steel drum was filled with dry ice to maintain a drum surface temperature of about 223 K. On impact, the droplets deformed into thin films and froze. The frozen thin films were removed from the drum by a stainless steel blade and transferred to a 400 mL PYREX® beaker filled with liquid nitrogen. The excess liquid nitrogen was evaporated in a −80° C. freezer. A Virtis Advantage Lyophilizer (The Virtis Company, Inc., Gardiner, NY) was used to dry the frozen slurries. Primary drying was carried out at −30° C. for 36 hours at 300 mTorr and secondary drying at 25° C. for 24 hours at 100 mTorr. A 12 hour linear ramp of the shelf temperature from −30° C. to +25° C. was used at 100 mTorr.

Figure 49:
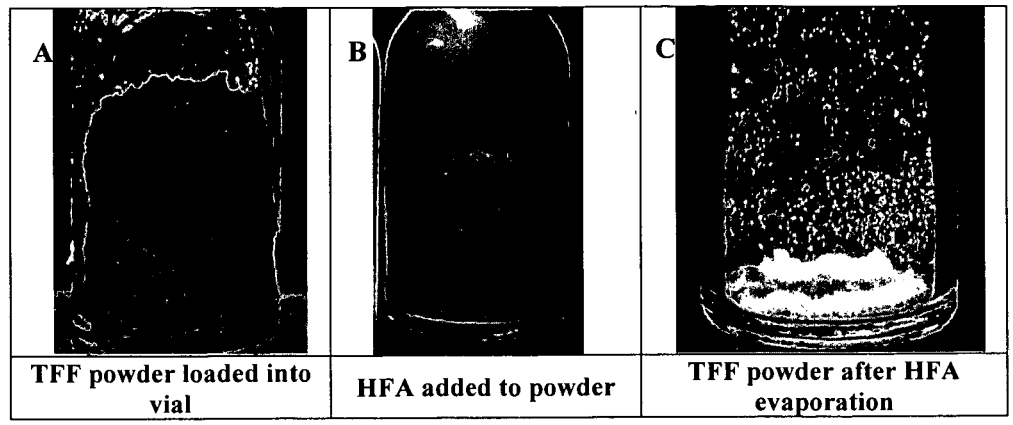
FIG. 49A is a photograph of 110 mg TFF ITZ powder loaded into a glass vial.

Crystallization of TFF ITZ particles: FIGS. 49A-49C are optical images of the TFF ITZ particles (about 110 mg) were loaded as dry powder into glass vials (SGD, Paris, France) and fitted with metering valves (DF10 RC 150, Valois of America, Inc., Congers, NY) using a Pamasol Model P2005 compressor pump (Pamasol Willi Mader AG, Pfaffikon, Switzerland) (FIG. 49A). FIG. 49A is a photograph of 110 mg TFF ITZ powder loaded into a glass vial. FIG. 49B is a photograph of a 10 mg/mL TFF ITZ suspension produced after addition of 11 mL of HFA 227 to FIG. 49A, and FIG. 49C is a photograph of 110 mg TFF ITZ powder after exposure to HFA 227. 1,1,1,2,3,3,3-heptafluoropropane (HFA 227, Solvay, Greenwich, CT) was loaded into the vials containing drug using Pamasol filling equipment (Model P2008) to yield a 10 mg/mL milky suspension (FIG. 49B). The pressurized suspensions may be referred to as pressurized metered dose inhalers (pMDIs). To collect TFF ITZ powder after HFA exposure, the pMDI was cooled in a −80° C. freezer, well below the HFA 227 boiling point of −16° C. Once the HFA was sufficiently cooled, the metering valve was removed and the HFA was allowed to warm in a dry box (relative humidity <20%) until it completely evaporated (FIG. 49C). Exposure of TFF ITZ powder to 2H,3H perfluoropentane (HPFP), a non-volatile surrogate for HFA 227, was also studied.

Product Description and Characterization: Sub-micron amorphous particles of a poorly water soluble drug, itraconazole (ITZ), were produced by thin film freezing (TFF), a particle formation process described in manuscripts by Engstrom et al. and Overhoff et al.

Figure 50:
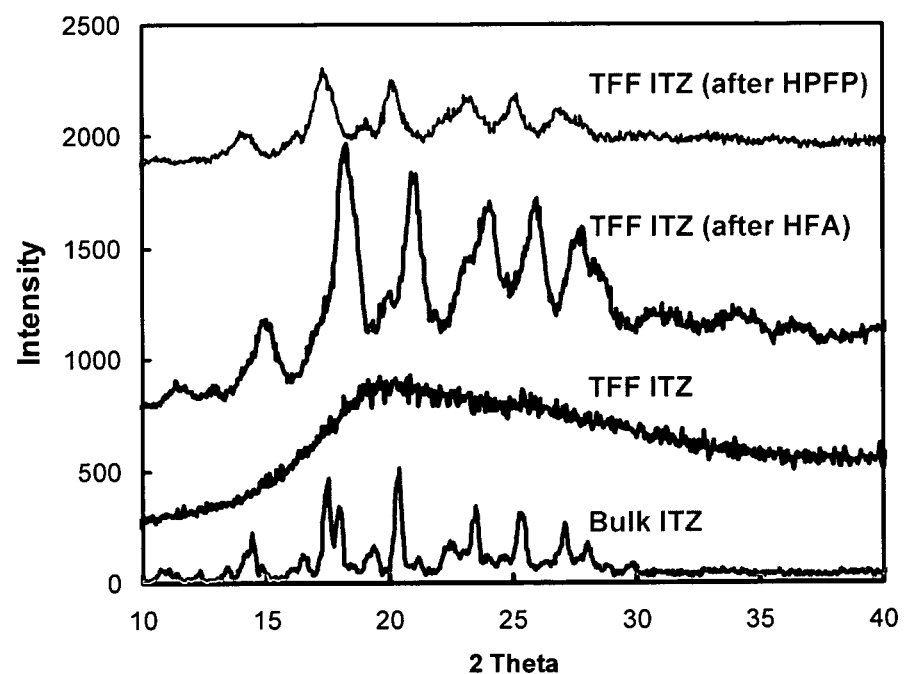
FIG. 50 is a graph of the X-ray diffraction (XRD) pattern of ITZ before and after exposure to HFA 227.
Figure 51:
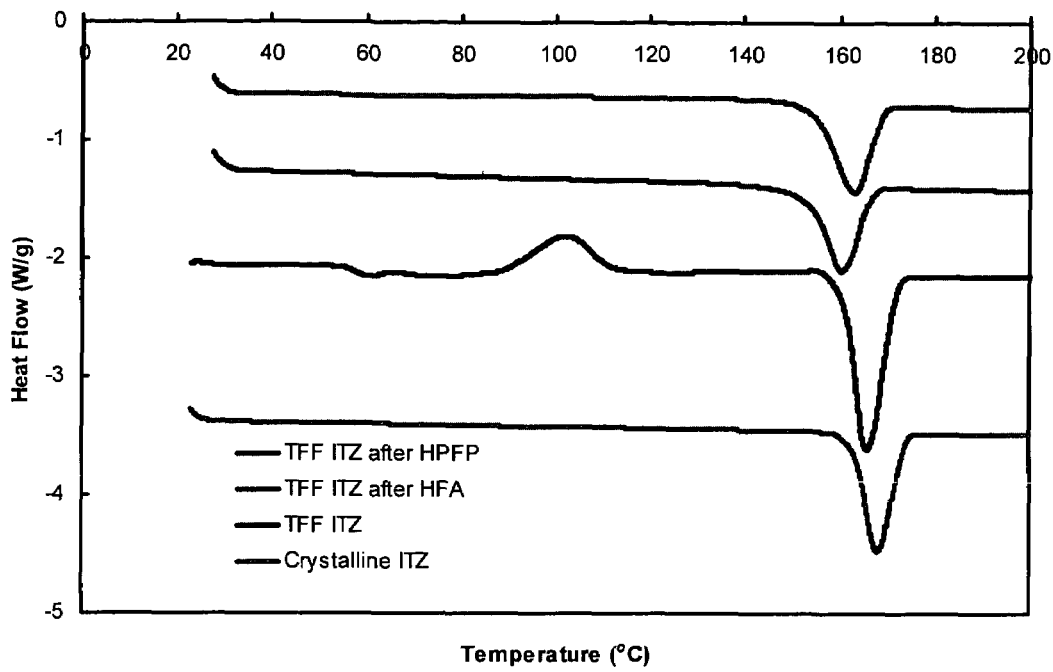
FIG. 51 is a graph of the Modulated differential scanning calorimetry (mDSC) of TFF ITZ powders before and after exposure to HFA 227 and HPFP and pure ITZ.

FIG. 50 is a graph of the X-ray diffraction (XRD) pattern of ITZ before and after exposure to HFA 227. Crystallization of TFF ITZ particles after HFA exposure was determined using x-ray diffraction (XRD) and differential scanning calorimetry (DSC). XRD patterns and DSC scans of TFF ITZ powder before contact with HFA were characteristic of amorphous materials (FIGS. 50-51). However, characteristic peaks of crystalline ITZ were detected in the XRD profile after TFF ITZ particles were exposed to HFA 227 (FIG. 50).

FIG. 51 is a graph of the Modulated differential scanning calorimetry (mDSC) of TFF ITZ powders before and after exposure to HFA 227 and HPFP and pure ITZ. DSC scans showed complete crystallization of the TFF ITZ particles after exposure to HFA 227, based on the absence of an endothermic recrystallization peak (FIG. 51). Similar results were obtained after exposure of TFF ITZ particles to HPFP (FIGS. 50-51). These results are significant because crystallization of TFF ITZ may be induced with a solvent that can be handled under atmospheric conditions.

Figure 52:
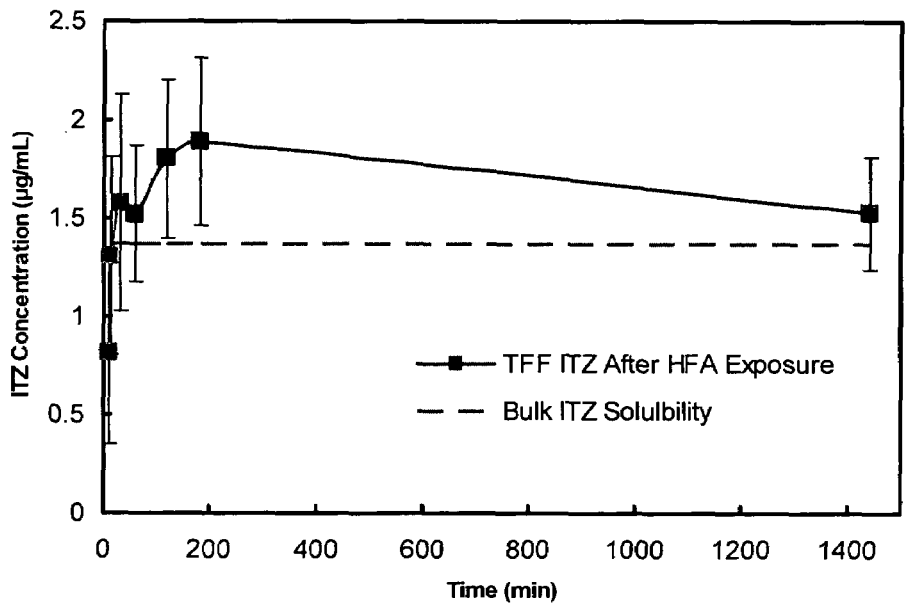
FIG. 52 is a graph of the dissolution profile of TFF ITZ particles after exposure to HFA 227 conducted in pH 7.4 phosphate buffer (0.02% w/v SDS)

To confirm the complete crystallization of TFF ITZ particles after exposure to HFA, dissolution studies were conducted on the HFA-exposed TFF ITZ powder in pH 7.4 phosphate buffer (0.02% w/v SDS). The equilibrium solubility of crystalline ITZ in the dissolution media was experimentally determined to be 1.4 μg/mL. HFA-exposed TFF ITZ powder (1 mg) was added to 50 mL of dissolution media to yield an initial drug loading of 20 μg/mL. Sample aliquots (1.5 mL) were taken from the dissolution vessels at various time points. The aliquots were filtered immediately using a 0.2 μm syringe filter. Dissolved drug levels did not significantly exceed equilibrium solubility of crystalline ITZ, suggesting that the HFA-exposed TFF ITZ particles were crystalline (FIG. 52). FIG. 52 is a graph of the dissolution profile of TFF ITZ particles after exposure to HFA 227 conducted in pH 7.4 phosphate buffer (0.02% w/v SDS). TFF ITZ powder that had been previously exposed to HFA 227 (1 mg) was added to the dissolution media (50 mL) to achieve an initial loading of 20 μg ITZ/mL. All samples were filtered with 0.2 μm pore size filters. The dashed line represents the solubility of "as received" ITZ in the dissolution media.

Figure 53:
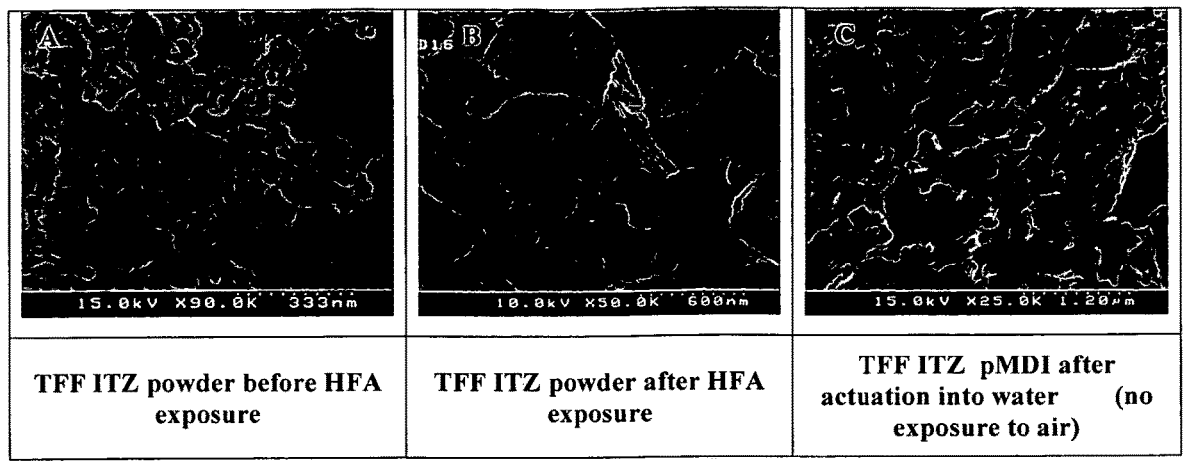
FIGS. 53A, 53B and 53C are scanning electron microscopy images of TFF ITZ (FIG. 53A) before and (FIG. 53B) after exposure to HFA 227 and (FIG. 53C) SEM image of TFF ITZ after pMDI was actuated into water, without any exposure to air.

FIG. 53 in a scanning electron microscopy (SEM) images of TFF ITZ (FIG. 53A) before and (FIG. 53B) after exposure to HFA 227 and (FIG. 53C) SEM image of TFF ITZ after pMDI was actuated into water, without any exposure to air. Additionally, a change in morphology of the TFF ITZ particles before and after exposure to HFA 227 was detected by scanning electron microscopy (FIG. 53A-53B). TFF ITZ particles prior to HFA contact were spherical in shape. However, thin, plate-like structures were observed after exposure to HFA. To further verify that the crystallization of TFF ITZ was induced by HFA, a pMDI containing TFF ITZ was actuated into water, with the metering valve submerged below the liquid level, to produce a slightly turbid dispersion. The TFF ITZ particles emitted from the pMDI were collected by freezing and lyophilizing this dispersion. SEM images of the actuated TFF ITZ particles revealed thin, plate-like structures strongly resembling the particles produced after HFA evaporation (FIG. 53C). Therefore, complete crystallization of amorphous TFF ITZ particles occurred upon exposure to HFA 227.

Figure 54:
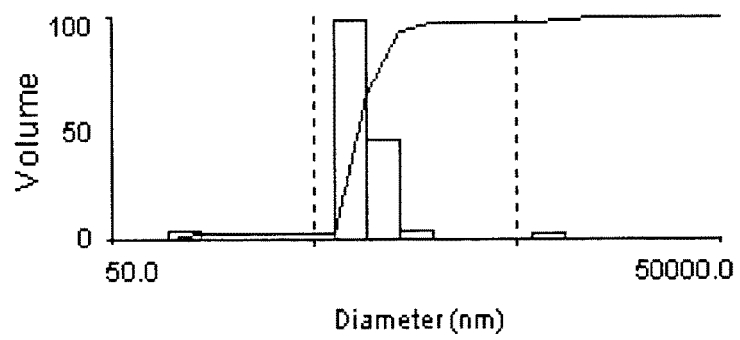
FIG. 54 is a graph of the dynamic light scattering (DLS) measurements of HFA-exposed TFF ITZ in water.

FIG. 54 is a graph of the dynamic light scattering (DLS) measurements of HFA-exposed TFF ITZ in water. The sizes of 66% of the particles (by volume) were 737 nm or less. Furthermore, dynamic light scattering (DLS) measurements show that TFF ITZ particle dimensions remained below 1 μm after crystallization, with 66% of the particles by volume with a hydrodynamic radius of 737 nm or less (FIG. 54).

Production of TFF ITZ/BSA compositions. Two compositions using a 10/1 and 5/1 ITZ/BSA ratios were formulated to demonstrate that a water soluble component could be added to the poorly water soluble TFF ITZ to aid in wetting during dissolution. A 5 mg/mL loading was tested. The resultant pMDI formulations were milky, white and uniform, and similar to the other TFF pMDIs.

Table 8 shows the results obtained from the Andersen Cascade Impactor.

|  | Respriable Dose/Act (μg) | % FPF | MMAD (μm) |
| --- | --- | --- | --- |
| TFF Itz (10 mg/mL) | 525 ± 23 | 56 ± 3 | 3.8 ± 0.3 |
| Milled Itz 300 nm (10 mg/mL) | 29 ± 8 | 15 ± 3 | 6.0 ± 0.7 |
| TFF Itz/BSA (10/1) (5 mg/mL) | 238 ± 5 | 67 ± 2 | 1.4 |
| TFF Itz/BSA (5/1) (5 mg/mL) | 302 | 70 | 1.5 |

FIG. 55A shows the scanning electron microscopic image of aerosolized TFF ITZ and FIG. 55B shows the SEM image of the aerosolized TFF ITZ in dissolution media at 37° C. after 1 minute. The study was conducted in phosphate buffer pH 7.4 containing 0.2% w/v SDS.

FIG. 56 is a plot showing the dissolution profiles of aerosolized TFF ITZ and aerosolized milled ITZ particles (300 nm) studied in phosphate buffer (pH=7.4) containing 0.2% w/v SDS at 37° C. The graph shows a much more rapid dissociation and dissolution of the aerosolized aggregate into constituent particles in comparison to the milled ITZ particles.

The flocculated particles used for pMDI delivery may also be applicable for dry powder inhalation. In a dry powder inhaler, shear forces generated during inspiration break up the flocs to an appropriate aerodynamic size for deep lung delivery. The particles may be produced by either milling, controlled precipitation (CP), or TFF. Poorly water soluble drugs, itraconazole (ITZ) and cyclosporine A (CsA), and water soluble proteins, bovine serum albumin (BSA) and lysozyme (lys), were the model drugs used to demonstrate DPI delivery of nanoparticles produced by CP and TFF. Drug powders were aerosolized and characterized using either an Aerosizer/Aerodisperser (TSI, Shoreview, MN) or an APS 3321/3343 (TSI, Shoreview, MN) disperser.

Figures 57, 58:
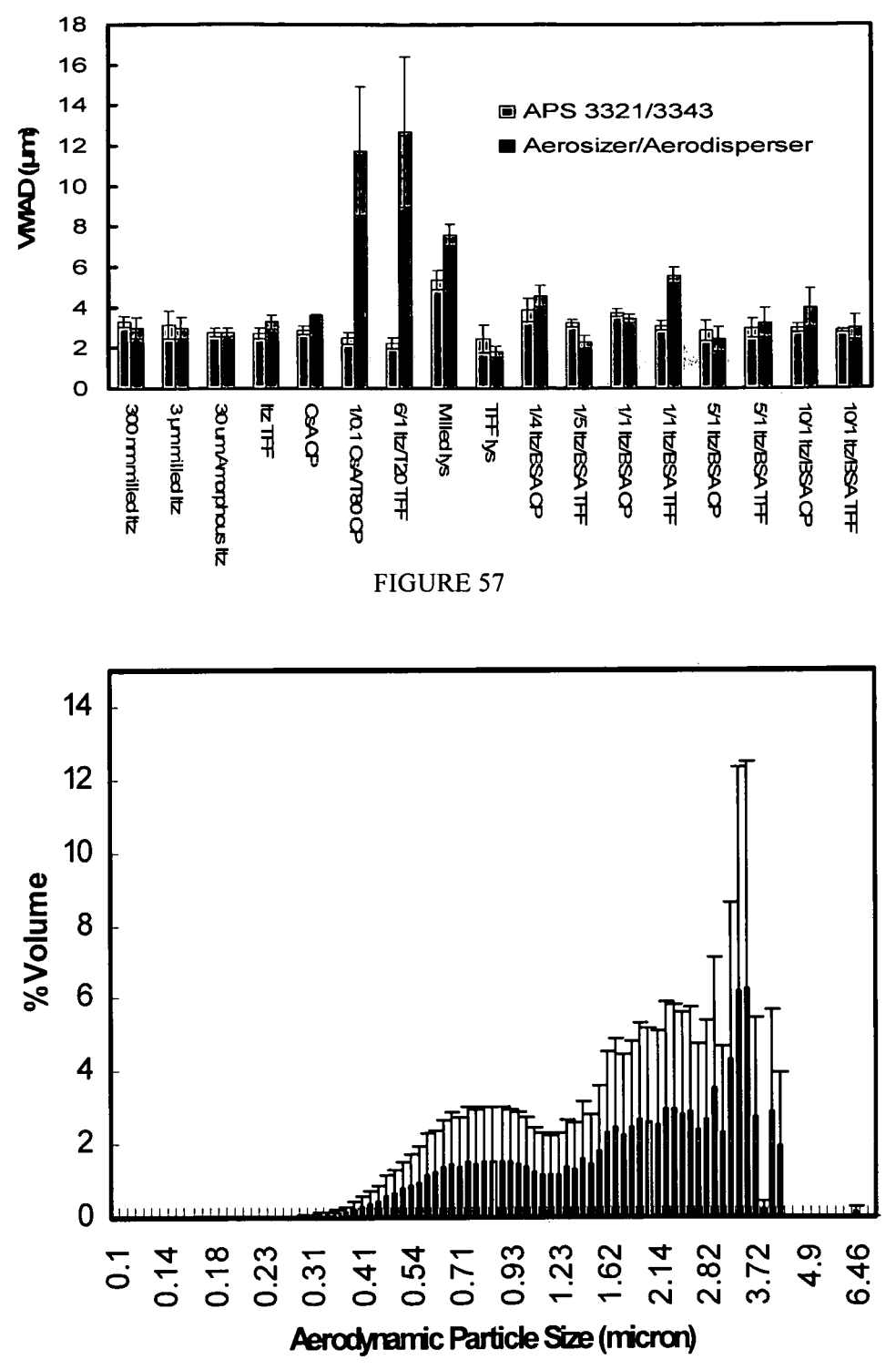

FIG. 57 is a graph of the aerodynamic diameters of milled, TFF, and CP drug compositions measured by the APS 3321/3343 and the Aerosizer/Aerodisperser systems. VMAD is the volume mean aerodynamic diameter. The drug compounds studied include the poorly water soluble drugs itraconazole (ITZ) and cyclosporine A (CsA), as well as bovine serum albumin (BSA) and lysozyme (lys). T80 and T20 are the surfactants tween 80 and tween 20 (Sigma Chemical, St. Louis, MO).

The aerosolized CP and TFF powders possessed aerodynamic diameters predominantly between 2.0-3.5 μm, on a volume basis, ideal for pulmonary delivery, as seen in FIG. 57. These diameters are in a range that is known to be desirable for efficient deep lung delivery. Furthermore, the sizes are in good agreement for the two dispersers. Only two compositions containing low melting point stabilizers, such as Tween surfactants, possessed aerodynamic diameters larger than 8 μm. Compositions containing both a poorly water soluble drug (Itz) and a protein (BSA) were also shown to yield optimal aerosol particles for pulmonary delivery.

FIG. 58 is a graph of the aerodynamic particle size distribution for the TFF lys composition. VMAD is the volume averaged mean aerodynamic diameter and GSD is the geometric standard deviation.

An example of the aerodynamic particle size distribution for the aerosolized particles is shown in FIG. 58 for the aerosolized TFF lys formulation. SEM micrographs of TFF lysozyme powder before aerosolization and after aerosolization are shown in FIGS. 59A-C. Lysozyme particles produced by TFF have a morphology of small nanorods, with lengths ~500 nm and diameters between ~50-100 nm, as seen in FIGS. 59A-C. Aerosolization of the powder disperses the nanorod floc to yield aerosol particles roughly 3 micron in diameter. High magnification images of the aerosolized particles show that the rod-shaped primary particles are maintained throughout the aerosolization process. The SEM micrographs of the aerosolized TFF lys particles were obtained by placing ~25 mg of powder in gallon sized Ziploc bag. Double sided carbon tape was placed onto the inside of the bag. The opening of the bag was then rubber banded around the nozzle of a can of compressed air. A short burst of air was actuated into the bag to disperse the powder. The carbon tape was removed from the inside of the bag and placed onto an SEM stage for microscopy.

As used herein, the term "surfactant" means a substance that reduces the surface tension of a liquid, thereby causing it to spread more readily on a solid surface. Examples of surfactants for use with the present invention, include, all surfactants suitable for administration to the lungs, including sodium salts of cholate, deoxycholate, glycocholate and other bile salts; Span 85@, (sorbitan trioleate), lauryl-beta-D-maltoside, palmitic acid, glycerol trioleate, linoleic acid, DPPC oleyl alcohol, oleic acid, sodium oleate, and ethyl oleate.

Non-limiting examples of the active agents of the present invention includes antifungal agents having one or more of azoles and/or allylamines, e.g., natamycin, flucytosine, miconazole, fluconazole, itraconazole, clotrimazole, econazole, miconazole, ravuconazole, oxiconazole, sulconazole, terconazole, tioconazole, fenticonazole, bifonazole, oxiconazole, ketoconazole, isoconazole, tolnaftate, amorolfine, terbinafine, voriconazol, posaconazol, or the pharmacologically acceptable organic and inorganic salts or metal complexes or mixture thereof.

Delivery of the present invention to the lung can be achieved through any suitable delivery means, including a nebulizer, a dry powder inhaler, a metered dose inhaler or a pressurized metered dose inhaler. The suitable delivery means will depend upon the active agent to be delivered to the lung, the desired effective amount for that active agent, and characteristics specific to a given patient.

In addition, the present invention may include one or more excipients that modify the intended function of the effective ingredient by improving flow, or bio-availability, or to control or delay the release of the effective ingredient, e.g., nonlimiting examples include: Span® 80 (sorbitan oleate), Tween® 80 (polysorbate 80), Brij® 35 (polyethoxylate lauryl ether), Brij® 98 (polyoxyethylene (20) oleyl ether), Pluronic® (poloxamers), Sucroester® 7 (sucrose distearate), Sucroester® 11 (sucrose mono/distearate), Sucroester® 15 (sucrose monopalmitate), sodium lauryl sulfate, oleic acid, laureth-9 (polidocanol), laureth-8 (sodium lauryl polyoxyethylene ether sulfate), lauric acid, vitamin E TPGS (tocopherol polyethylene glycol succinate), Gelucire® 50/13 (stearoyl macrogol-32 glycerides), Gelucire® 53/10 (polyoxyethylene glycol-32 glyceryl stearate (PEG-32 glyceryl stearate)), Labrafil® (oleoyl polyoxyl-6 glyceride), dipalmitoyl phosphadityl choline, glycolic acid and salts, deoxycholic acid and salts, sodium fusidate, cyclodextrins, polyethylene glycols, Labrasol® (caprylocaproyl polyoxyl-8 glycerides), polyvinyl alcohols, polyvinyl pyrrolidones and tyloxapol, cellulose derivatives, and polyethoxylated castor oil derivatives.

Other suitable solvents include but are not limited to: ethanol, methanol, tetrahydrofuran, acetonitrile, acetone, tert-butyl alcohol, dimethyl sulfoxide, N,N-dimethyl formamide, diethyl ether, methylene chloride, ethyl acetate, isopropyl acetate, butyl acetate, propyl acetate, toluene, hexanes, heptane, pentane, 1,3-dioxolane, isopropanol, n-propanol, propionaldehyde and combinations thereof.

The preparation of particles and respirable aggregates using a URF method includes a solution of ITZ (0.0798 g) with Pluronic® F-127 (poloxamer 407) (0.0239 g) is prepared by loading the dry solids into a vial. A prepared 95/5 wt % blend of t-butanol and toluene (10.03 g) is loaded into the vial. The resulting slurry is heated until a solution was formed. (68 to 70° C.). The resulting solution is applied to the freezing surface of the URF unit, which had been cooled to −78° C. over a three-minute time period. The frozen solvent, drug, and excipient matrix is collected in a tray, which had been cooled with dry ice, and transferred into a 60-mL jar, which had been cooled with dry ice. The jar containing the URF processed frozen solid is then placed on a freeze drying unit and lyophilized for approximately 17 hr at 100 mtorr. After lyophilization, 0.0700 g of the URF processed solid is recovered as a dry flowable powder. The mean volume average particle sizes (with and without sonication) of the reconstituted drug particles are measured using a Coulter LS 230. The particles are amorphous.

The preparation of particles and respirable aggregates using a controlled precipitation (CP) method includes a batch controlled precipitation process. An aliquot of 1.77 grams of Brij® 98 (polyoxyethylene (20) oleyl ether) is dissolved in 148.33 grams of deionized water. The aqueous solution is then recirculated, using a centrifugal pump (Cole-Parmer Model 75225-10) at maximum pump speed (9000 rpm), through recirculation loop and through heat exchanger (Exergy Inc. Model 00283-01, series heat exchanger) until the aqueous temperature is 5° C. An aliquot of 30.19 grams of a solution containing 5 wt % ITZ in 1,3-dioxolane is added into the recirculating aqueous solution over about 65 seconds, which results in the controlled precipitation of a particle slurry. The particle size of the particle slurry is measured, without filtration or sonication, using a Coulter LS 230. The particle slurry is then fed to a wiped-film evaporator having a jacket temperature of 40° C., an absolute pressure of 8 mm Hg, and a feed rate of 15 mL/min. The particle size of the solvent stripped slurry is measured, without filtration or sonication, using a Coulter LS 230.

Examples of active agents include, but are not limited to antibiotics; analgesics; anticonvulsants; antipyretics; anti-inflammatories; antitussive expectorants; sedatives; antidiabetics, antifungals, antiepileptics, antineoplastics; antiulcer agents; antiparkinsonian agents, antirheumatics, appetite suppressants, biological response modifiers, cardiovascular, agents, central nervous system stimulants, contraceptive agents, diagnostic agents, dopamine receptor agonists, erectile dysfunction agents, fertility agents, gastrointestinal agents, hormones, immunomodulators; antihypercalcexnia agents, mast cell stabilizers, muscle relaxants, nutritional agents, ophthalmic agents, osteoporosis agents, psychotherapeutic agents, parasympathomimetic agents, parasympatholytic agents, respiratory agent, sedative hypnotic agents, skin and mucous membrane agents, smoking cessation agents, steroids, sympatholytic agents, urinary tract agents, uterine relaxants, vaginal agents, vasodilator, antihypertensive, hyperthyroids, antihyperthyroids, anti-asthmatics, nucleic acids; expression vectors; and antivertigo agents. Examples of antitumor or antineoplastic agents include bleomycin hydrochloride, methotrexate, actinomycin D, mitomycin C, vinblastine sulfate, vincristine sulfate, daunonibicin hydrochloride, adriamynin, neocarzinostatin, cytosine arabinoside; fluorouracil, tetrahydrofuryl-5-fluorouracil, picibanil, lentinan, levamisole, bestatin, azimexon, glycyrrhizin, poly A:U, poly ICLC and the like.

Examples of the antibiotics include gentamicin, dibekacin, kanendomycin, lividomycin, tobromycin, amikacin, fradiomycin, sisomysin, tetracycline, oxytetracycline, roliteracycline, doxycycline, ampicillin, piperacillin, ticarcillin, cefalotin, cefaloridine, cefotiam, cefsulodin, cefinenoxime, cefinetazole, cefazollin, cefataxim, cefoperazone, ceftizoxime, moxolactame, thienamycin, sulfazecine, azusleonam, salts thereof, and the like. Examples of the sedative include chlorpromazine, prochloperazine, trifluoperazine, atropine, scopolamine, salts thereof and the like. Examples of the muscle relaxant include pridinol, tubocurarine, pancuronium and the like. Examples of the antiepileptic agent include phenytoin, ethosuximide, acetazolamide, chlordiazepoxide and the like. Examples of the antidepressant include imipramine, clomipramine, onxiptiline, phenelzine and the like. Examples of the antidiabetic agent include: glymidine, glipizide, phenformin, buformin, metformin and the like.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

[1] R. U. Agu, M. I. Ugwoke, M. Armand, R. Kinget, N. Verbeke, The lung as a route for systemic delivery of therapeutic proteins and peptides, Respiratory Research 2 (2001) 198-209.
[2] A. L. Adjei, P. K. Gupta, Inhalation Delivery of Therapeutic Peptides and Proteins, 1997, pp. 913.
[3] S. White, D. B. Bennett, S. Cheu, P. W. Conley, D. B. Guzek, S. Gray, J. Howard, R. Malcolmson, J. M. Parker, P. Roberts, N. Sadrzadeh, J. D. Schumacher, S. Seshadri, G. W. Sluggett, C. L. Stevenson, and N. J. Harper, EXUBERA: Pharmaceutical Development of a Novel Product for Pulmonary Delivery of Insulin, Diabetes Tech. Therapeutics 7 (2005) 896-906.
[4] S. A. Shoyele, A. Slowey, Prospects of formulating proteins/peptides as aerosols for pulmonary drug delivery, Int. J. Pharm. 314 (2006) 1-8.
[5] H. M. Courrier, N. Butz, T. F. Vandamme, Pulmonary drug delivery systems: recent developments and prospects, Crit. Rev. Therapeutic Drug Carrier Systems 19 (2002) 425-498.
[6] M. J. Kwon, J. H. Bae, J. J. Kim, K. Na, E. S. Lee, Long acting porous microparticle for pulmonary protein delivery, Int. J. Pharm. 333 (2007) 5-9.
[7] J. S. Patton, P. R. Byron, Inhaling medicines: delivering drugs to the body through the lungs, Nature Rev. Drug Discovery 6 (2007) 67-74.
[8] V. Codrons, F. Vanderbist, R. K. Verbeeck, M. Arras, D. Lison, V. Preat, R. Vanbever, Systemic delivery of parathyroid hormone (1-34) using inhalation dry powders in rats, J. Pharm. Sci. 92 (2003) 938-950.
[9] L. Garcia-Contreras, H. D. C. Smyth, Liquid-spray or dry-powder systems for inhaled delivery of peptide and proteins?, Am. J. Drug Delivery 3 (2005) 29-45.
[10] D. Traini, P. Young, P. Rogueda, R. Price, The Use of AFM and Surface Energy Measurements to Investigate Drug-Canister Material Interactions in a Model Pressurized Metered Dose Inhaler Formulation, Aerosol Sci. Tech. 40 (2006) 227-236.
[11] P. Rogueda, Novel hydrofluoroalkane suspension formulations for respiratory drug delivery, Expert Opinion Drug Del. 2 (2005) 625-638.
[12] R. O. Williams, III, J. Liu, Formulation of a protein with propellant HFA 134a for aerosol delivery, Eur. J. Pharm. Sci. 7 (1999) 137-144.
[13] R. O. Williams, III, M. Repka, J. Liu, Influence of propellant composition on drug delivery from a pressurized metered-dose inhaler, Drug Dev. Ind. Pharm. 24 (1998) 763-770.
[14] K. A. Johnson, Interfacial phenomena and phase behavior in metered dose inhaler formulations, in: A. J. Hickey (Ed), Inhalation Aerosols: Physical and biological basis for therapy, 2007.
[15] E. A. Quinn, R. T. Forbes, A. C. Williams, M. J. Oliver, L. McKenzie, T. S. Purewal, Protein conformational stability in the hydrofluoroalkane propellants tetrafluoroethane and heptafluoropropane analyzed by Fourier transform Raman spectroscopy, Int. J. Pharm. 186 (1999) 31-41.
[16] M. J. Oliver, L. McKenzie, W. D. Graffiths, G. R. Morgan, N. O'Kelly. Initial assessment of a protein formulated in pressurized mdis for pulmonary delivery, RDD VII, 2000.
[17] C. Benfait, Kos reports achievement of new research and development milestones, Kos Press Release (2004)
[18] J. Heyder, J. Gebhart, G. Rudolf, C. F. Schiller, W. Stahlhofen, Deposition of particles in the human respiratory tract in the size range 0.005-15 mm, J. Aerosol Sci. 17 (1986) 811-825.
[19] A. Ben-Jebria, D. Chen, M. L. Eskew, R. Vanbever, R. Langer, D. A. Edwards, Large porous particles for sustained protection from carbachol-induced bronchoconstriction in guinea pigs, Pharm. Res. 16 (1999) 555-561.
[20] N. Tsapis, D. Bennett, B. Jackson, D. A. Weitz, D. A. Edwards, Trojan particles: large porous carriers of nanoparticles for drug delivery, Proc. Natl. Acad. Sci. U.S.A. 99 (2002) 12001-12005.
[21] L. A. Dellamary, T. E. Tarara, D. J. Smith, C. H. Woelk, A. Adractas, M. L. Costello, H. Gill, J. G.

[21] Weers, Hollow porous particles in metered dose inhalers, Pharm. Res. 17 (2000) 168-174.
[22] Y.-F. Maa, P.-A. Nguyen, T. Sweeney, S. J. Shire, C. C. Hsu, Protein inhalation powders: spray drying vs spray freeze drying, Pharm. Res. 16 (1999) 249-254.
[23] Y.-F. Maa, H. R. Costantino, Spray freeze-drying of biopharmaceuticals: applications and stability considerations, in: H. R. Costantino, M. J. Pikal (Eds), Biotechnology: Pharmaceutical Aspects. 2. Lyophilization of Biopharmaceuticals, American Association of Pharmaceutical Scientists, Arlington, 2004, pp. 519-561.
[24] Y.-F. Maa, S. J. Prestrelski, Biopharmaceutical powders: particle formation and formulation considerations, Curr. Pharm. Biotechnol. 1 (2000) 283-302.
[25] M. Adler, G. Lee, Stability and surface activity of lactate dehydrogenase in spray-dried trehalose, J. Pharm. Sci. 88 (1999) 199-208.
[26] H. R. Costantino, L. Firouzabadian, K. Hogeland, C. C. Wu, C. Beganski, K. G. Carrasquillo, M. Cordova, K. Griebenow, S. E. Zale, M. A. Tracy, Protein spray-freeze drying. Effect of atomization conditions on particle size and stability, Pharm. Res. 17 (2000) 1374-1383.
[27] Y.-F. Maa, P.-A. Nguyen, Method of spray freeze drying proteins for pharmaceutical administration, U.S. Pat. No. 6,284,282 (2001).
[28] S. D. Webb, S. L. Golledge, J. L. Cleland, J. F. Carpenter, T. W. Randolph, Surface adsorption of recombinant human interferon-g in lyophilized and spray-lyophilized formulations, J. Pharm. Sci. 91 (2002) 1474-1487.
[29] X. C. Nguyen, J. D. Herberger, P. A. Burke, Protein powders for encapsulation: a comparison of spray-freeze drying and spray drying of darbepoetin alfa, Pharm. Res. 21 (2004) 507-514.
[30] I. Gonda, Development of a systematic theory of suspension inhalation aerosols. I. A framework to study the effects of aggregation on the aerodynamic behavior of drug particles, Int. J. Pharm. 27 (1985) 99-116.
[31] Y.-H. Liao, M. B. Brown, S. A. Jones, T. Nazir, G. P. Martin, The effects of polyvinyl alcohol on the in vitro stability and delivery of spray-dried protein particles from surfactant-free HFA 134a-based pressurised metered dose inhalers, Int. J. Pharm. 304 (2005) 29-39.
[32] M. Keller, Innovations and perspectives of metered dose inhalers in pulmonary drug delivery, Int. J. Pharm. 186 (1999) 81-90.
[33] C. Vervaet, P. R. Byron, Drug-surfactant-propellant interactions in HFA-formulations, Int. J. Pharm. 186 (1999) 13-30.
[34] F. E. Blondino, P. R. Byron, Surfactant dissolution and water solubilization in chlorine-free liquified gas propellants, Drug Dev. Ind. Pharm. 24 (1998) 935-945.
[35] R. P. S. Peguin, P. Selvam, S. R. P. da Rocha, Microscopic and Thermodynamic Properties of the HFA134a-Water Interface: Atomistic Computer Simulations and Tensiometry under Pressure, Langmuir 22 (2006) 8826-8830.
[36] L. Wu, R. P. S. Peguin, P. Selvam, U. Chokshi, S. R. P. da Rocha, Molecular scale behavior in alternative propellant-based inhaler formulations, in: A. J. Hickey (Ed), Inhalation Aerosols: Physical and biological basis for therapy, 2007.
[37] R. Vanbever, J. D. Mintzes, J. Wang, J. Nice, D. Chen, R. Batycky, R. Langer, D. A. Edwards, Formulation and physical characterization of large porous particles for inhalation, Pharm. Res. 16 (1999) 1735-1742.
[38] D. A. Edwards, J. Hanes, G. Caponetti, J. Hrkach, A. Ben-Jebria, M. L. Eskew, J. Mintzes, D. Deaver, N. Lotan, R. Langer, Large porous particles for pulmonary drug delivery, Science 276 (1997) 1868-1871.
[39] J. Tam, J. T. McConville, R. O. Williams III, K. P. Johnston, Amorphous cyclosporin A nanodispersions for enhanced pulmonary deposition and dissolution. Submitted., J. Pharm. Sci. (2007)
[40] Z. Yu, A. S. Garcia, K. P. Johnston, R. O. Williams III, Spray freezing into liquid nitrogen for highly stable protein nanostructured microparticles, Eur. J. Pharm. Biopharm. 58 (2004) 529-537.
[41] J. D. Engstrom, D. T. Simpson, E. Lai, R. O. Williams III, K. P. Johnston, Morphology of protein particles produced by spray freezing of concentrated solutions, Eur. J. Pharm. Biopharm. 65 (2007) 149-162.
[42] J. D. Engstrom, D. T. Simpson, C. Cloonan, E. Lai, R. O. Williams III, G. B. Kitto, P. Johnston Keith, Stable high surface area lactate dehydrogenase particles produced by spray freezing into liquid nitrogen, Eur. J. Pharm. Biopharm. 65 (2007) 163-174.
[43] Z. Yu, K. P. Johnston, R. O. Williams III, Spray freezing into liquid versus spray-freeze drying: Influence of atomization on protein aggregation and biological activity, Eur. J. Pharm. Sci. 27 (2006) 9-18.
[44] Z. Yu, T. L. Rogers, J. Hu, K. P. Johnston, R. O. Williams III, Preparation and characterization of microparticles containing peptide produced by a novel process: spray freezing into liquid, Eur. J. Pharm. Biopharm. 54 (2002) 221-228.
[45] J. D. Engstrom, E. S. Lai, B. Ludher, B. Chen, T. E. Milner, G. B. Kitto, R. O. Williams III, K. P. Johnston, Formation of stable submicron protein particles by thin film freezing, Pharm. Res. (Submitted)
[46] Z. Jiang, Y. Guan, Flocculation morphology: effect of particulate shape and coagulant species on flocculation, Water Sci. Technol. 53 (2006) 9-16.
[47] I. Goodarz-Nia, D. N. Sutherland, Floc simulation. Effects of particle size and shape, Chem. Eng. Sci. 30 (1975) 407-12.
[48] P. C. Hiemenz, R. Rajagopalan, Principles of colloid and surface chemistry, 1997, PP.
[49] A. P. Philipse, A. M. Wierenga, On the Density and Structure Formation in Gels and Clusters of Colloidal Rods and Fibers, Langmuir 14 (1998) 49-54.
[50] A. P. Philipse, The Random Contact Equation and Its Implications for (Colloidal) Rods in Packings, Suspensions, and Anisotropic Powders, Langmuir 12 (1996) 5971.
[51] T. L. Rogers, A. C. Nelsen, J. Hu, J. N. Brown, M. Sarkari, T. J. Young, K. P. Johnston, R. O. Williams III, A novel particle engineering technology to enhance dissolution of poorly water soluble drugs: spray-freezing into liquid, Eur. J. Pharm. Biopharm. 54 (2002) 271-280.
[52] T. L. Rogers, K. A. Overhoff, P. Shah, P. Santiago, M. J. Yacaman, K. P. Johnston, R. O. Williams III, Micronized powders of a poorly water soluble drug produced by a spray-freezing into liquid-emulsion process, Eur. J. Pharm. Biopharm. 55 (2003) 161-72.
[53] R. O. Williams, III, J. Liu, J. J. Koleng, Influence of metering chamber volume and water level on the emitted dose of a suspension-based pMDI containing propellant 134a, Pharm. Res. 14 (1997) 438-443.

[54] Y. Kim, S. H. Atwell, R. G. Bell, Determination of water in pressurized pharmaceutical metered dose aerosol products, Drug Dev. Ind. Pharm. 18 (1992) 2185-95.

[55] P. G. Smith, Jr., W. Ryoo, K. P. Johnston, Electrostatically Stabilized Metal Oxide Particle Dispersions in Carbon Dioxide, J. Phys. Chem. B 109 (2005) 20155-20165.

[56] E. Berlin, M. J. Pallansch, Densities of several proteins and L-amino acids in the dry state, J. Phys. Chem. 72 (1968) 1887-9.

[57] P. G. A. Rogueda, HPFP, a model propellant for pMDIs, Drug Dev. Ind. Pharm. 29 (2003) 39-49.

[58] R. Ashayer, P. F. Luckham, S. Manimaaran, P. Rogueda, Investigation of the molecular interactions in a pMDI formulation by atomic force microscopy, Eur. J. Pharm. Sci. 21 (2004) 533-543.

[59] D. Traini, M. Young Paul, P. Rogueda, R. Price, In vitro investigation of drug particulates interactions and aerosol performance of pressurised metered dose inhalers, Pharm. Res. 24 (2007) 125-135.

[60] S. L. Nail, S. Jiang, S. Chongprasert, S. A. Knopp, Fundamentals of freeze-drying, in: S. L. Nail, M. J. Akers (Eds), Pharmaceutical Biotechnology. 14. Development and Manufacture of Protein Pharmaceuticals, Kluwer Academic/Plenum Publishers, New York, 2002, pp. 281-360.

[61] S. D. Webb, J. L. Cleland, J. F. Carpenter, T. W. Randolph, A new mechanism for decreasing aggregation of recombinant human interferon-g by a surfactant: slowed dissolution of lyophilized formulations in a solution containing 0.03% polysorbate 20, J. Pharm. Sci. 91 (2002) 543-558.

[62] J. F. Carpenter, B. S. Chang, W. Garzon-Rodriguez, T. W. Randolph, Rational design of stable lyophilized protein formulations: theory and practice, in: J. F. Carpenter, M. C. Manning (Eds), Pharmaceutical Biotechnology. 13. Rational Design of Stable Protein Formulations, Kluwer Academic/Plenum Press, New York, 2002, pp. 109-133.

[63] A. Farahnaky, F. Badii, I. A. Farhat, J. R. Mitchell, S. E. Hill, Enthalpy relaxation of bovine serum albumin and implications for its storage in the glassy state, Biopolymers 78 (2005) 69-77.

[64] B. Y. Shekunov, P. Chattopadhyay, H. H. Y. Tong, A. H. L. Chow, Particle Size Analysis in Pharmaceutics: Principles, Methods and Applications, Pharm. Res. 24 (2007) 203-227.

[65] W. H. Finlay, The mechanics of inhaled pharmaceutical aerosols, New York, 2001, pp.

[66] A. Sihvola, Electromagnetic mixing formulas and applications, 1999, pp.

[67] W. B. Russel, D. A. Saville, W. R. Schowalter, Colloidal dispersions, 1989, pp.

[68] D. Traini, P. Rogueda, P. Young, R. Price, Surface Energy and Interparticle Forces Correlations in Model pMDI Formulations, Pharm. Res. 22 (2005) 816-825.

[69] M. A. Bevan, PhD Dissertation, Carnegie Mellon University, 1999.

[70] R. G. Larson, The Structure and Rheology of Complex Fluids, Oxford University Press Inc., New York, 1999, pp.

[71] P. Tang, J. Greenwood, J. A. Raper, A model to describe the settling behavior of fractal aggregates, J. Colloid Interface Sci. 247 (2002) 210-219.

[72] C. Fargues, C. Turchiuli, Structural characterization of flocs in relation to their settling performances, Chem. Eng. Res. Design 82 (2004) 1517.

[73] H. Abramowitz, P. S. Shah, P. F. Green, K. P. Johnston, Welding Colloidal Crystals with Carbon Dioxide, Macromolecules 37 (2004) 7316-7324.

[74] D. R. Ulrich, Chemical processing of ceramics, Chem. Eng. News 68 (1990) 28-40.

[75] H. D. C. Smyth, A. J. Hickey, R. M. Evans, Aerosol generation from propellant-driven metered dose inhalers, in: J. Hickey Anthony (Ed), Inhalation Aerosols: Physical and Biological Basis for Therapy, 2007, pp. 399-416.

[76] J. Israelachvili, Intermolecular and surface forces, Academic Press, San Diego, 1992, pp.

[77] S. Takashima, Proton fluctuation in protein. Experimental study of the Kirkwood-Shumaker theory, J. Phys. Chem. 69 (1965) 2281-6.

[78] R. Tadmor, The London-van der Waals interaction energy between objects of various geometries, J. Phys.: Condens. Matter 13 (2001) L195-L202.

What is claimed is:

1. Flocculated pharmaceutically active starting drug particles ("starting floc drug particles"), of one or more drugs, the starting floc drug particles having aerodynamic diameters that have not been pre-formed, the starting floc drug particles being positioned in a dry powder inhaler (dpi) having one or more particle exit orifices, the starting floc drug particles being anisotropic and asymmetric such that when the dpi is actuated, the starting floc drug particles pass through the one or more exit orifices of the dpi and into patient air ways, the starting floc drug particles will break up and produce smaller floc drug particles having aerodynamic diameters that are of a size appropriate for deep lung delivery ranging between 1 and 5 microns.

2. The flocculated starting drug particles of claim 1, wherein the starting floc drug particles have been prepared by dissolving the one or more drugs in a solvent to form a mixture of the drug and solvent, rapidly freezing the mixture on a cryogenically cooled surface and removing the solvent to thereby provide the starting floc drug particles.

3. The flocculated starting drug particles of claim 1, wherein one or more of the drug(s) is/are an amorphous drug.

4. The flocculated starting drug particles of claim 1, wherein one or more of the drug(s) is/are a crystalline drug.

5. The flocculated starting drug particles of claim 1, wherein one or more of the drug(s) is an antifungal drug having one or more of azoles and/or allylamines.

6. The flocculated drug particles of claim 1, wherein the one or more drugs are natamycin, flucytosine, miconazole, fluconazole, itraconazole, clotrimazole, econazole, ravuconazole, sulconazole, terconazole, tioconazole, fenticonazole, bifonazole, oxiconazole, ketoconazole, isoconazole, tolnaftate, amorolfine, terbinafine, voriconazol, or posaconazol, or pharmacologically acceptable organic and inorganic salts thereof.

7. The flocculated starting drug particles of claim 1, wherein the one or more drugs comprise itraconazole.

* * * * *